US 7,211,253 B1

(12) United States Patent
Way

(10) Patent No.: US 7,211,253 B1
(45) Date of Patent: May 1, 2007

(54) ERYTHROPOIETIN FORMS WITH IMPROVED PROPERTIES

(75) Inventor: Jeffrey Way, Cambridge, MA (US)

(73) Assignee: Merck Patentgesellschaft Mit Beschrankter Haftung, Darmstadt (DE)

( * ) Notice: Subject to any disclaimer, the term of this patent is extended or adjusted under 35 U.S.C. 154(b) by 114 days.

(21) Appl. No.: 09/708,506

(22) Filed: Nov. 9, 2000

Related U.S. Application Data

(60) Provisional application No. 60/164,855, filed on Nov. 12, 1999.

(51) Int. Cl.
*A61K 39/00* (2006.01)
*A61K 39/395* (2006.01)
*A61K 38/00* (2006.01)
*C07K 14/505* (2006.01)

(52) U.S. Cl. .................. 424/134.1; 530/397; 514/2
(58) Field of Classification Search ................ 530/300, 530/356, 387.1, 387.3, 397, 399; 424/130.1, 424/134.1
See application file for complete search history.

(56) References Cited

U.S. PATENT DOCUMENTS

| | | | |
|---|---|---|---|
| 4,469,797 A | 9/1984 | Albarella |
| 4,522,811 A | 6/1985 | Eppstein et al. |
| 4,667,016 A | 5/1987 | Lai et al. |
| 4,676,980 A | 6/1987 | Segal et al. |
| 4,703,008 A | 10/1987 | Lin |
| 4,732,683 A | 3/1988 | Georgiades et al. |
| 4,737,462 A | 4/1988 | Mark et al. |
| 4,816,567 A | 3/1989 | Cabilly et al. |
| 4,946,778 A | 8/1990 | Ladner et al. |
| 4,975,369 A | 12/1990 | Beavers et al. |
| 5,019,368 A | 5/1991 | Epstein et al. |
| 5,073,627 A | 12/1991 | Curtis et al. |
| 5,082,658 A | 1/1992 | Palladino |
| 5,091,513 A | 2/1992 | Huston et al. |
| 5,114,711 A | 5/1992 | Bell et al. |
| 5,116,964 A | 5/1992 | Capon et al. |
| 5,199,942 A | 4/1993 | Gillis |
| 5,225,538 A | 7/1993 | Capon et al. |
| 5,225,539 A | 7/1993 | Winter |
| 5,258,498 A | 11/1993 | Huston et al. |
| 5,314,995 A | 5/1994 | Fell, Jr. et al. |
| 5,349,053 A | 9/1994 | Landolfi |
| 5,359,035 A | 10/1994 | Habermann |
| 5,399,346 A | 3/1995 | Anderson et al. |
| 5,428,130 A | 6/1995 | Capon et al. |
| 5,441,868 A | 8/1995 | Lin |
| 5,457,038 A | 10/1995 | Trinchieri et al. |
| 5,480,981 A | 1/1996 | Goodwin et al. |
| 5,514,582 A | 5/1996 | Capon et al. |
| 5,538,866 A | 7/1996 | Israeli et al. |
| 5,541,087 A | 7/1996 | Lo et al. |
| 5,543,297 A | 8/1996 | Cromlish et al. |
| 5,547,933 A | 8/1996 | Lin |
| 5,552,524 A | 9/1996 | Basinski et al. |
| 5,585,089 A | 12/1996 | Queen et al. |
| 5,585,097 A * | 12/1996 | Bolt et al. ............... 424/133.1 |
| 5,589,466 A | 12/1996 | Felgner et al. |
| 5,601,819 A | 2/1997 | Wong et al. |
| 5,609,846 A | 3/1997 | Goldenberg |
| 5,614,184 A | 3/1997 | Sytkowski et al. |
| 5,618,698 A | 4/1997 | Lin |
| 5,624,821 A | 4/1997 | Winter et al. |
| 5,639,725 A | 6/1997 | O'Reilly et al. |
| 5,645,835 A | 7/1997 | Fell, Jr. et al. |
| 5,650,150 A | 7/1997 | Gillies |
| 5,650,492 A | 7/1997 | Gately et al. |
| 5,667,776 A | 9/1997 | Zimmerman et al. |
| 5,679,543 A | 10/1997 | Lawlis |
| 5,688,679 A | 11/1997 | Powell |
| 5,691,309 A | 11/1997 | Basinski et al. |
| 5,709,859 A | 1/1998 | Aruffo et al. |
| 5,712,120 A | 1/1998 | Rodriguez et al. |
| 5,719,266 A | 2/1998 | DiMarchi et al. |
| 5,723,125 A | 3/1998 | Chang et al. |
| 5,726,044 A | 3/1998 | Lo et al. |

(Continued)

FOREIGN PATENT DOCUMENTS

AU 21725/88 3/1989

(Continued)

OTHER PUBLICATIONS

Wells, Additivity of Mutational Effects in Proteins, Biochemistry 29:8509-8517 (1990).*

(Continued)

*Primary Examiner*—Marianne P. Allen
*Assistant Examiner*—Regina M. DeBerry
(74) *Attorney, Agent, or Firm*—Kirkpatrick & Lockhart Preston Gates Ellis LLP

(57) ABSTRACT

The invention relates to novel modified erythropoietin (EPO) forms such as fusion proteins comprising a Fc portion of an Ig molecule and a target molecule having the biological activity of EPO. By selective altering of the amino acid sequences of the erythropoietin moiety as well as of the immunoglobulin moiety and the glycosylation pattern of erythropoietin fusion proteins with enhanced biological activity can be obtained. The invention relates also to novel nun-fused EPO molecules which have a pattern of cysteines or disulfide bonding which is distinct from human or animal EPO.

18 Claims, 5 Drawing Sheets

U.S. PATENT DOCUMENTS

Figure 1:
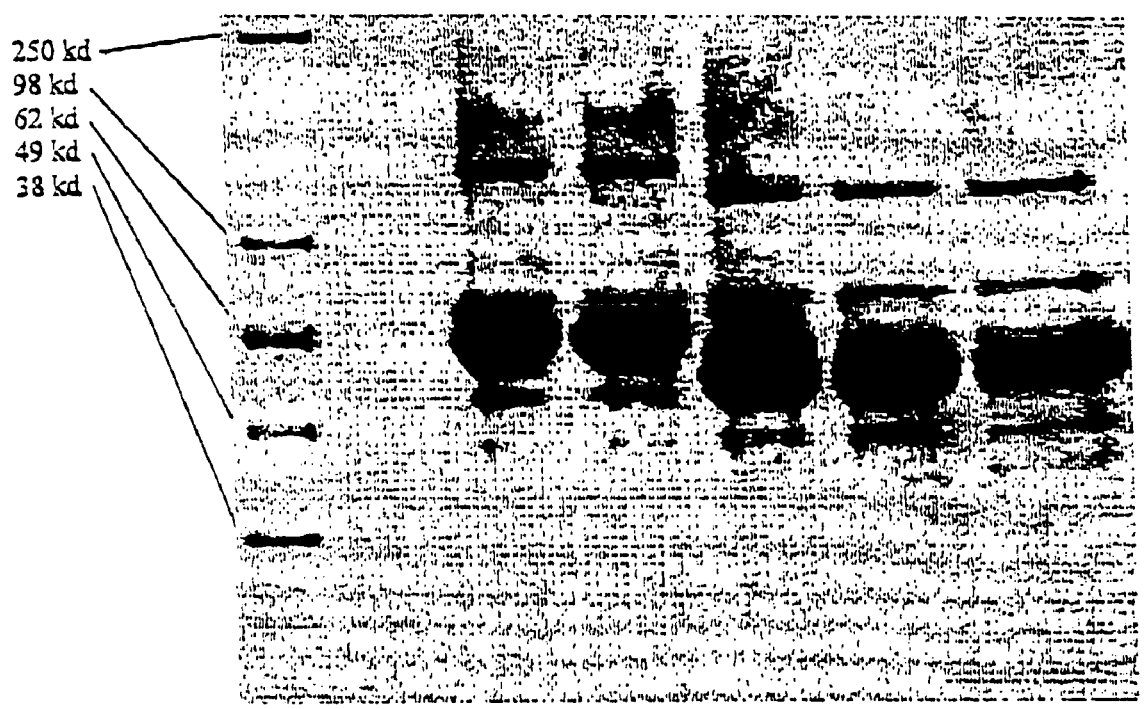

| | | | |
|---|---|---|---|
| 5,728,552 A | 3/1998 | Fujisawa et al. | |
| 5,733,876 A | 3/1998 | O'Reilly et al. | |
| 5,738,852 A | 4/1998 | Robinson et al. | |
| 5,756,349 A | 5/1998 | Lin | |
| 5,756,461 A | 5/1998 | Stephens | |
| 5,759,551 A | 6/1998 | Ladd et al. | |
| 5,770,195 A | 6/1998 | Hudziak et al. | |
| 5,795,779 A | 8/1998 | McCormick | |
| 5,800,810 A | 9/1998 | Doyle et al. | |
| 5,807,715 A | 9/1998 | Morrison et al. | |
| 5,827,516 A | 10/1998 | Urban et al. | |
| 5,827,703 A | 10/1998 | Debs et al. | |
| 5,837,682 A | 11/1998 | Folkman et al. | |
| 5,837,821 A | 11/1998 | Wu et al. | |
| 5,843,423 A | 12/1998 | Lyman et al. | |
| 5,854,205 A | 12/1998 | O'Reilly et al. | |
| 5,856,298 A | 1/1999 | Strickland | |
| 5,858,347 A | 1/1999 | Bauer et al. | |
| 5,885,795 A | 3/1999 | O'Reilly et al. | |
| 5,886,178 A | 3/1999 | Allen et al. | |
| 5,888,772 A * | 3/1999 | Okasinski et al. | 435/69.5 |
| 5,891,680 A | 4/1999 | Lieschke et al. | |
| 5,908,626 A | 6/1999 | Chang et al. | |
| 5,922,685 A | 7/1999 | Rakhmilevich et al. | |
| 5,935,824 A * | 8/1999 | Sgarlato | 435/69.7 |
| 5,955,422 A | 9/1999 | Lin | |
| 5,994,104 A | 11/1999 | Anderson et al. | |
| 5,994,126 A | 11/1999 | Steinman et al. | |
| 6,080,409 A | 6/2000 | Laus et al. | |
| 6,086,875 A | 7/2000 | Blumberg et al. | |
| 6,100,387 A | 8/2000 | Herrmann et al. | |
| 6,169,070 B1 | 1/2001 | Chen et al. | |
| 6,171,588 B1 | 1/2001 | Carron et al. | |
| 6,231,536 B1 | 5/2001 | Lentz | |
| 6,277,375 B1 | 8/2001 | Ward | |
| 6,281,010 B1 | 8/2001 | Gao et al. | |
| 6,284,536 B1 | 9/2001 | Morrison et al. | |
| 6,291,158 B1 | 9/2001 | Winter et al. | |
| 6,335,176 B1 | 1/2002 | Inglese et al. | |
| 6,340,742 B1 | 1/2002 | Burg et al. | |
| 6,348,192 B1 | 2/2002 | Chan et al. | |
| 6,406,689 B1 | 6/2002 | Falkenberg et al. | |
| 6,429,199 B1 | 8/2002 | Krieg et al. | |
| 6,444,792 B1 | 9/2002 | Gray et al. | |
| 6,475,717 B1 | 11/2002 | Enssle et al. | |
| 6,485,726 B1 | 11/2002 | Blumberg et al. | |
| 6,500,641 B1 | 12/2002 | Chen et al. | |
| 6,506,405 B1 | 1/2003 | Desai et al. | |
| 6,551,592 B2 | 4/2003 | Lindhofer et al. | |
| 6,583,272 B1 | 6/2003 | Bailon | |
| 6,586,398 B1 | 7/2003 | Kinstler et al. | |
| 6,608,183 B1 * | 8/2003 | Cox, III | 530/399 |
| 6,617,135 B1 | 9/2003 | Gillies et al. | |
| 6,627,615 B1 | 9/2003 | Debs et al. | |
| 6,646,113 B1 | 11/2003 | Dreyfuss et al. | |
| 2001/0053539 A1 | 12/2001 | Lauffer et al. | |
| 2002/0037558 A1 | 3/2002 | Lo et al. | |
| 2002/0081664 A1 | 6/2002 | Lo et al. | |
| 2002/0142374 A1 | 10/2002 | Gallo et al. | |
| 2002/0146388 A1 | 10/2002 | Gillies | |
| 2002/0147311 A1 | 10/2002 | Gillies et al. | |
| 2002/0192222 A1 | 12/2002 | Blumberg et al. | |
| 2002/0193570 A1 | 12/2002 | Gillies et al. | |
| 2003/0003529 A1 | 1/2003 | Bayer | |
| 2003/0012789 A1 | 1/2003 | Blumberg et al. | |
| 2003/0044423 A1 | 3/2003 | Gillies et al. | |
| 2003/0049227 A1 | 3/2003 | Gillies et al. | |
| 2003/0105294 A1 | 6/2003 | Gillies et al. | |
| 2003/0139365 A1 | 7/2003 | Lo et al. | |
| 2003/0139575 A1 | 7/2003 | Gillies | |
| 2003/0157054 A1 | 8/2003 | Gillies et al. | |
| 2003/0166163 A1 | 9/2003 | Gillies | |
| 2003/0166877 A1 | 9/2003 | Gillies et al. | |
| 2004/0013640 A1 | 1/2004 | Zardi et al. | |
| 2004/0033210 A1 | 2/2004 | Gillies | |
| 2004/0043457 A1 | 3/2004 | Schumacher et al. | |
| 2004/0053366 A1 | 3/2004 | Lo et al. | |
| 2004/0072299 A1 | 4/2004 | Gillies et al. | |
| 2004/0082039 A1 | 4/2004 | Gillies et al. | |

FOREIGN PATENT DOCUMENTS

| | | |
|---|---|---|
| CN | 93100115.3 | 7/1993 |
| DE | 37 12985 | 11/1988 |
| DE | 37 12985 A1 | 11/1988 |
| EP | 0 158 198 A1 | 10/1985 |
| EP | 0 211 769 A2 | 2/1987 |
| EP | 0 237 019 A2 | 9/1987 |
| EP | 0 256 714 A2 | 2/1988 |
| EP | 0 294 703 A2 | 12/1988 |
| EP | 0 308 936 B1 | 3/1989 |
| EP | 0 314 317 B1 | 5/1989 |
| EP | 0 318 554 B1 | 6/1989 |
| EP | 0 319 012 A2 | 6/1989 |
| EP | 0 326 120 B1 | 8/1989 |
| EP | 0 350 230 A2 | 1/1990 |
| EP | 0 375 562 B1 | 6/1990 |
| EP | 0 396 387 A2 | 11/1990 |
| EP | 0 439 095 A2 | 7/1991 |
| EP | 0 511 747 A1 | 11/1992 |
| EP | 0 519 596 A1 | 12/1992 |
| EP | 0 601 043 B1 | 6/1994 |
| EP | 0 640 619 A1 | 3/1995 |
| EP | 0 668 353 A1 | 8/1995 |
| EP | 0 699 755 A2 | 3/1996 |
| EP | 0 428 596 B1 | 4/1996 |
| EP | 0 706 799 A2 | 4/1996 |
| EP | 0 428 267 B1 | 12/1996 |
| EP | 0 790 309 A1 | 8/1997 |
| EP | 0 433 827 B1 | 3/1998 |
| EP | 0 668 351 B1 | 9/1999 |
| EP | 1 088 888 A1 | 4/2001 |
| GB | 2 188 638 | 10/1987 |
| GB | 2 292 382 A | 2/1996 |
| JP | 63-267278 | 11/1988 |
| JP | 63-267296 | 11/1988 |
| WO | WO 88/00052 | 1/1988 |
| WO | WO 88/09344 | 12/1988 |
| WO | WO 89/02922 | 4/1989 |
| WO | WO 89/09620 | 10/1989 |
| WO | WO 90/03801 | 4/1990 |
| WO | WO 91/00360 | 1/1991 |
| WO | WO 91/04329 | 4/1991 |
| WO | WO 91/08298 | 6/1991 |
| WO | WO 91/13166 | 9/1991 |
| WO | WO 91/14438 | 10/1991 |
| WO | WO 92/02240 | 2/1992 |
| WO | WO 92/08495 | 5/1992 |
| WO | WO 92/08801 | 5/1992 |
| WO | WO 92/10755 | 6/1992 |
| WO | WO 92/16562 | 10/1992 |
| WO | WO 93/03157 | 2/1993 |
| WO | WO 93/10229 | 5/1993 |
| WO | WO 93/20185 | 10/1993 |
| WO | WO 94/24160 | 10/1994 |
| WO | WO 94/25055 | 11/1994 |
| WO | WO 94/25609 | 11/1994 |
| WO | WO 95/05468 | 2/1995 |
| WO | WO 95/21258 | 8/1995 |
| WO | WO 95/28427 | 10/1995 |
| WO | WO 95/31483 | 11/1995 |
| WO | WO 96/04388 | 2/1996 |
| WO | WO 96/05309 | 2/1996 |
| WO | WO 96/08570 | 3/1996 |

| | | |
|---|---|---|
| WO | WO 96/18412 | 6/1996 |
| WO | WO 96/31526 | 10/1996 |
| WO | WO 96/40792 | 12/1996 |
| WO | WO 97/00317 | 1/1997 |
| WO | WO 97/00319 | 1/1997 |
| WO | WO 97/15666 | 5/1997 |
| WO | WO 97/20062 | 6/1997 |
| WO | WO 97/24137 | 7/1997 |
| WO | WO 97/24440 | 7/1997 |
| WO | WO 97/26335 | 7/1997 |
| WO | WO 97/30089 | 8/1997 |
| WO | WO 97/33617 | 9/1997 |
| WO | WO 97/33619 | 9/1997 |
| WO | WO 97/34631 | 9/1997 |
| WO | WO 97/43316 | 11/1997 |
| WO | WO 98/00127 | 1/1998 |
| WO | WO 98/06752 | 2/1998 |
| WO | WO 98/28427 | 7/1998 |
| WO | WO 98/30706 | 7/1998 |
| WO | WO 98/46257 | 10/1998 |
| WO | WO 98/59244 | 12/1998 |
| WO | WO 99/02709 * | 1/1999 |
| WO | WO 99/03887 | 1/1999 |
| WO | WO 99/29732 | 6/1999 |
| WO | WO 99/43713 | 9/1999 |
| WO | WO 99/52562 | 10/1999 |
| WO | WO 99/53958 | 10/1999 |
| WO | WO 99/60128 | 11/1999 |
| WO | WO 99/62944 | 12/1999 |
| WO | WO 99/66054 | 12/1999 |
| WO | WO 00/01822 | 1/2000 |
| WO | WO 00/11033 | 3/2000 |
| WO | WO 00/24893 | 5/2000 |
| WO | WO 00/34317 | 6/2000 |
| WO | WO 00/40615 | 7/2000 |
| WO | WO 00/68376 | 11/2000 |
| WO | WO 00/69913 | 11/2000 |
| WO | WO 00/78334 A1 | 12/2000 |
| WO | WO 01/07081 A1 | 2/2001 |
| WO | WO 01/10912 A1 | 2/2001 |
| WO | WO 01/36489 A2 | 5/2001 |
| WO | WO 01/58957 A2 | 8/2001 |
| WO | WO 02/02143 A2 | 1/2002 |
| WO | WO 02/066514 A2 | 8/2002 |
| WO | WO 02/072605 A2 | 9/2002 |
| WO | WO 02/079232 A2 | 10/2002 |
| WO | WO 02/079415 A2 | 10/2002 |
| WO | WO 02/090566 A2 | 11/2002 |
| WO | WO 03/015697 A2 | 2/2003 |
| WO | WO 03/077834 A2 | 5/2003 |
| WO | WO 03/048334 A2 | 6/2003 |

OTHER PUBLICATIONS

Ngo et al. The Protein Folding Problem and Tertiary Structure Prediction, pp. 433-440 and 492-495 (1994).*

Angal et al. (1993), "A Single Amino Acid Substitution Abolishes the Heterogeneity of Chimeric Mouse/Human (IgG4) Antibody," *Molecular Immunology*, 30:105-108.

Bitoni et al. (2002), "Transepithelial Absorption of an Erythropoietin-Fc Fusion Protein After Delivery to the Central Airways," *Respiratory Drug Delivery*, 8:309-312.

Darling et al. (2002), "Glycosylation of Erythropoietin Affects Receptor Binding Kinetics: Role of Electrostatic Interactions," *Biochemistry*, 41:14524-14531.

Fibi et al. (1995), "N- and O-Glycosylation Muteins of Recombinant Human Erythropoietin Secreted From BHK-21 Cells," *Blood*, 85:1229-1236.

Hammerling et al. (1996), "In vitro bioassay for human erythropoietin based on proliferative stimulation of an erythroid cell line and analysis of carbohydrate-dependent microheterogeneity," *Journal of Pharmaceutical and Biomedical Analysis*, 14:1455-1469.

Kitamura et al. (1989), "Establishment and Characterization of a Unique Human Cell Line that Proliferates Dependently on GM-CSF, IL-3, or Erythropoietin," *Journal of Cellular Physiology*, 140:323-334.

Locatelli et al. (2001), "Darbepoetin alfa Amgen," *Current Opinion in Investigational Drugs*, 2:1097-1104.

Spiekermann et al. (2002), "Receptor-mediated Immunoglobulin G Transport Across Mucosal Barriers in Adult Life: Functional Expression of FcRn in the Mammalian Lung," *J. Exp. Med.*, 196:303-310.

Syed et al. (1998), "Efficiency of signalling through cytokine receptors depends critically on receptor orientation," *Nature*, 395:511-516.

U.S. Appl. No. 07/348,237, filed May 5, 1989, Rosenblum et al.

Abaza et al., (1992), "Effects of Amino Acid Substitutions Outside an Antigenic Site on Protein Binding to Monoclonal Antibodies of Predetermined Specificity Obtained by Peptide Immunization," *Journal of Protein Chemistry*, 11:5:433-444.

Abstract XP-002116766, (1996). "Prostaglandins, their inhibitors and cancer," *Prostaglandins, Leukotrienes and Essential Fatty Acids*, 54:2:83-94.

Alfonso et al., (1994), "The Adjuvant Effect of Interleukin-12 in a Vaccine Against Leishmania Major," *Science*, 263:235-237.

Arenberg et al. (1996), "Interferon-γ-inducible Protein 10 (IP-10) Is an Angiostatic Factor That Inhibits Human Non-small Cell Lung Cancer (NSCLC) Tumorigenesis and Spontaneous Metastases," *J. Exp. Med*, 184:981-992.

Bacha et al., (1988), "Interleukin 2 Receptor-Targeted Cytotoxicity Interleukin 2 Receptor-mediated Action of a Diphtheria Toxin-related Interleukin 2 Fusion Protein," *J. Experimental Medicine*, 167:612-622.

Bachelot et al., (Mar. 1998), "Retrovirus-Mediated Gene Transfer of an Angiostatin-Endostatin Fusion protein with Enhanced Anti-Tumor Properties In Vivo," *Proceedings of the Annual Meeting of the American Association for Cancer Research*, 39:271, Abstract #1856.

Barnett et al., (1994), "Purification, characterization and selective inhibition of human prostaglandin G/H synthase 1 and 2 expressed in the baculovirus system," *Biochimica et Biophysica Acta*, 1209:130-139.

Baselga, et al., (1998), "Recombinant Humanized Anti-HER2 Antibody (Herceptin™) Enhances the Antitumor activity of Paclitazel and Doxorubicin against HER3/*neu* Overexpressing Human Breast Cancer Xenografts," *Cancer Research*, 58:2825-2831.

Batova et al., (1999), "The Ch 14.18-GM-CSF Fusion Protein Is Effective at Mediating Antibody-dependent Cellular Cytotoxicity and Complement-dependent Cytotoxicity in Vitro," *Clinical Cancer Research*, 5:4259-4263.

Batra et al., (1993), "Insertion of Constant Region Domains of Human IgG1 into CD4-PE40 Increases Its Plasma Half-Life," *Mol. Immunol.*, 30:379-386.

Becker et al., (1996), "An Antibody-Interleukin 2 Fusion Protein Overcomes Tumor Heterogeneity by Induction of a Cellular Immune Response," *Proc. Natl. Acad. Sci.*, 93:7826-7831.

Becker et al., (1996), "Eradication of human hepatic and pulmonary melanoma metastases in SCID mice by antibody-interleukin 2 fusion proteins," *Proc. Natl. Sci. USA*, 93:2702-2707.

Beutler et al., (1988), "Tumor Necrosis, Cachexia, Shock, and Inflammation: A Common Mediator," *Ann. Rev. Biochem.*, 57:505-518.

Bissery et al., (1997), "The Taxoids," in *Cancer Therapeutics: Experimental and Clinical Agents*, Teicher, ed., 175-193.

Bjorn et al., (1985), "Evaluation of Monoclonal Antibodies for the Development of Breast Cancer Immunotoxins," *Cancer Research*, 45:1214-1221.

Boehm et al., (1997), "Antiangiogenic therapy of experimental cancer does not induce acquired drug resistance," *Nature*, 390:404-407.

Boehm et al., (1998), "Zinc-Binding of Endostatin Is Essential for Its Antiangiogenic Activity," *Biochemical and Biophysical Research Communications*, 252:190-194.

Brooks et al., (1994), "Integrin α$_v$β$_3$ Antagonists Promote Tumor Regression by Inducing Apoptosis of Angiogenic Blood Vessels," *Cell*, 79:1157-1164.

Buchli et al., (1993), "Structural and Biologic Properties of a Human Aspartic Acid-126 Interleukin-2 Analog," *Archives of Biochemistry and Biophysics*, 307:2:411-415.

Burgess et al., (1990), "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," *Journal of Cell Biology*, 111:2129-2138.

Canfield et al., (1991), "The Binding Affinity of Human IgG for its High Affinity Fc Receptor is Determined by Multiple Amino Acids in the CH2 Domain and Is Modulated by the Hinge Region," *Journal of Experimental Medicine*, 173:6:1483-1491.

Cao et al., (1996), "Kringle Domains of Human Angiostatin," *The Journal of Biological Chemistry*, 271:46:29461-29467.

Cao et al., (1997), "Kringle 5 of Plasminogen is a Novel Inhibitor of Endothelial Cell Growth," *The Journal of Biological Chemistry*, 272:36:22924-22928.

Capon et al., (1989), "Designing CD4 immunoadhesins for AIDS therapy," *Nature*, 337:525-531.

Caton et al., (1986), "Structural and functional implications of a restricted antibody response to a defined antigenic region on the influenza virus hemagglutinin," *The EMBO Journal*, 5:7:1577-1587.

Chan et al., (1991), "Induction of Interferon γ Production by Natural Killer Cell Stimulatory Factor: Characterization of the Responder Cells and Synergy with Other Inducers," *J. Exp. Med.*, pp. 869-879.

Chang et al., (1989), "Overview of Interleukin-2 as an Immunotherapeutic Agent," *Seminars in Surgical Oncology*, 5:385-390.

Chang et al., (1996), "A Point Mutation in Interleukin-2 that Alters Ligand Internalization," *Journal of Biological Chemistry*, 271:23:13349-13355.

Chaudhary et al., (1988), "Selective killing of HIV-infected cells by recombinant human CD4-Pseudomonas exotoxin hybrid protein," *Nature*, 335:370-372.

Chaudhary et al., (1989), "A recombinant immunotoxin consisting of two antibody variable domains fused to Pseudomonas exotoxin," *Nature*, 339:394-397.

Chen et al., (1997), "Eradication of Murine Bladder Carcinoma by Intratumor Injection of a Bicistronic Adenoviral Vector Carrying cDNAs for the IL-12 Heterodimer and Its Inhibition by the IL-12 p40 Subunit Homodimer," *Journal of Immunology*, 159:1:351-358.

Cheon et al., (1994), "High-affinity binding sites for related fibroblast growth factor ligands reside within different receptor immunoglobulin-like domains," *Proc. Natl. Acad. Sci. USA*, 91: 989-993.

Chuang et al., (1993), "Effect of new investigational drug taxol on oncolytic activity and stimulation of human lymphocytes," *Gynecol. Oncol.*, 49:291-298.

Cohen, S. L. et al., (1996), "Human leptin characterization," *Nature*, 382:589.

Cole et al., (1997), "Human IgG2 Variants of Chimeric Anti-CD3 Are Nonmitogenic to T Cells," *Journal of Immunology*, 159:3613-3621.

Collins et al., (1988), "Identification of Specific Residues of Human Interleukin 2 that Affect Binding to the 70-kDa Subunit (p70) of the Interleukin 2 Receptor," *Proc. Natl. Acad. Sci*, 85:7709-7713.

Colombo et al., (1996), "Amount of Interleukin 12 Available at the Tumor Site is Critical for Tumor Regression," *Cancer Research*, 56:2531-2534.

D'Amato et al., (1994), "Thalidomide is an inhibitor of angiogenesis," *Proc. Natl. Acad. Sci. USA*, 91:4082-4085.

D'Andrea et al., (1992), "Production of Natural Killer Cell Stimulatory Factor (Interleukin 12) by Peripheral Blood Mononuclear Cells," *J. Exp. Med.*, 176:1387-1398.

Ding et al., (1988), "Zinc-Dependent Dimers Observed in Crystals of Human Endostatin," *Proceedings of the National Academy of Sciences of USA*, 95:10443-10448.

Earnest et al., (1992), "Piroxicam and Other Cyclooxygenase Inhibitors: Potential for Cancer Chemoprevention," *J. Cell. Biochem. Supp*, 161:156-166.

Eisenthal, (1990), "Indomethacin up-regulated the generation of lymphokine-activated killer-cell activity and antibody-dependent cellular cytotoxicity mediated by interleukin-2," *Cancer Immunol. Immunotherap.* 31:342-348.

Fell et al., (1991), "Genetic Construction and Characterization of Fusion Protein Consisting of a Chimeric F(ab') with Specificity for Carcinomas and Human IL-2," *The J. of Immunology*, 146:7:2446-2452.

Fell et al., (1992), "Chimeric L6 antitumor antibody," *The J. of Biol. Chem.*, 267:15552-15558.

Friedman, J. M. et al., (1998), "Leptin and the regulation of body weight in mammals," *Nature*, 395:763-770.

Gasson et al., (1984), "Purified Human Granulocyte Macrophage Colony-Stimulating Factor: Direct Action on Neutrophils," *Science*, 226:1339-1342.

Gately et al., (1998), "The Interleukin-12/Interleukin-12 Receptor system: Role in Normal and Pathologic Immune Responses," *Annu. Rev. Immunol.*, 16:495-521.

Gillessen et al., (1995), "Mouse Interleukin-12 (IL-12) p40 Homodimer: A Potent IL-12 Antagonist," *Eur. J. Immunol.*, 25:200-206.

Gillies et al., (1989), "Expression of Human Anti-Tetanus Toxoid Antibody in Transfected Murine Myeloma Cells," *Bio/Technology*, 7:799-804.

Gillies et al., (1989), "High-Level Expression of Chimeric Antibodies Using Adapted cDNA Variable Region Cassettes," *J. Immunol. Methods*, 125:191-202.

Gillies et al., (1990), "Antigen binding and biological activities of engineered mutant chimeric antibodies with human tumor specificities," *Hum. Antibod. Hybridomas*, 1:1:47-54.

Gillies et al., (1992), "Antibody-Targeted Interleukin 2 Stimulates T-Cell Killing of Autologous Tumor Cells," *Proc. Natl. Acad. Science*, 89:1428-1432.

Gillies et al., (1993), "Biological Activity and In Vivo Clearance of Antitumor Antibody/Cytokine Fusion Proteins," *Bioconjugate Chem.*, 4:230-235.

Gillies et al., (1998), "Antibody-IL-12 fusion proteins are effective in SCID mouse models of prostate and colon carcinoma matastases," *J. Immunology*, 160:2:6195-6203.

Gillies et al., (1999), "Improving the Efficacy of Antibody-Interleukin 2 Fusion Proteins by Reducing Their Interaction with Fc Receptors," *Cancer Research*, 59:2159-2166.

Gillis et al., (1978), "T Cell Growth Factor: Parameters of Production And A Quantitative Microassay for Activity," *Journal of Immunology*, 120:6:2027-2032.

Goeddel et al., (1986), "Tumor Necrosis Factors: Gene Structure and Biological Activities," *Pharm. Sciences*, pp. 597-609.

Gren et al., (1983), "A New Type of Leukocytic Interferon," *Dokl. Biochem.*, 269:91-95.

Griffon-Etienne et al., (1999), "Taxane-induced apoptosis decompresses blood vessels and lowers interstitial fluid pressure in solid tumors: clinical implications," *Cancer Research*, 59:3776-3782.

Grimaldi et al., (1989), "The t(5;14) Chromosomal Translocation in a Case of Acute Lymphocytic Leukemia Joins the Interleukin-3 Gene to the Immunoglobulin Heavy Chain Gene," *Blood*, 73:8:2081-2805.

Guyre et al., (1997), "Increased potency of Fc-receptor-targeted antigens," *Cancer Immunol. Immunother.*, 45:146-148.

Harris et al., (1993), "Therapeutic Antibodies—the Coming of Age," *Tibtech*, 11:42-44.

Harvill et al., (1995), "An IgG3-IL2 Fusion Protein Activates Complement, Binds FcYRI, Generates LAK Activity and Shows Enhanced Binding to the High Affinity IL-2R," *Immunotech.*, 1:95-105.

Harvill et al., (1996), "In vivo properties of an IgG3-IL-2 fusion protein: A general strategy for immune potentiation," *Journal of Immunology*, 157:7:3165-3170.

Hazama et al., (1993), "Adjuvant-Independent Enhanced Immune Responses to Recombinant Herpes Simplex Virus Type 1 Glycoprotein D by Fusion with Biologically Active Interleukin-2," *Vaccine*, 11:6:629-636.

He et al., (1998), "Humanization and Pharmacokinetics of Monoclonal Antibody with Specificity for Both E- and P-Selectin," *J. Immunol.*, 1029-1035.

Heijnen et al., (1996), "Antigen Targeting to Myeloid-specific Human FcT RI/CD64 Triggers Enhanced Antibody Responses in Transgenic Mice," *J. Clin. Invest.*, 97:2:331-338.

Heinzel et al., (1997), "In Vivo Production and Function of IL-12 p40 Homodimers," *J. Immunol.*, 158:4381-4388.

Hellstrom et al., (1986), "Antitumor effects of L6, and IgG2a antibody that reacts with most human carcinomas," *Proc. Natl. Acad. Sci.*, 83:18: 7059-7063.

Henkart, (1985), "Mechanism of Lymphocyte-Mediated Cytotoxicity," *Ann. Rev. Immunol.*, 3:31-58.

Herrmann et al., (1989), "Hematopoeitic Responses With Advanced Malignancy Treated With Recombinant Human Granulocyte-Macrophage Colony-Stimulating Factor," *Journal of Clinical Oncology*, 7:2:159-167.

Hohenester et al., (1998), "Crystal Structure of the Angiogenesis Inhibitor Endostatin at 1.5 Å Resolution," *EMBO Journal*, 17:6:1656-1664.

Holden et al., (2001), "Augmentation of Anti-Tumor Activity of KS-IL2 Immunocytokine with Chemotherapeutic Agents," *Proceedings of the American Association for Cancer Research*, 42:683, Abstract No. 3675.

Holden et al., (2001), "Augmentation of Antitumor activity of an Antibody-Interleukin 2 Immunocytokine with Chemotherapeutic Agents," *Clinical Cancer Research*, 7:2862-2869.

Hoogenboom et al., (1991), "Construction and expression of antibody-tumor necrosis factor fusion proteins," *Molecular Immunology*, 28:9:1027-1037.

Hoogenboom et al., (1991), "Targeting of Tumor Necrosis Factor to Tumor Cells Secretion by Myeloma Cells of a Genetically Engineered Antibody-Tumor Necrosis Factor Hybrid Molecule," *Biochim. and Biophys. Acta*, 1096:4:345-354 (Abstract).

Hornick et al, (1999), "Pretreatment with a monoclonal antibody/interleukin-2 fusion protein directed against DNA enhances the delivery of therapeutic molecules to solid tumors," *Clin. Cancer Res.*, 5:51-60.

Hu et al., (1996), "A Chimeric Lym-1/Interleukin 2 Fusion Protein for Increasing Tumor Vascular Permeability and Enhancing Antibody Uptake[1]," *Cancer Research*, 56:4998-5004.

Huck et al., (1986), "Sequence of a human immunoglobulin gamma 3 heavy chain constant region gene: comparison with the other human Cγ genes," *Nucleic Acids Research*, vol. 14:4:1779-1789.

Huse et al., (1989), "Generation of a Large Combinatorial Library of the Immunoglobulin Repertoire in Phage Lambda," *Science*, 246:1275-1281.

Ingber et al., (1990), "Synthetic analogues of fumagillin that inhibit angiogenesis and suppress tumour growth," *Nature*, 348:555-557.

Jones et al., (1986), "Replacing the complementarity-determining regions in a human antibody with those from a mouse," *Nature*, 321:6069:522-525.

Ju et al., (1987), "Structure-Function Analysis of Human Interleukin-2," *Journal of Biological Chemistry*, 262:12:5723-5731.

Jung et al., (1986), "Activation of human peripheral blood mononuclear cells by anti-T3: Killing of tumor target cells coated with anti-target-anti-T3 conjugates," *Proc. Natl. Acad. Sci.*, 83:4479-4483.

Junghans et al., (1996), "The protection receptor of IgG catabolism is the B2-micorgobulin-containing neonatal intestinal transport receptor," *Proc. Natl. Acad. Sci.*, 93:11:5512-5516.

Kang et al., (1991), "Antibody redesign by chain shuffling from random combinatorial immunoglobulin libraries," *Proc. Natl. Acad. Sci.*, 88:11120-11123.

Kappel et al., (1992), "Regulating gene expression in transgenic animals," *Current Opinion in Biotechnology* 3:548:553.

Karpovsky et al., (1984), "Production of Target-Specific Effector Cells using Hetero-Cross Linked Aggregate Containing Anti-Target Cell and AntiFcλ Receptor Antibodies," *Journal of Experimental Medicine*, 160:6:1686-1701.

Kendra et al., (1999), "Pharmacokinetics and Stability of the ch 14.18-Interleukin-2 Fusion Protein in Mice," *Cancer Immunol. Immunotherapy*, 48:219-229.

Kim et al., (1997), "An Ovalbumin-IL-12 fusion protein is more effective than ovalbumin plus free recombinant IL-12 in inducing a T helper cell type 1-dominated immune response and inhibiting antigen-specific IgE production," *Journal Immunology*, 158:9:4137-4144.

Kim et al., (1999), "Cytokine Molecular Adjuvants Modulate Immune Responses Induced by DNA Vaccine Constructs for HIV-1 and SIV," *Journal of Interferon and Cytokine Research*, 19:77-84.

Kranz et al., (1984), "Attachment of an anti-receptor antibody to non-target cells renders them susceptible to lysis by a clone of cytotoxic T lymphocytes," *Proc. Natl. Acad. Sci.*, 81:7922-7926.

Kuo et al., (2001), "Oligomerization-dependent Regulation of Motility and Morphogenesis by the Collagen XVIII NC1/Endostatin Domain," *Journal of Cell Biology*, 152:6:1233-1246.

LaVallie et al., (1993), "Cloning and Functional Expression of a cDNA Encoding the Catalytic Subunit of Bovine Enterokinase," *Journal of Biological Chemistry*, 268:31:23311-23317.

Lazar et al., (1988), "Transforming Growth Factor α Mutation of Aspartic Acid 47 and Leucine 48 Results in Different Biological Activities," *Molecular and Cellular Biology*, 8:3:1247-1252.

LeBerthon et al., (1991), "Enhanced Tumor Uptake of Macromolecules Induced by a Novel Vasoactive Interleukin 2 Immunoconjugate," *Cancer Research*, 51:2694-2698.

Lieschke, et al., (1997), "Bioactive murine and human interleukin-12 fusion proteins which retain antitumor activity in vivo," *Nature Biotechnology*, 15:1:35-40.

Linsley et al., (1991), "CTLA-4 is a Second Receptor for B Cell Activation Antigen B7," *Journal of Experimental Medicine*, 174:3:561-569.

Liu et al., (1985), "Heteroantibody Duplexes Target Cells for Lysis by Cytotoxic T Lymphocytes," *Proc. Natl. Acad. Sci.*, 82:8648-8652.

Liu et al., (1988), "Hormone Conjugated with Antibody to CD3 Mediates Cytotoxic T Cell Lysis of Human Melanoma Cells," *Science*, 239:395-398.

Liu et al., (1998), "Immunostimulatory CpG Oligodeoxynucleotides Enhance the Immune Response to Vaccine Strategies Involving Granulocyte-Macrophage Colony-Stimulating Factor," *Blood*, 92:10:3730-3736.

Lo et al., (1998), "High Level Expression and Secretion of Fc-X Fusion Proteins in Mammalian Cells," *Protein Engineering*, 11:6:495-500.

Lode et al., (1998), "Immunocytokines: a promising approach to cancer immunotherapy," *Pharmacol. Thera.*, 80:3:277-292.

Lode et al., (1998), "Natural Killer Cell-Mediated Eradication of Neuroblastoma Metastases to Bone Marrow by Targeted Interleukin-2 Therapy," *Blood*, 91:5:1706-1715.

Lode et al., (1999), "Synergy between an antiangiogenic integrin $\alpha_v$ antagonist and an antibody-cytokine fusion protein eradicates spontaneous tumor metastases," *Proc. Natl. Acad. Sci.*, 96:1591-1596.

Lode et al., (1999), "Tumor-targeted IL-2 amplifies T cell-mediated immune response induced by gene therapy with single-chain IL-12," *Proc. Natl. Acad. Sci.*, 96:8591-8596.

Lode et al., (2000), "Amplification of T Cell Mediated Immune Responses by Antibody-Cytokine Fusion Proteins," *Immunological Investigations*, 29:2:117-120.

Maloney et al., (1994), "Phase I Clinical Trial Using Escalating Single-Dose Infusion of Chimeric Anti-CD20 Monoclonal Antibody (IDEC-C2B8) in Patients with Recurrent B-Cell Lymphoma," *Blood*, 84:8:2457-2466.

Mark et al., (1992), "Expression and characterization of hepatocyte growth factor receptor-IgG fusion proteins," *Journal of Biological Chemistry*, 267:36:26166-26171.

Martinotti et al., (1995), "CD4 T Cells Inhibit in vivo the CD8-Mediated Immune Response Against Murine Colon Carcinoma Cells Transduced with Interleukin-12 Genes," *Eur. J. Immunol.* 25:137-146.

Medesan et al., (1997), "Delineation of the Amino Acid Residues Involved in Transcytosis and Catabolism of Mouse IgG1$^1$," *J. Immunology*, 158:5:2211-2217.

Mestre et al., (1997), "Retinoids Suppress Epidermal Growth Factor-induced Transcription of Cyclooxygenase-2 in Human Oral Squamous Carcinoma Cells," *Cancer Research*, 57:2890-2895.

Mosmann et al., (1989), "TH1 and TH2 CELLS: Different Patterns of Lymphokine Secretion Lead to Different Functional Properties," *Ann. Rev. Immunol*, 7:145-173.

Mott et al., (1995), "The Solution Structure of the F42A Mutant of Human Interleukin 2," *J. Mol. Biol.*, 247:979-994.

Mullins et al., (1998), "Interleukin-12 overcomes paclitaxel-mediated suppression of T-cell proliferation," *Immunopharmacol. Immunotoxicol.*, 20:4:473-492.

Murphy et al., (1986), "Genetic construction, expression, and melanoma-selective cytotoxicity of a diphtheria toxin-related α-melanocyte-stimulating hormone fusion protein," *Proc. Natl. Acad. Sci.*, 83:8258-8262.

Murphy, (1988), "Diphtheria-related peptide hormone gene fusions: A molecular gene approach to chimeric toxin development," *Immunotoxins*, 123-140.

Nedwin et al., (1985), "Human Lymphotoxin and Tumor Necrosis Factor Genes: Structure, Homology and Chromosomal Localization," *Nucleic Acids Research*, 13:17:6361-6373.

Netti et al., (1995), "Time-dependent behavior of interstitial fluid pressure in solid tumors: implications for drug delivery," *Cancer Research*, 55:5451-5458.

Netti et al., (1999), "Enhancement of fluid filtration across tumor vessels: implication for delivery of macromolecules," *Proc. Nat. Acad. Sci*, 96:3137-3142.

Neuberger et al., (1984), "Recombinant Antibodies Possessing Novel Effector Functions," *Nature*, 312:604-608.

O'Reilly et al., (1994), "Angiostatin: A Novel Angiogenesis Inhibitor That Mediates the Suppression of Metastases by a Lewis Lung Carcinoma," *Cell*, 79:315-328.

O'Reilly et al., (1996), "Angiostatin induces and sustains dormancy of human primary tumors in mice," *Nature Medicine*, 2:6:689-692.

O'Reilly et al., (1997), "Endostatin: An Endogenous Inhibitor of Angiogenesis and Tumor Growth," *Cell*, 88:277-285.

Pastan et al., (1989), "Pseudomonas Exotoxin: Chimeric Toxins," *Journal of Biological Chemistry*, 264:26:15157-15160.

Paul et al., (1988), "Lymphotoxin," *Ann. Rev. Immunol.*, 6:407-438.

Perez et al., (1986), "Specific Targeting of Human Peripheral Blood T Cells by Heteroaggregates Containing Anti-T3 Crosslinked to Anti-Target cell antibodies," *J. Exp. Medicine*, 163:166-178.

Perez et al., (1989), "Isolation and Characterization of a cDNA Encoding the KS1/4 Epithelial Carcinoma Marker," *Journal of Immunology*, 142:10:3662-3667.

Polizzi et al., (1999), "A novel taxane with improved tolerability and therapeutic activity in a panel of human tumor xenografts," *Cancer Research*, 59:1036-1040.

Putzer et al., (1997), "Interleukin 12 and B7-1 Costimulatory Molecule Expressed by an Adenovirus Vector Act Synergistically to Facilitate Tumor Regression," *Proc. Nat'l Acad. Sci.*, 94:20:10889-10894.

Reisfeld et al., (1996), "Recombinant antibody fusion proteins for cancer immunotherapy," *Current Topics in Microbiology and Immunology*, 27-53.

Reisfeld et al., (1997), "Immunocytokines: a new approach to immunotherapy of melanoma," *Melanoma Research*, 7:2:S99-S106.

Riethmuller et al., (1994), "Randomised trial of monoclonal antibody for adjuvant therapy of resected Dukes' C colorectal carcinoma," *The Lancet*, 343:1177-1183.

Roessler et al., (1994), "Cooperative interactions between the interleukin 2 receptor α and β chains alter the interleukin 2-binding affinity of the receptor subunits," *Proc. Natl. Acad. Sci.*, 91:3344-3347.

Roitt et al., (1993), "The Role of TH Cells in the Selection of Effector Mechanisms Directed Against Target Antigens," *Immunology*, Third Edition, 8.3-8.4.

Rosenberg, (1988), "Immunotherapy of Cancer Using Interleukin 2: current status and future prospects," *Immunology Today*, 9:2:58-62.

Rozwarski et al., (1994), "Structural comparisons among the short-chain helical cytokines," *Structure*, 2:3:159-173.

Santon et al., (1986), "Effects of Epidermal Growth Factor Receptor Concentration on Tumorigenicity of A431 Cells in Nude Mice," *Cancer Research*, 46:4701-4705.

Sasaki et al., (1998), "Structure, function and tissue forms of the C-terminal globular domain of collagen XVII containing the angiogenesis inhibitor endostatin," *The EMBO Journal*, 17:15:4249-4256.

Sauve et al., (1991), "Localization in human interleukin 2 of the binding site of the α chain (p55) of the interleukin 2 receptor," *Proc. Natl. Acad. Sci.*, 88:4636-4640.

Schnee et al., (1987), "Construction and expression of a recombinant antibody-targeted plasminogen activator," *Proc. Natl. Acad. Sci.*, 84:6904-6908.

Schoenhaut et al., (1992), "Cloning and Expression of Murine IL-12," *Journal of Immunology*, 148:11:3433-3340.

Senter et al., (1988), "Anti-tumor effects of antibody-alkaline phosphatase conjugates in combination with etoposide phosphate," *Proc. Natl. Acad. Sci.*, 85:13:4842-4846.

Shanafelt et al., (2000), "A T-cell-selective interleukin 2 mutein exhibits potent antitumor activity and is well tolerated in vivo," *Nature Biotechnology*, 18:1197-1202.

Sharma et al., (1999), "T cell-derived IL-10 promotes lung cancer growth by suppressing both T cell and APC function," *Journal of Immunology*, 163:5020-5028.

Shen et al., (1986), "Heteroantibody-Mediated Cytotoxicity: Antibody to the high affinity Fc receptor for IgG mediates cytotoxicity by human monocytes that is enhanced by interferon-λ and is not blocked by human IgG," *Journal of Immunology*, 137:11:3378:3382.

Shiff et al., (1995), "Sulindac Sulfide, an Asprin-like Compound, Inhibits Proliferation, Causes Cell Cycle Quiescence, and Induces Apoptosis in HT-29 Colon Adenocarcinoma Cells," *Journal of Clinical Investigation*, 96:491-503.

Shin et al., (1990), "Expression and characterization of an antibody binding specificity joined to insulin-like growth factor 1: Potential applications for cellular targeting," *Proc. Natl. Acad. Sci.*, 87:5322-5326.

Sim et al., (1997), "A Recombinant Human Angiostatin Protein Inhibits Experimental Primary and Metastatic Cancer," *Cancer Research*, 57:1329-1334.

Stevenson et al., (1997), "Conjugation of Human Fcγ in Closed-Hinge or Open-Hinge Configuration to Fab'γ and Analogous Ligands," *Journal of Immunology*, 158:2242-2250.

Sulitzeanu et al., (1993), "Immunosuppressive factors in human cancer," *Adv. Cancer Research*, 60:247-267.

Taniguchi et al., (1983), "Structure and expression of a cloned cDNA for human interleukin-2," *Nature*, 302:305-309.

Tao et al., (1989), "Studies of Aglycosylated Chimeric Mouse IgG: Role of Carbohydrate in the Structure and Effector Functions Mediated by the Human IgG Constant Region," *Journal of Immunology*, 143:8:2595-2601.

Tao et al., (1993), "Structural Features of Human Immunoglobulin G that Determine Isotype-Differences in Complement Activation," *Journal of Experimental Medicine*, 178:2:661-667.

Teicher et al., (1994), "Potentiation of Cytotoxic Cancer Therapies by TNP-470 Alone and With Other Anti-Angiogenic Agents," *Int. J. Cancer*, 57:920-925.

*The Merck Manual of Diagnosis and Therapy*, 990-993, 1278-1283 (17th ed. 1999).

Till et al., (1988), "An Assay that Predicts the Ability of Monoclonal Antibodies to Form Potent Ricin A Chain-containing Immunotoxins," *Cancer Research*, 48:5:1119-1123.

Till et al., (1988), "HIV-Infected Cells are Killed by rCD4-Ricin A Chain," *Science*, 242:1166-1168.

Trinchieri, (1994), "Interleukin-l2: A Cytokine Produced by Antigen-Presenting Cell With Immunoregulatory Functions in the Generation of T-Helper Cells Type 1 and Cytotoxic Lymphocytes," *Blood*, 84:4008-4027.

Vagliani et al., (1996), "Interleukin 12 Potentiates the Curative Effect of a Vaccine Based on Interleukin 2-transduced Tumor Cells," *Cancer Research*, 56:467-470.

Varki et al., (1984), "Antigens Associated with a human lung adenocarcinoma defined by monoclonal antibodies," *Cancer Research*, 44:681-687.

Verhoeyen et al., (1988), "Reshaping Human Antibodies: Grafting an Antilysozyme Activity," *Science*, 239:1534-1536.

Villunger et al., (1997), "Constitutive expression of Fas (Apo-1/CD95) ligand on multiple myeloma cells: a potential mechanism of tumor-induced suppression of immune surveillance," *Blood*, 90:1:12-20.

Watanabe et al., (1997), "Long-term depletion of naive T cells in patients treated for Hodgkin's disease," *Blood*, 90:9:3662-3672.

Williams et al., (1986), "Production of antibody-tagged enzymes by myeloma cells: application to DNA polymerase I Klenow fragment," *Gene*, 43:319-324.

Williams et al., (1987), "Diphtheria toxin receptor binding domain substitution with interleukin-2: genetic construction and properties of a diphtheria toxin-related interleukin-2 fusion protein," *Protein Engineering*, 1:6:493-498.

Wooley et al., (1993), "Influence of a Recombinant Human Soluble Tumor Necrosis Factor Receptor Fc Fusion Protein on Type II Collagen-Induced Arthritis in Mice," *Journal Immunology*, 151: 6602-6607.

Wu et al., (1997), "Suppression of Tumor Growth with Recombinant Murine Angiostatin," *Biochemical and Biophysical Research Communications*, 236:651-654.

Xiang et al., (1997), "Elimination of Established Murine Colon Carcinoma Metastases by Antibody-Interleukin 2 Fusion Protein Therapy," *Cancer Research*, 57:4948-4955.

Zheng et al., (1995), "Administration of noncytolytic IL-10/Fc in muring models of lipopolysaccharide-induced septic shock and allogenic islet transplantation," *Journal of Immunology*, 154:5590-5600.

Xu et al., (1994), "Residue at Position 331 in the IgG1 and IgG4 CH2 Domains Contributes to Their Differential Ability to Bind and Activate Complement," *J. Biol. Chem.*, 269:3469-3474.

International Search Report for International Application No. PCT/EP00/10843, mailed Jul. 20, 2001.

Boissel et al., (1993), "Erythropoietin Structure-Function Relationships," *J. Biol. Chem.*, 268:15983-15993.

Wen et al., (1993), "Erythropoietin Structure-Function Relationships: High Degree of Sequence Homology Among Mammals," *Blood*, 82:1507-1516.

Briggs et al., (1974), "Hepatic Clearance of Intact and Desialylated Erythropoietin," *American Journal of Physiology*, 227:1385-1388.

Egrie et al., (2001), "Development and Characterizarion of Novel Erythropoiesis Stimulating Protein (NESP)," *Nephrol. Dial. Transplant.*, 16:3-13.

Kato et al., (1997), "Mechanism for the Nonlinear Pharmacokinetics or Erythropoietin in Rats," *The Journal of Pharmacology and Experimental Therapeutics*, 283:520-527.

Kato et al., (1998), "Pharmacokinetics of Erythropoietin in Genetically Anemic Mice," *Drug Metabolism and Disposition*, 26:126-131.

Macdougall, (2002), "Optimizing the Use of Erythropoietic Agents—Pharmacokinetic and Pharmacodynamic Considerations," *Nephrol. Dial. Transplant.*, 17:66-70.

Nimtz et al., (1993), "Structures of Sialylated Oligosaccharides of Human Erythropoietin Expressed in Recombinant BHK-21 Cells," *Eur. J. Biochem.*, 213:39-56.

Seidenfeld et al., (2001), "Epoetin Treatment of Anemia Associated with Cancer Therapy: a Systematic Review and Meta-analysis of Controlled Clinical Trials," *Journal of the National Cancer Institute*, 93:1204-1214.

Angal et al., (1993), "A Single Amino Acid Substitution Abolishes the Heterogeneity of Chimeric Mouse/Human (IgG4) Antibody," *Molecular Immunology*, 30(1):105-108.

Becker et al., (1996), "Long-lived and Transferable Tumor Immunity in Mice after Targeted Interleukin-2 Therapy," *J. Clin. Invest.*, 98(12):2801-2804.

Becker et al., (1996), "T Cell-mediated Eradication of Murine Metastatic Melanoma Induced by Targeted Interleukin-2 Therapy," *J. Exp. Med.*, 183(50):2361-2366.

Bitonti et al., (2002), "Transepithelial Absorption of an Erythropoietin-Fc Fusion Protein After Delivery to the Central Airways," *Respiratory Drug Delivery*, 8:309-312.

Boissel et al., (1993), "Erythropoietin Structure-Function Relationships: Mutant Proteins that Test a Model of Tertiary Structure," *The Journal of Biological Chemistry*, 268(21):15983-15993.

Briggs et al., (1974), "Hepatic Clearance of Intact and Desialylated Erythropoietin," *American Journal of Physiology*, 227(6):1385-1388.

Chuang et al., (1994), "Alteration of Lymphocyte Microtubule Assembly, Cytotoxicity, and Activation by the Anticancer Drug Taxol," *Cancer Research*, 54:1286-1291.

Darling et al., (2002), "Glycosylation of Erythropoietin Affects Receptor Binding Kinetics: Role of Electrostatic Interactions," *Biochemistry*, 41:14524-14531.

Davis et al., (2003), "Immunocytokines: Amplification of Anticancer Immunity," *Cancer Immunol. Immunother.*, 52:297-308.

Dolman et al., (1998), "Suppression of Human Prostate Carcinoma Metastases in Severe Combined Immunodeficient Mice by Interleukin 2 Immunocytokine Therapy," *Clin. Cancer Research.*, 4(10):2551-2557.

Duncan et al., (1988), "The Binding Site for C1q on IgG," *Nature*, 332:738-740.

Egrie et al., (2001), "Development and Characterization of Novel Erythropoiesis Stimulating Protein (NESP)," *Nephrol. Dial. Transplant.*, 16(Supp 3):3-13.

Elliott et al., (1997), "Mapping of the Active Site of Recombinant Human Erythropoietin," *Blood*, 89(2):493-502.

Frost et al., (1997), "A Phase I/IB Trial of Murine Monoclonal Anti-GD2 Antibody 14.G2a Plus Interleukin-2 in Children with Refractory Neuroblastoma," *Cancer*, 80(2):317-333.

Gan et al., (1999), "Specific Enzyme-linked Immunosorbent Assays for Quantitation of Antibody-cytokine Fusion Proteins," *Clinical and Diagnostic Laboratory Immunology*, 6(2):236-42.

Gillies et al., (1991), "Expression of Genetically Engineered Immunoconjugates of Lymphotoxin and a Chimeric Antiganglioside GD2 Antibody," *Hybridoma.*, 10(3):347-56.

Gillies et al., (2002), "Bi-functional Cytokine Fusion Proteins for Gene Therapy and Antibody-targeted Treatment of Cancer," *Cancer Immunol. Immunother.*, 51(8):449-60.

Gillies et al., (2002), "Improved Circulating Half-life and Efficacy of an Antibody-interleukin 2 Immunocytokine Based on Reduced Intracellular Proteolysis," *Clin. Cancer Research*, 8(1):210-216.

Greene et al., (1975), "Neuronal Properties of Hybrid Neuroblastoma X Sympathetic Ganglion Cells," *Proc. Natl. Acad. Sci. USA*, 72(12):4923-4927.

Hank et al., (1996), "Activation of Human Effector Cells by a Tumor Reactive Recombinant Anti-ganglioside GD2 Interleukin-2 Fusion Protein (ch14.18-IL2)," *Clin. Cancer Research*, 2(12):1951-1959.

Hank et al., (2003), "Determination of Peak Serum Levels and Immune Response to the Humanized Anti-ganglioside Antibody-interleukin-2 Immunocytokine," in *Methods in Molecular Medicine;* vol. 85: *Novel Anticancer Drug Protocols*, Buolamwini et al., (eds.), pp. 123-131, Humana Press Inc., Totowana, NJ.

Haraguchi, (1994), "Isolation of GD3 Synthase Gene by Expression Cloning of GM3 α-2,8-sialyltransferase cDNA using anti-GD2 Monoclonal Antibody," *Proc. Natl. Acad. Sci. USA*, 91(22):10455-10459.

Harris, (1995), "Processing of C-terminal Lysine and Arginine Residues of Proteins Isolated from Mammalian Cell Culture," *J. Chromatography A*, 705:129-134.

Hezareh et al., (2001), "Effector Function Activities of a Panel of Mutants of a Broadly Neutralizing Antibody against Human Immunodeficiency Virus Type 1," *J. Virology*, 75(24):12161-12168.

Idusogie et al., (2000), "Mapping of the C1q Binding Site on Rituxan, a Chimeric Antibody with a Human IgGI Fc," *J. Immunology*, 164(8):4178-4184.

Imboden et al., (2001), "The Level of MHC Class I Expression on Murine Adenocarcinoma Can Change the Antitumor Effector Mechanism of Immunocytokine Therapy," *Cancer Research*, 61(4):1500-7.

Kushner et al., (2001), "Phase II Trial of the Anti-GD2 Monoclonal Antibody 3F8 and Granulocyte-Macrophage Colony-Stimulating Factor for Neuroblastoma," *J. Clinical Oncology*, 19(22):4189-94.

Lode et al., (1997), "Targeted Interleukin-2 Therapy for Spontaneous Neuroblastoma Metastases to Bone Marrow," *J. Natl. Cancer Inst.*, 89(21):1586-94.

Lode et al., (2000), "What To Do With Targeted IL-2," *Drugs of Today*, 36(5):321-336.

Lode et al., (2000), "Melanoma Immunotherapy by Targeted IL-2 Depends on CD4(+) T-cell Help Mediated by CD40/CD40L Interaction," *J. Clin. Invest.*, 105(11):1623-30.

Metelitsa et al., (2002), "Antidisialoganglioside/granulocyte Macrophage-colony-stimulating Factor Fusion Protein Facilitates Neutrophil Antibody-dependent Cellular Cytotoxicity and Depends on FcγR11 (CD32) and Mac-1 (CD11b/CD18) for Enhanced Effector Cell Adhesion and Azurophil Granule Exocytosis," *Blood*, 99(11):4166-73.

Mueller et al., (1997), "Humanized Porcine VCAM-specific Monoclonal Antibodies with Chimeric IgG2/G4 Constant Regions Block Human Leukocyte Binding to Porcine Endothelial Cells," *Molecular Immunology*, 34(6):441-452.

Mullins et al., (1997), "Taxol-mediated Changes in Fibrosarcoma-induced Immune Cell Function: Modulation of Antitumor Activities," *Cancer Immunol. Immunother*, 45:20-28.

Naramura et al., (1994), "Mechanisms of Cellular Cytotoxicity Mediated by a Recombinant Antibody-IL2 Fusion Protein Against Human Melanoma Cells," *Immunology Letters*, 39:91-99.

Neal et al., (2003), "NXS2 Murine Neuroblastomas Express Increased Levels of MHC Class I Antigens upon Recurrence Following NK-dependent Immunotherapy," *Cancer Immunol. Immunother.*, 53:41-52.

Ngo et al., (1994), "Computational Complexity, Protein Structure Prediction, and the Levinthal Paradox," in *The Protein Folding Problem and Tertiary Structure Prediction*, Merz et al. (eds.), pp. 433-440 abd 492-495, Birkhauser, Boston, MA.

Niethammer et al., (2002) "An Oral DNA Vaccine Against Human Carcinoembryonic Antigen (CEA) Prevents Growth and Dissemination of Lewis Lung Carcinoma in CEA Transgenic Mice," *Vaccine*, 20:421-429.

Niethammer et al., (2001) "Targeted Interleukin 2 Therapy Enhances Protective Immunity Induced by an Autologous Oral DNA Vaccine against Murine Melanoma," *Cancer Research*, 61(16):6178-84.

Pancook et al., (1996), "Eradication of Established Hepatic Human Neuroblastoma Metastases in Mice with Severe Combined Immunodeficiency by Antibody-targeted Interleukin-2," *Cancer Immunol. Immunother.*, 42(2):88-92.

Park et al., (2000), "Efficiency of promoter and cell line in high-level expression of erythropoietin," *Biotechnol. Appl. Biochem.*, 32:167-172.

Reisfeld et al., (1996), "Antibody-interleukin 2 Fusion Proteins: A New Approach to Cancer Therapy," *J. Clin. Lab. Anal.*, 10:160-166.

Reisfeld et al., (1996), "Involvement of B Lymphocytes in the Growth Inhibition of Human Pulmonary Melanoma Metastases in Athymic *nu/nu* Mice by an Antibody-lymphotoxin Fusion Protein," *Cancer Research*, 56(8):1707-1712.

Ruehlmann et al., (2001), "MIG (CIXCL9) Chemokine Gene Therapy Combines with Antibody-cytokine Fusion Protein to Suppress Growth and Dissemination of Murine Colon Carcinoma," *Cancer Research*, 61(23):8498-503.

Sabzevari et al., (1994), "A Recombinant Antibody-interleukin 2 Fusion Protein Suppresses Growth of Hepatic Human Severe Combined Immunodeficiency Mice," *Proc. Natl. Acad. Sci. USA*, 91(20):9626-30.

Shinkawa et al., (2003), "The Absence of Fucose But Not the Presence of Galactose or Bisecting N-Acetylglucosamine of Human IgG1 Complex-type Oligosaccharides Shows the Critical Role of Enhancing Antibody-dependent Cellular Cytotoxicity," *J. Biol. Chem.*, 278:3466-3473.

Strom et al., (1996), "Therapeutic Approach to Organ Transplantation," Chapter 36, pp. 451-456, in *Therapeutic Immunology*, Austen et al., (eds.) Blackwell Science.

Thommesen et al., (2000), "Lysine 322 in the Human IgG3 CH2 Domain is Crucial for Antibody Dependent Complement Activation," *Mol. Immunol.*, 37(16):995-1004.

Wells, (1990), "Additivity of Mutational Effect in Proteins," *Biochemistry*, 29(37):8509-8517.

Xiang et al., (1998), "Induction of Persistent Tumor-protective Immunity in Mice Cured of Established Colon Carcinoma Metastases," *Cancer Research*, 58(17):3918-3925.

Xiang et al., (1999) "T Cell Memory against Colon Carcinoma is Long-lived in the Absence of Antigen," *J. Immunology*, 163(7):3676-83.

Xiang et al., (2001), "A Dual Function DNA Vaccine Encoding Carcinoembryonic Antigen and CD40 Ligand Trimer Induces T Cell-mediated Protective Immunity Against Colon Cancer in Carcinoembryonic Antigen-Transgenic Mice," *J. Immunology*, 167(8):4560-5.

Xiang et al., (2001), "Protective Immunity Against Human Carcinoembryonic Antigen (CEA) Induced by an Oral DNA Vaccine in CEA-transgenic Mice," *Clinical Cancer Research*, 7(3 Supp):S856-S864.

Yu et al., (1998), "Phase I Trial of a Human-Mouse Chimeric Anti-Disialoganglioside Monoclonal Antibody ch14.18 in Patients with Refractory Neuroblastoma and Osteosarcoma," *J. Clinical Oncology*, 16(6):2169-80.

Zagozdzon et al., (1999), "Potentiation of Antitumor Effects of IL-12 in Combination with Paclitaxel in Murine Melanoma Model *In Vivo*," *International Journal of Molecular Medicine*, 4:645-648.

Chapman et al., (1994), "Mapping Effector Functions of a Monoclonal Antibody to GD3 by Characterization of a Mouse-Human Chimeric Antibody," *Cancer Immuno. Immunother.*, 39:198-204.

Cruse et al., (eds.), (1995), *Illustrated Dictionary of Immunology*, p. 158, CRC Press, NY.

De la Salle et al., (1996), "FcγR on Human Dendritic Cells," in *Human IgG Receptors*, pp. 39-55, van de Winkel et al. (eds.), R.G. Landes Co.

Dorai et al., (1991), "Aglycosylated Chimeric Mouse/Human IgG1 Antibody Retains Some Effector Function," *Hybridoma*, 10(2):211-217.

Dorai et al., (1992), "Role of Inter-Heavy and Light Chain Disulfide Bonds in the Effector Functions of Human IgG1," *Molecular Immunology*, 29(12):1487-1491.

Elliott et al., (1996), "Fine-Structure Epitope Mapping of Antierythropoietin Monoclonal Antibodies Reveals a Model of Recombinant Human Erythropoietin Structure," *Blood*, 87(7):2702-2713.

Gillies et al., (1991), "Targeting Human Cytotoxic T Lymphocytes to Kill Heterologous Epidermal Growth Factor Receptor-Bearing Tumor Cells: Tumor-Infiltrating Lymphocyte/Hormone Receptor/Recombinant Antibody," *J. Immunology*, 146(3):1067-1071.

Handgretinger et al., (1995), "A Phase I Study of Human/Mouse Chimeric Anti-ganglioside GD2 Antibody ch14.18 in Patients with Neuroblastoma," *European J. Cancer*, 31A(2):261-267.

Hurn et al., (1980), "Production of Reagent Antibodies," *Methods in Enzymology*, 70: 104-142.

Isenman et al., (1975), "The Structure and Function of Immunoglobulin Domains: II. The Importance of Interchain Disulfide Bonds and the Possible Role of Molecular Flexibility in the Interaction between Immunoglobulin G and Complement," *J. Immunology*, 114(6):1726-1729.

Lo et al., (1992), "Expression and Secretion of an Assembled Tetrameric CH2-deleted Antibody in *E. coli.*," *Hum. Antibod. Hybridomas*, 3:123-128.

Maecker et al., (1997), "DNA Vaccination with Cytokine Fusion Constructs Biases the Immune Response to Ovalbumin," *Vaccine*, 15(15):1687-1696.

Mueller et al., (1990), "Enhancement of Antibody-Dependent Cytotoxicity With A Chimeric Anti-GD2 Antibody," *J. Immunology*, 144(4):1382-1386.

Mueller et al., (1990), "Serum Half-Life and Tumor Localization of a Chimeric Antibody Deleted of the CH2 Domain and Directed Against the Disialoganglioside GD2," *Proc. Natl. Acad. Sci. USA.*, 87:5702-5705.

Naramura et al., (1993), "Therapeutic Potential of Chimeric and Murine Anti-(Epidermal Growth Factor Receptor) Antibodies in a Metastasis Model for Human Melanoma," *Cancer Immuno. Immunother.*, 37:343-349.

Reisfeld et al., (1994), "Potential of Genetically Engineered Anti-Ganglioside GD2 Antibodies for Cancer Immunotherapy," *Prog. Brain Res.*, 101:201-212.

Saleh et al., (1992), "Phase I Trial of the Chimeric Anti-GD2 Monoclonal Antibody ch14.18 in Patients With Malignant Melanoma," *Hum. Antibod. Hybridomas*, 3:19-24.

Sallusto et al., (1994), "Efficient Presentation of Soluble Antigen by Cultured Human Dendritic Cells Is Maintained by Granulocyte/Macrophage Colony-stimulating Factor Plus Interleukin 4 and Downregulated by Tumor Necrosis Factor α," *J. Exp. Med.*, 179:1109-1118.

Schlom (1991), "Monoclonal Antibodies: They're More and Less Than You Think," in *Molecular Foundations of Oncology*, pp. 95-133.

Wen et al., (1994), "Erythropoietin Structure-Function Relationships: Identification of Functionally Important Domains," *J. Biological Chemistry*, 269(36):22839-22846.

Aichele et al., (1994), "Peptide-Induced T-Cell Tolerance to Prevent Autoimmune Diabetes in a Transgenic Mouse Model," *Proc. Natl. Acad. Sci. USA*, 91:444-448.

Altschul et al., (1990), "Basic Local Alignment Search Tool," *J. Mol. Biol.*, 215:403-10.

Altschul et al., (1997), "Gapped BLAST and PSI-BLAST: A New Generation of Protein Database Search Programs," *Nucleic Acids Res.*, 25(17):3389-3402.

Anderson et al., (1980), "Characterization of the Fc Receptor for IgG on a Human Macrophage Cell Line U937," *J. Immunol.*, 125(6):2735-41.

Anderson et al., (1994), "Effects of Route and Formulation on Clinical Pharmacokinetics of Interleukin-2," *Clin. Pharmacokinet.*, 27(1):19-31.

Baici et al., (1980), "Kinetics of the Different Susceptibilities of the Four Human Immunoglobulin G Subclasses to Proteolysis by Human Lysosomal Elastase," *Scand. J. Immunol.* 12(1):41-50.

Barbulescu et al., (1998), "IL-12 and IL-18 Differentially Regulate the Transcriptional Activity of the Human IFN-γ Promoter in Primary CD4+ T Lymphocytes," *J. Immunol.*, 160:3642-7.

Bednarek et al., (1991), "Soluble HLA-A2.1 Restricted Peptides that are Recognized by Influenza Virus Specific Cytotoxic T Lymphocytes," *J. Immunol. Methods*, 139:41-47.

Benacerraf et al., (1959), "The Clearance of Antigen Antibody Complexes from the Blood by the Reticulo-Endothelial System," *J. Immunol.*, 82:131-7.

Böhm, (1994), "On the Use of LUDI to Search the Fine Chemicals Directory for Ligands of Proteins of Known Three-Dimensional Structure," *J. Comput. Aided Mol. Des.*, 8:623-32.

Böhm, (1994), "The Development of a Simple Empirical Scoring Function to Estimate the Binding Constant for a Protein-Ligand Complex of Known Three-Dimensional Structure," *J. Comput. Aided Mol. Des.*, 8(3):243-56.

Böhm, (1998), "Prediction of Binding Constant of Protein Ligands: A Fast Method for the Prioritization of Hits Obtained from De Novo Design or 3D Database Search Programs," *J. Comput. Aided Mol. Des.*, 12(4):309-23.

Boshart et al., (1985), "A Very Strong Enhancer is Located Upstream of an Immediate Early Gene of Human Cytomegalovirus," *Cell*, 41:521-530.

Boulianne et al., (1984), "Production of Functional Chimaeric Mouse/Human Antibody," *Nature*, 312:643-6.

Bourgois et al., (1974), "Determination of the Primary Structure of a Mouse IgG2a Immunoglobulin Amino Acid Sequence of the Fc Fragment: Implications for the Evolution of Immunoglobulin Structure and Function," *Eur. J. Biochem.*, 43:423-35.

Brambell et al., (1964), "A Theoretical Model of γ-Globulin Catabolism," *Nature*, 203:1352-55.

Brazolot Millan et al., (1998), "Cpg DNA Can Induce Strong THl Humoral and Cell-Mediated Immune Responses against Hepatitis B Surface Antigen in Young Mice," *Proc. Natl. Acad. Sci. USA*, 95:15553-8.

Brekke et al., (1994), "Human IgG Isotype-Specific Amino Acid Residues Affecting Complement-Mediated Cell Lysis and Phagocytosis," *Eur. J. Immunol.*, 24:2542-2547.

Brem et al., (1993), "The Combination of Antiangiogenic Agents to Inhibit Primary Tumor Growth and Metastasis," *J. Pediatr. Surg.*, 28(10):1253-7.

Brooks et al., (1983), "CHARMM: A Program for Macromolecular Energy Minimization and Dynamics Calculations," *J. Comput. Chemistry*, 4:187-217.

Broudy et al., (1988), "Recombinant Human Erythropoietin: Purification and Analysis of Carbohydrate Linkage," *Arch. Biochem. Biophys.*, 265:329-36.

Bubenik et al., (1995), "Interleukin-2 Gene Therapy of Residual EL-4 Leukaemia Potentiates the Effect of Cyclophosphamide Pretreatment," *J. Cancer Res. Clin. Oncol.*, 121:39-43.

Bumol et al., (1982), "Unique Glycoprotein-Proteoglycan Complex Defined by Monoclonal Antibody on Human Melanoma Cells," *Proc. Natl. Acad. Sci. USA*, 79:1245-9.

Carnemolla et al., (1989), "A Tumor-Associated Fibronectin Isoform Generated by Alternative Splicing of Messenger RNA Precursors," *J. Cell. Biol.*, 108:1139-1148.

Carnemolla et al., (1992), "The Inclusion of the Type III Repeat ED-B in the Fibronectin Molecule Generates Conformational Modifications that Unmask a Cryptic Sequence," *J. Biol. Chem.*, 267(34):24689-24692.

Cazzola et al., (1998), "Red Blood Cell Precursor Mass as an Independent Determinant of Serum Erythropoietin Level," *Blood*, 91:2139-45.

Chan et al., (1992), "Mechanisms of IFN-γ Induction by Natural Killer Cell Stimulatory Factor (NKSF/IL-12). Role of Transcription and mRNA Stability in the Synergistic Interaction Between NKSF and IL-2," *J. Immunol.*, 148:92-98.

Chappel et al., (1991), "Identification of the Fc Gamma Receptor Class I Binding Site In Human IgG Through Use of Recombinant IgG1/IgG2 Hybrid and Point-Mutated Antibodies," *Proc. Natl. Acad. Sci. USA*, 88(20):9036-40.

Cheetham, (1998), "NMR Structure of Human Erythropoietin and a Comparison with its Receptor Bound Conformation," *Nat. Struct. Biol.*, 5:861-6.

Ciardiello et al., (1996), "Antitumor Activity of Combined Blockade of Epidermal Growth Factor Receptor and Protein Kinase A," *J. Natl. Cancer Inst.*, 88:1770-6.

Cirulli et al., (1998), "KSA Antigen Ep-CAM Mediates Cell-Cell Adhesion of Pancreatic Epithelial Cells: Morphoregulatory Roles in Pancreatic Islet Development," *J. Cell Biol.*, 140:1519-34.

Cohen et al., (1998), "An Artificial Cell-Cycle Inhibitor Isolated from a Combinatorial Library," *Proc. Natl. Acad. Sci. USA*, 95:14272-7.

Congote et al., (1984), The Erthrotropins, New Erythroid Cell Stimulate Factors Extracted From Human and Bovine Fetal Tissues, Abstract 364, "Proceedings 7th Intl. Congress of Endocrinology," Quebec City, Quebec, Jul. 1-7, 1984.

Congote, (1983), "Isolation of Two Biologically Active Peptides, Erythrotropin I and Erythrotropin II from Fetal Calf Intestine," *Biochem. Biophys. Res. Commun.*, 115(2):477-83.

Congote, (1984), "Extraction from Fetal Bovine Serum of Erythrotropin, an Erythroid Cell-Stimulating Factor," *Anal. Biochem.*, 140:428-33.

Connor et al., (2004), "Ex vivo Evaluation of Anti-EpCAM Immunocytokine huKS-IL2 in Ovarian Cancer," *Immunotherapy*, 27:211-219.

Cosenza et al., (1997), "Disulfide Bond Assignment in Human Interleukin-7 by Matrix-Assisted Laser Desorption/Ionization Mass Spectroscopy and Site-Directed Cysteine to Serine Mutational Analysis," *J. Biol. Chem.*, 272:32995-3000.

Cunningham et al., (1989), "High-Resolution Epitope Mapping of hGH-Receptor Interactions by Alanine-Scanning Mutagenesis," *Science*, 244:1081-85.

Curiel et al., (1991), "Adenovirus Enhancement of Transferrin-Polylysine-Mediated Gene Delivery," *Proc. Natl. Acad. Sci. USA*, 88:8850-4.

Dauber-Osguthorpe et al., (1988), "Structure and Energetics of Ligand Binding to Proteins: *Escherichia coli* Dihydrofolate Reductase-Trimethoprim, A Drug-Receptor System," *Proteins*, 4:31-47.

Daugherty et al., (1991), "Polymerase Chain Reaction Facilities the Cloning, CDR-Grafting, and Rapid Expression of a Murine Monoclonal Antibody Directed Against the CD18 Component of Leukocyte Integrins," *Nucleic Acid Res.*, 19:2471-2476.

De Bruijn et al., (1995), "Phagocyte-Induced Antigen-Specific Activation of Unprimed CD8+ T Cells in Vitro," *Eur. J. Immunol.*, 25:1274-85.

Delorme et al., (1992), "Role of Glycosylation on the Secretion and Biological Activity of Erythropoietin," *Biochemistry*, 31:9871-6.

Desai et al., (1992), "IL-12 Receptor. II. Distribution and Regulation of Receptor Expression," *J. Immunol.*, 148:3125-32.

Donnelly et al., (1993), "Targeted Delivery of Peptide Epitopes to Class I Major Histocompatibility Molecules by a Modified Pseudomonas Exotoxin," *Proc. Natl. Acad. Sci. USA*, 90:3530-4.

Donnelly et al., (1997), "DNA Vaccines," *Annu. Rev. Immunol.*, 15:617-48.

Dube et al., (1988), "Glycosylation at Specific Sites of Erythropoietin is Essential for Biosynthesis, Secretion, and Biological Function," *J. Biol. Chem.*, 263:17516-21.

Ellison et al., (1982), "The Nucleotide Sequence of a Human Immunoglobulin C $\gamma_1$ Gene," *Nucleic Acids Res.*, 10:4071-9.

Faas et al., (1993), "Phenotypically Diverse Mouse Thymic Stromal Cell Lines which Induce Proliferation and Differentiation Of Hematopoietic Cells," *Eur. J. Immunol.*, 23:1201-14.

Farner et al., (1995), "Distinction Between $\gamma_c$ C Detection and Function in YT Lymphoid Cells and in the Granulocyte-Macrophage Colony-Stimulating Factor-Responsive Human Myeloid Cell Line, Tf-1," *Blood*, 86:4568-78.

Fawell et al., (1994), "Tat-Mediated Delivery of Heterologous Proteins into Cells," *Proc. Natl. Acad. Sci. USA*, 91:664-8.

Fu et al., (1993), "The Sheep Erythropoietin Gene: Molecular Cloning and Effect of Hemorrhage on Plasma Erythropoietin and Renal/Liver Messenger RNA in Adult Sheep," *Mol. Cell. Endocrinol.*, 93:107-16.

Gainsford et al., (1996), "Leptin Can Induce Proliferation, Differentiation, and Functional Activation of Hemopoietic Cells," *Proc. Natl. Acad. Sci. USA*, 93:14564-14568.

Gammon et al., (1992), "Endogenous Loading of HLA-A2 Molecules with an Analog of the Influenza Virus Matrix Protein-Derived Peptide and Its Inhibition By An Exogenous Peptide Antagonist," *J. Immunol.*, 148:7-12.

Ghetie et al., (1990), "Disseminated or Localized Growth of a Human B-Cell Tumor (Daudi) in SCID Mice," *Intl. J. Cancer*, 45:485.

Ghetie et al., (1997), "FcRn: The MHC Class I-Related Receptor that is More Than an IgG Transporter," *Immunology Today*, 18(12):592-598.

Goldwasser et al., (1971), "Purification of Erythropoietin," *Proc. Natl. Acad. Sci. USA*, 68:697-8.

Goldwasser et al., (1975), "Erythropoeitin: Assay and Study of its Mode of Action," *Methods Enzymol.*, 37(PtB):109-21.

Gurewich et al., (1988), "Characterization of the Intrinsic Fibrinolytic Properties of Pro-Urokinase Through a Study of Plasmin-Resistant Mutant Forms Produced by Site-Specific Mutagenesis of Lysine," *J. Clin. Invest.*, 82:1956-1962.

Hashimoto et al., (1999), "Differential Antitumor Effects of Administration of Recombinant IL-18 or Recombinant IL-12 are Mediated Primarily by Fas-Fas Ligand- and Perforin-Induced Tumor Apoptosis, Respectively," *J. Immunol.*, 163:583-9.

Henikoff et al., (1992), "Amino Acid Substitution Matrices from Protein Blocks," *Proc. Natl. Acad. Sci. USA*, 89:10915-10919.

Hilgers et al., (1999), "Sulfolipo-Cyclodextrin in Squalane-In-Water as a Novel and Safe Vaccine Adjuvant," *Vaccine*, 17:219-28.

Hori et al., (1987), "Establishment of an Interleukin 2-Dependent Human T Cell Line from a Patient with T Cell Chronic Lymphocytic Leukemia Who is Not Infected with Human T Cell Leukemia/Lymphoma Virus," *Blood*, 70:1069-72.

Hulett et al., (1994), "Molecular Basis of Fc Receptor Function," *Adv. Immunol.*, 57:1127.

Huston et al., (1988), "Protein Engineering of Antibody Binding Sites: Recovery of Specific Activity in an Anti-Digoxin Single-Chain Fv Analogue Produced In *Escherichia coli*," *Proc. Natl. Acad. Sci. USA*, 85:5879-5883.

Jacobs et al., (1985), "Isolation and Characterization of Genomic And cDNA Clones of Human Erythropoietin," *Nature*, 313:806-10.

Jefferis et al., (1990), "Molcular Definition of Interaction Sites on Human IgG for Fc Receptors huFcγR," *Mol. Immunol.*, 27(12):1237-1240.

Karlin et al., (1990), "Methods for Assesing the Statistical Significance of Molecular Sequence Features by Using General Scoring Schemes," *Proc. Natl. Acad. Sci. USA*, 87:2264-8.

Karlin et al., (1993), "Applications and Statistics for Multiple High-Scoring Segments in Molecular Sequences," *Proc. Natl. Acad. Sci. USA*, 90:5873-7.

Karpusas et al., (1997), "The Crystal Structure of Human Interferon β at 2.2-A Resolution," *Proc. Natl. Acad. Sci. USA*, 94:11813-11818.

Kelner et al., (1994), "Lymphotactin: A Cytokine that Represents a New Class of Chemokine," *Science*, 266:1395-9.

Kirkman et al., (1989), "Prolongation of Cardiac Allograft Survival in Murine Recipients Treated with a Diphtheria Toxin-Related Interleukin-2 Fusion Protein," *Transplantation*, 47(2):327-330.

King et al., (2004), "Phase I Clinical Trial of the Immunocytokine EMD 273063 in Melanoma Patients," *J. Clin. Oncol.*, 22(22):4463-73.

Klinman et al., (1997), "Contribution of CpG Motifs to the Immunogenicity of DNA Vaccines," *J. Immunol.*, 158:3635-9.

Ko et al., (2004), "Safety, Pharmacokinetics, and Biological Pharmacodynamics of the Immunocytokine EMD 273066 (huKS-IL2)," *J. Immunotherapy*, 27:232-239.

Kuntz et al., (1982), "A Geometric Approach to Macromolecule-Ligand Interactions," *J. Mol. Biol.*, 161:269-88.

Kurtz, (1982), "A New Candidate for the Regulation of Erythropoiesis. Insulin-Like Growth Factor I," *FEBLAL.*, 149(1):105-8.

Lai et al., (1986), "Structural Characterization of Human Erythropoietin," *J. Biol. Chem.*, 261:3116-21.

Lai et al., (1998), "DNA Vaccines," *Crit. Rev. Immunol.*, 18:449-84.

Lanza et al., (1993), "Active Immunity against the CD4 Receptor by Using an Antibody Antigenized with Residues 41-55 of the First Extracellular Domain," *Proc. Natl. Acad. Sci. USA*, 90:11683-7.

Lawn et al., (1981), "DNA Sequence of a Major Human Leukocyte Interferon Gene," *Proc. Natl. Acad. Sci. USA*, 78:5435-9.

Lin et al., (1985), "Cloning and Expression of the Human Erythropoietin Gene," *Proc. Natl. Acad. Sci. USA*, 82:7580-4.

Lin et al., (1986), "Monkey Erythropoietin Gene: Cloning, Expression and Comparison with the Human Erythropoietin Gene," *Gene*, 44:201-9.

Lode et al., (1998), "Gene Therapy with a Single Chain Interleukin 12 Fusion Protein Induces T Cell-Dependent Protective Immunity in a Syngeneic Model of Murine Neuroblastoma," *Proc. Natl. Acad. Sci. USA*, 95:2475-80.

Lorenz et al., (1999), "Induction of Anti-Tumor Immunity Elicited by Tumor Cells Expressing a Murine LFA-3 Analog Via a Recombinant Vaccinia Virus," *Hum. Gene Ther.*, 10:623-31.

Lotze et al., (1996), "Cytokine Gene Therapy of Cancer Using Interleukin-12: Murine and Clinical Trials," *Ann. NY Acad. Sci.*, 795:440-54.

MacLean et al., (1996), "Enhancing the Effect of Theratope STn-KLH Cancer Vaccine in Patients with Metastatic Breast Cancer by Pretreatment with Low-Dose Intravenous Cyclophosphamide," *J. Immunother.*, 19(4):309-316.

Maghazachi et al., (1997), "Interferon-Inducible Protein-10 and Lymphotactin Induce the Chemotaxis and Mobilization of Intracellular Calcium in Natural Killer Cells through Pertussis Toxin-Sensitive and -Insensitive Heterotrimeric G-Proteins," *FASEB J.*, 11:765-74.

Mariani et al., (1997), "Tumor Targeting Potential of the Monoclonal Antibody BC-1 against Oncofetal Fibronectin in Nude Mice Bearing Human Tumor Implants," *Cancer*, 80:2378-84.

Marshall et al., (1994), "Role of the Polymorphic Residues in HLA-DR Molecules in Allele-Specific Binding of Peptide Ligands," *J. Immunol.*, 152:4946-57.

Marshall et al., (1995), "Prediction of Peptide Affinity to HLA-DR Molecules," *Biomed. Pept. Proteins Nucleic Acids*, 1(3):157-62.

McDonald, (1986), "Cloning, Sequencing, and Evolutionary Analysis of the Mouse Erythropoietin Gene," *Mol. Cell. Biol.*, 6:842-8.

McGonigle et al., (1984), "Erythropoietin Deficiency and Inhibition of Erythropoiesis in Renal Insufficiency," *Kidney Int.*, 25(2):437-44.

McMahan et al., (1991), "A Novel IL-1 Receptor, Cloned From B-Cells by Mammalian Expression is Expressed in Many Cell Types," *EMBO J.*, 10:2821-32.

McMahon et al., (1990), "Pharmacokinetics and Effects of Recombinant Human Erythropoietin after Intravenous and Subcutaneous Injections in Healthy Volunteers," *Blood*, 76:1718-22.

Mehrotra et al., (1993), "Effects of IL-12 on the Generation of Cytotoxic Activity in Human CD8+ T Lymphocytes," *J. Immunol.*, 151:2444-52.

Menard et al., (1983), "Generation of Monoclonal Antibodies Reacting with Normal and Cancer Cells of Human Breast," *Cancer Res.*, 43:1295-300.

Miyake et al., (1977), "Purification of Human Erythropoietin," *J. Biol. Chem.*, 252:5558-64.

Miyake et al., (1988), "Synthesis of Recombinant Human Single-Chain Urokinase-Type Plasminogen Activator Variants Resistant to Plasmin and Thrombin," *J. Biochem.*, 104:643-647.

Morrison et al., (1984), "Chimeric Human Antibody Molecules: Mouse Antigen-Binding Domains with Human Constant Region Domains," *Proc. Natl. Acad. Sci. USA*, 81:6851-5.

Nagao et al., (1992), "Nucleotide Sequence of Rat Erythropoietin," *Biochim. Biophys. Acta*, 1171(1):99-102.

Nastala et al., (1994), "Recombinant IL-12 Administration Induces Tumor Regression in Association with IFN-$\gamma$ Production," *J. Immunol.*, 153:1697-706.

Naughton et al., (1983), "Evidence for an Erythropoietin-Stimulating Factor in Patients with Renal and Hepatic Disease," *Acta. Haemat.*, 69:171-9.

Neal et al., (2004), "Enhanced Activity of Hu14.18-IL2 Immunocytokine against Murine NXS2 Neuroblastoma when Combined with Interleukin-2 Therapy," *Clin. Cancer. Res.*, 10:4839-4847.

Nelles et al., (1987), "Characterization of Recombinant Human Single Chain Urokinase-Type Plaminogen Activtor Mutants Produced by Site-Specific Mutagenesis of Lysine 158," *J. Biol. Chem.*, 262(12):5682-5689.

Noguchi et al., (1994), "A Mouse Mutant P53 Product Recognized by CD4+ and CD8+ T Cells," *Proc. Natl. Acad. Sci. USA*, 91:3171-5.

Orlandi et al., (1989), "Cloning Immunoglobulin Variable Domains for Expression by the Polymerase Chain Reaction," *Proc. Natl. Acad. Sci. USA*, 86:3833-7.

Palmer et al., (2001), "Phase I Study of the BLP 25 (MUC1 Peptide) Liposomal Vaccine for Active Specific Immunotherapy in Stage IIIB/IV Non-Small-Cell Lung Cancer," *Clinical Lung Cancer*, 3(1):49-57.

Palucka et al., (1998), "Dendritic Cells as the Terminal Stage of Monocyte Differentiation," *J. Immunol.*, 160:4587-95.

Panina-Bordignon et al., (1989), "Universally Immunogenic T Cell Epitopes: Promiscuous Binding to Human MHC Class II and Promiscuous *Recognition* by T Cells," *Eur. J. Immunol.*, 19:2237-42.

Pavlović-Kentera et al., (1980), "Effects of Prostaglandin Synthetase Inhibitors, Salt Overload and Renomedullary Dissection on the Hypoxia Stimulated Erythropoietin Production in Rats," *Exp. Hematol.*, 8(Supp. 8):283-92.

Pedley et al. (1999), "Enhancement of Antibody-Directed Enzyme Prodrug Therapy in Colorectal Xenografts by an Antivascular Agent," *Cancer Res.*, 59:3998-4003.

Perussia et al., (1992), "Natural Killer (NK) Cell Stimulatory Factor or IL-12 Has Differential Effects on the Proliferation of TCR-$\alpha\beta$+, TCR-$\gamma\delta$+ T Lymphocytes, and NK Cells," *J. Immunol.*, 149:3495-502.

Pluschke et al., (1996), "Molecular Cloning of a Human Melanoma-Associated Chondroitin Sulfate Proteoglycan," *Proc. Natl. Acad. Sci. USA*, 93:9710-5.

Poon et al., (1995), "Structure and Function of Several Anti-Dansyl Chimeric Antibodies Formed by Domain Interchanges Between Human IgM and Mouse IgG2b," *J. Biol. Chem.*, 270:8571-7.

Queen et al., (1989), "A Humanized Antibody that Binds to the Interleukin 2 Receptor," *Proc. Natl. Acad. Sci. USA*, 86:10029-33.

Radhakrishnan et al., (1996), "Zinc Mediated Dimer of Human Interferon-$\alpha_{2b}$ Revealed by X-Ray Crystallography," *Structure* 4(12):1453-63.

Ramachandran et al., (1968)"Conformation of Polypeptides and Proteins," *Adv. Prot. Chem.*, 23:283-294.

Rarey et al., (1995), "Time-Efficient Docking of Flexible Ligands into Active Sites Of Proteins," *Proc. Int. Conf. Intell. Syst. Mol. Biol.* 3:300-8.

Resegotti et al., (1981), "Treatment of Aplastic Anaemia with Methenolone, Stanozolol and Nandrolone. A Report of 130 Cases," *Pan. Med.*, 23:243-8.

Riechmann et al., (1988), "Reshaping Human Antibodies for Therapy," *Nature*, 332:323-7.

Robinson et al., (1998), "Optimizing the Stability of Single-Chain Proteins by Linker Length and Composition Mutagenesis," *Proc. Natl. Acad. Sci. USA*, 95:5929-34.

Rothmann et al., (1982), "Erythropoietin-Dependent Erythrocytosis associated with Hepatic Angiosarcoma," *J. Surg. Oncol.*, 20:105-8.

Runkel et al., (1998), "Structural and Functional Differences Between Glycosylated and Non-Glycosylated Forms of Human Interferon-$\beta$ (IFN-$\beta$)," *Pharmaceutical Res.*, 15:641-649.

Sakano et al., (1980), "Two Types of Somatic Recombination are Necessary for the Generation of Complete Immunoglobin Heavy-Chain Genes," *Nature*, 286:676-683.

Sāli et al., (1993), "Comparative Protein Modelling by Satisfaction of Spatial Restraints," *J. Mol. Biol.*, 234:779-815.

Schecter et al., (1997), "Tissue Factor is Induced by Monocyte Chemoattractant Protein-1 in Human Aortic Smooth Muscle And THP-1 Cells," *J. Biol. Chem.*, 272:28568-73.

Senior et al., (2000), "Cleavage of a Recombinant Human Immunoglobulin A2 (igA2)-IgA1 Hybrid Antibody by Certain Bacterial IgA1 Proteases," *Infect. Immun.*, 68(2):463-9.

Sharp et al., (1988), "Codon Usage Patterns in *Escherichia coli*, *Bacillus subtilis*, *Saccharomyces cerevisiae*, *Schizosaccharomyces pombe*, *Drosophila melanogaster* and *Homo sapiens*; a Review of the Consdierable Within-Species Diversity," *Nucleic Acids Res.*, 16(17):8207-8211.

Simonsen et al., (1983), "Isolation and Expression of an Altered Mouse Dihydrofolate Reductase cDNA," *Proc. Natl. Acad. Sci. USA*, 80:2495-2499.

Smith et al., (1981), "Identification of Common Molecular Subsequences," *J. Mol. Biol.*, 147:195-197.

Soligo et al., (1998), "Expansion of Dendritic Cells Derived from Human CD34+ Cells in Static And Continuous Perfusion Cultures," *Br. J. Haematol.*, 101:352-63.

Spivak et al., (1989), "The In Vivo Metabolism of Recombinant Human Erythropoietin in The Rat," *Blood*, 73:90-9.

Sturniolo et al., (1999), "Generation of Tissue-Specific and Promiscuous HLA Ligand Databases Using DNA Microarrays and Virtual HLA Class II Matrices," *Nat. Biotech.*, 17(6):555-61.

Suliman et al., (1996), "Cloning of a cDNA Encoding Bovine Erythropoietin and Analysis of Its Transcription in Selected Tissues," *Gene*, 171:275-80.

Takahashi et al., (2000), "Immunologic Self-Tolerance Maintained by CD25+ CD4+ Regulatory T Cells Constitutively Expressing Cytotoxic T Lymphocyte-Associated Antigen 4," *J. Exp. Med.*, 192(2):303-309.

Taniguchi et al., (1980), "Expression of the Human Fibroblast Interferon Gene in *Escherichia coli,*" *Proc. Natl. Acad. Sci. USA*, 77:5230-5233.

Thurner, (1999), "Generation of Large Numbers of Fully Mature and Stable Dendritic Cells from Leukapheresis Products for Clinical Application," *J. Immunol. Methods*, 223:1-15.

Tiruppathi et al., (1996), "Isolation and Characterization of a Cell Surface Albumin-Binding Protein from Vascular Endothelial Cells," *Proc. Nat. Acad. Sci. USA*, 93:250-4.

van Den Eynde et al., (1989), "Presence on a Human Melanoma of Multiple Antigens Recognized By Autologous CTL," *Int. J. Cancer*, 44:634-40.

Van Der Bruggen et al., (1991), "A Gene Encoding and Antigen Recognized by Cytolytic T Lymphocytes on a Human Melanoma," *Science*, 254:1643-7.

Van Heyningen et al., (1982), "Human MHC Class II Molecules as Differentiation Markers," *Immunogenetics*, 16:459-69.

Voest et al., (1995), "Inhibition of Angiogenesis in Vivo by Interleukin 12," *J. Natl. Canc. Inst.*, 87:581-6.

Von Heijne et al., (1986), "A New Method for Predicting Signal Sequence Cleavage Sites," *Nucleic Acid Res.*, 14:4683-4690.

Ward et al., (1995), "The Effector Functions of Immunoglobulins: Implications for Therapy," *Therapeutic. Immunology*, 2:77-94.

Watson et al., (1984), "Compilation of Published Signal Sequences," *Nucleic Acid Res.*, 12:5145-5164.

Weitkamp et al., (1973), "Additional Data on the Population Distribution of Human Serum Albumin Genes; Three New Variants," *Ann. Hum. Genet.*, 37:219-26.

Woof et al., (1986), "Localisation of the Monocyte-Binding Region on Human Immunoglobulin G," *Mol. Immunol.*, 23:319-30.

Wyatt et al., (1998), "The Antigenic Structure of the HIV gp120 Envelope Glycoprotein," *Nature*, 393:705-11.

Wysocka et al., (1995), "Interleukin-12 is Required for Interferon-γ Production and Lethality in Lipopolysaccharide-Induced Shock in Mice," *Eur. J. Immunol.*, 25:672-6.

Yan et al., (1996), "Characterization of an Ig VH Idiotope that Results in Specific Homophilic Binding and Increased Avidity for Antigen," *J. Immunol.*, 157:1582-8.

Yeh et al., (1992), "Design of Yeast-Secreted Albumin Derivatives for Human Therapy: Biological and Antiviral Properties of a Serum Albumin-CD4 Genetic Conjugate," *Proc. Natl. Acad. Sci. USA*, 89:1904-8.

Zhang et al., (1994), "Structure/Activity Analysis of Human Monocyte Chemoattractant Protein-1 (MCP-1) by Mutagenesis," *J. Biol. Chem.*, 269:15918-24.

Zuckier et al., (1998), "Chimeric Human-Mouse IgG Antibodies with Shuffled Constant Region Exons Demonstrate that Multiple Domains Contribute to In Vivo Half-Life," *Cancer Res.*, 58(17):3905-8.

* cited by examiner

SEQUENCE LISTING

<160> NUMBER OF SEQ ID NOS: 29

<210> SEQ ID NO 1
<211> LENGTH: 514
<212> TYPE: DNA
<213> ORGANISM: Homo sapiens

```
<220> FEATURE:
<221> NAME/KEY: CDS
<222> LOCATION: (8)..(505)
<223> OTHER INFORMATION: Human EPO, DNA sequence modified but no change
      in protein sequence

<400> SEQUENCE: 1 cccgggt gcc cca cca cgc ctc atc tgt gac agc cga gtg ctg gag agg         49
        Ala Pro Pro Arg Leu Ile Cys Asp Ser Arg Val Leu Glu Arg
        1               5                   10 tac ctc ttg gag gcc aag gag gcc gag aat atc acg acc ggc tgt gct         97
Tyr Leu Leu Glu Ala Lys Glu Ala Glu Asn Ile Thr Thr Gly Cys Ala
15              20                  25                  30 gaa cac tgc agc ttg aat gag aac atc acc gtg cct gac acc aaa gtg        145
Glu His Cys Ser Leu Asn Glu Asn Ile Thr Val Pro Asp Thr Lys Val
                35                  40                  45 aat ttc tat gcc tgg aag agg atg gag gtt ggc cag cag gcc gta gaa        193
Asn Phe Tyr Ala Trp Lys Arg Met Glu Val Gly Gln Gln Ala Val Glu
            50                  55                  60 gtg tgg cag ggc ctg gcc ctg ctg tcg gaa gct gtc ctg cgg ggc cag        241
Val Trp Gln Gly Leu Ala Leu Leu Ser Glu Ala Val Leu Arg Gly Gln
65                  70                  75 gcc ctg ttg gtc aac tct tcc cag ccg tgg gag ccc ctg caa ctg cat        289
Ala Leu Leu Val Asn Ser Ser Gln Pro Trp Glu Pro Leu Gln Leu His
    80                  85                  90 gtg gat aaa gcc gtg agt ggc ctt cgc agc ctc acc act ctg ctt cgg        337
Val Asp Lys Ala Val Ser Gly Leu Arg Ser Leu Thr Thr Leu Leu Arg
95                  100                 105                 110 gct ctg gga gcc cag aag gaa gcc atc tcc cct cca gat gcg gcc tca        385
Ala Leu Gly Ala Gln Lys Glu Ala Ile Ser Pro Pro Asp Ala Ala Ser
                115                 120                 125 gct gct ccc ctc cgc aca atc act gct gac act ttc cgc aaa ctc ttc        433
Ala Ala Pro Leu Arg Thr Ile Thr Ala Asp Thr Phe Arg Lys Leu Phe
            130                 135                 140 cga gtc tac tcc aat ttc ctc cgg gga aag ctg aag ctg tac aca ggg        481
Arg Val Tyr Ser Asn Phe Leu Arg Gly Lys Leu Lys Leu Tyr Thr Gly
        145                 150                 155 gag gcc tgc cgg aca ggg gac aga tgactcgag                              514
Glu Ala Cys Arg Thr Gly Asp Arg
    160                 165

<210> SEQ ID NO 2
<211> LENGTH: 166
<212> TYPE: PRT
<213> ORGANISM: Homo sapiens

<400> SEQUENCE: 2

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
```

```
              100                 105                 110
Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 3
<211> LENGTH: 52
<212> TYPE: DNA
<213> ORGANISM: Artificial Sequence
<220> FEATURE:
<223> OTHER INFORMATION: Description of Artificial Sequence: Oligo1

<400> SEQUENCE: 3
ccgggtgccc caccacgcct catctgtgac agccgagtgc tggagaggta cc         52

<210> SEQ ID NO 4
<211> LENGTH: 49
<212> TYPE: DNA
<213> ORGANISM: Artificial Sequence
<220> FEATURE:
<223> OTHER INFORMATION: Description of Artificial Sequence: Oligo2

<400> SEQUENCE: 4
tcttggaggc caaggaggcc gagaatatca cgaccggctg tgctgaaca             49

<210> SEQ ID NO 5
<211> LENGTH: 52
<212> TYPE: DNA
<213> ORGANISM: Artificial Sequence
<220> FEATURE:
<223> OTHER INFORMATION: Description of Artificial Sequence: Oligo3

<400> SEQUENCE: 5
ctgcagcttg aatgagaaca tcaccgtgcc tgacaccaaa gtgaatttct at         52

<210> SEQ ID NO 6
<211> LENGTH: 48
<212> TYPE: DNA
<213> ORGANISM: Artificial Sequence
<220> FEATURE:
<223> OTHER INFORMATION: Description of Artificial Sequence: Oligo4

<400> SEQUENCE: 6
gcctggaaga ggatggaggt tggccagcag gccgtagaag tgtggcag              48

<210> SEQ ID NO 7
<211> LENGTH: 51
<212> TYPE: DNA
<213> ORGANISM: Artificial Sequence
<220> FEATURE:
<223> OTHER INFORMATION: Description of Artificial Sequence: Oligo5

<400> SEQUENCE: 7
ggcctggccc tgctgtcgga agctgtcctg cggggccagg ccctgttggt c          51

<210> SEQ ID NO 8
<211> LENGTH: 49
<212> TYPE: DNA
<213> ORGANISM: Artificial Sequence
```

```
<220> FEATURE:
<223> OTHER INFORMATION: Description of Artificial Sequence: Oligo6

<400> SEQUENCE: 8
aactcttccc agccgtggga gcccctgcaa ctgcatgtgg ataaagccg            49

<210> SEQ ID NO 9
<211> LENGTH: 52
<212> TYPE: DNA
<213> ORGANISM: Artificial Sequence
<220> FEATURE:
<223> OTHER INFORMATION: Description of Artificial Sequence: Oligo7

<400> SEQUENCE: 9
tgagtggcct cgcagcctc accactctgc ttcgggctct gggagcccag aa         52

<210> SEQ ID NO 10
<211> LENGTH: 48
<212> TYPE: DNA
<213> ORGANISM: Artificial Sequence
<220> FEATURE:
<223> OTHER INFORMATION: Description of Artificial Sequence: Oligo8

<400> SEQUENCE: 10
ggaagccatc tcccctccag atgcggcctc agctgctccc ctccgcac             48

<210> SEQ ID NO 11
<211> LENGTH: 53
<212> TYPE: DNA
<213> ORGANISM: Artificial Sequence
<220> FEATURE:
<223> OTHER INFORMATION: Description of Artificial Sequence: Oligo9

<400> SEQUENCE: 11
aatcactgct gacactttcc gcaaactctt ccgagtctac tccaatttcc tcc       53

<210> SEQ ID NO 12
<211> LENGTH: 59
<212> TYPE: DNA
<213> ORGANISM: Artificial Sequence
<220> FEATURE:
<223> OTHER INFORMATION: Description of Artificial Sequence: Oligo10

<400> SEQUENCE: 12
ggggaaagct gaagctgtac acaggggagg cctgccggac aggggacaga tgactcgag   59

<210> SEQ ID NO 13
<211> LENGTH: 49
<212> TYPE: DNA
<213> ORGANISM: Artificial Sequence
<220> FEATURE:
<223> OTHER INFORMATION: Description of Artificial Sequence: Oligo11

<400> SEQUENCE: 13
tcttggaggc caaggaggcc gagcagatca cgaccggctg tgctgaaca            49

<210> SEQ ID NO 14
<211> LENGTH: 52
<212> TYPE: DNA
<213> ORGANISM: Artificial Sequence
<220> FEATURE:
<223> OTHER INFORMATION: Description of Artificial Sequence: Oligo12

<400> SEQUENCE: 14
ctgcagcttg aatgagcaga tcaccgtgcc tgacaccaaa gtgaatttct at        52
```

```
<210> SEQ ID NO 15
<211> LENGTH: 49
<212> TYPE: DNA
<213> ORGANISM: Artificial Sequence
<220> FEATURE:
<223> OTHER INFORMATION: Description of Artificial Sequence: Oligo13

<400> SEQUENCE: 15
cagtcttccc agccgtggga gcccctgcaa ctgcatgtgg ataaagccg            49

<210> SEQ ID NO 16
<211> LENGTH: 48
<212> TYPE: DNA
<213> ORGANISM: Artificial Sequence
<220> FEATURE:
<223> OTHER INFORMATION: Description of Artificial Sequence: Oligo14

<400> SEQUENCE: 16
ggaagccatc tccctccag atgcggccgc agctgctccc ctccgcac             48

<210> SEQ ID NO 17
<211> LENGTH: 232
<212> TYPE: PRT
<213> ORGANISM: Homo sapiens
<220> FEATURE:
<223> OTHER INFORMATION: Human IgG1 Fc region-mature protein

<400> SEQUENCE: 17
```

Glu Pro Lys Ser Cys Asp Lys Thr His Thr Cys Pro Pro Cys Pro Ala
 1               5                  10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
 50                  55                  60

Asp Gly Val Glu Val His Asn Ala Lys Thr Lys Pro Arg Glu Glu Gln
 65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 18
<211> LENGTH: 326
<212> TYPE: PRT
<213> ORGANISM: Homo sapiens
<220> FEATURE:
<223> OTHER INFORMATION: Human IgG2 constant region (CH1, hinge, CH2, Ch3) - mature protein

<400> SEQUENCE: 18

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Asn Phe Gly Thr Gln Thr
 65                  70                  75                  80

Tyr Thr Cys Asn Val Asp His Lys Pro Ser Asn Thr Lys Val Asp Lys
                 85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 19
<211> LENGTH: 4
<212> TYPE: PRT
<213> ORGANISM: Artificial Sequence

```
<220> FEATURE:
<223> OTHER INFORMATION: Description of Artificial Sequence: Linker

<400> SEQUENCE: 19

Ala Ala Ala Ala
  1

<210> SEQ ID NO 20
<211> LENGTH: 5
<212> TYPE: PRT
<213> ORGANISM: Artificial Sequence
<220> FEATURE:
<223> OTHER INFORMATION: Description of Artificial Sequence: Linker

<400> SEQUENCE: 20

Ala Ala Ala Ala Ala
  1               5

<210> SEQ ID NO 21
<211> LENGTH: 4
<212> TYPE: PRT
<213> ORGANISM: Artificial Sequence
<220> FEATURE:
<223> OTHER INFORMATION: Description of Artificial Sequence: Linker

<400> SEQUENCE: 21

Gly Gly Gly Gly
  1

<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence: Linker

<400> SEQUENCE: 22

Gly Gly Gly Gly Gly
  1               5

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Linker

<400> SEQUENCE: 23

Gly Gly Gly Gly Gly Gly Gly
  1               5

<210> SEQ ID NO 24
<211> LENGTH: 5
<212> TYPE: PRT
<213> ORGANISM: Artificial Sequence
<220> FEATURE:
<223> OTHER INFORMATION: Description of Artificial Sequence: Linker

<400> SEQUENCE: 24

Gly Gly Pro Gly Gly
  1               5

<210> SEQ ID NO 25
<211> LENGTH: 5
<212> TYPE: PRT
<213> ORGANISM: Artificial Sequence
<220> FEATURE:
```

```
-continued

<223> OTHER INFORMATION: Description of Artificial Sequence: Linker

<400> SEQUENCE: 25

Gly Gly Gly Gly Ser
1               5

<210> SEQ ID NO 26
<211> LENGTH: 25
<212> TYPE: PRT
<213> ORGANISM: Artificial Sequence
<220> FEATURE:
<223> OTHER INFORMATION: Description of Artificial Sequence: Linker
<220> FEATURE:
<223> OTHER INFORMATION: This linker sequence may encompass five to
      twenty five amino acids is groups of (GGGGS)

<400> SEQUENCE: 26

Gly Gly Gly Gly Ser Gly Gly Gly Ser Gly Gly Gly Gly Ser Gly
1               5                   10                  15

Gly Gly Gly Ser Gly Gly Gly Gly Ser
            20                  25

<210> SEQ ID NO 27
<211> LENGTH: 53
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 27
aatcactgct gacactttcc gcaaactctt ccgagtctac tccgcattcc tcc         53

<210> SEQ ID NO 28
<211> LENGTH: 25
<212> TYPE: PRT
<213> ORGANISM: Homo sapiens

<400> SEQUENCE: 28

Glu Ala Glu Asn Ile Thr Thr Gly Cys Ala Glu His Cys Ser Leu Asn
1               5                   10                  15

Glu Asn Ile Thr Val Pro Asp Thr Lys
            20                  25

<210> SEQ ID NO 29
<211> LENGTH: 21
<212> TYPE: PRT
<213> ORGANISM: Homo sapiens

<400> SEQUENCE: 29

Gly Gln Ala Leu Leu Val Asn Ser Ser Gln Pro Cys Glu Pro Leu Gln
1               5                   10                  15

Leu His Val Asp Lys
            20
```

ERYTHROPOIETIN FORMS WITH IMPROVED PROPERTIES

This application claims the benefit of the filing date of U.S. Provisional Application Ser. No. 60/164,855 filed Nov. 12, 1999.

FIELD OF THE INVENTION

The present invention relates to novel erythropoietin forms such as fusion proteins comprising a Fc portion of an Ig molecule and a molecule having the biological activity of erythropoietin (EPO). By selective altering of the amino acid sequences of the erythropoietin moiety as well as of the immunoglobulin moiety and the glycosylation pattern of erythropoietin, fusion proteins (Fc-EPO) and non-fused EPO with improved properties, e.g. enhanced biological activity and stability, can be obtained. Furthermore, fusion proteins can be provided, wherein shortened versions of erythropoietin and the immunoglobulin chain are used. The invention relates also to novel (non-fused) EPO molecules which have a pattern of cysteines and disulfide bonding which is distinct from human or animal EPO.

BACKGROUND

Erythropoiesis, the production of red blood cells, occurs continuously throughout the human life span as a compensation for cell destruction. Erythropoiesis is a precisely controlled physiological mechanism enabling sufficient numbers of red blood cells to be available in the blood for proper tissue oxygenation, but not so many that the cells would impede circulation. The maturation of red blood cells is under the control of the hormone, erythropoietin (EPO).

Erythropoietin is an acidic glycoprotein hormone of approximately 34,000 daltons. Naturally occurring erythropoietin is produced by the liver during fetal life and by the kidney in response to hypoxia (e.g., red blood cell loss due to anemia) and regulates red blood cell growth and differentiation through interaction with its cognate cellular receptor cells into erythrocytes. It is essential for regulating levels of red blood cells in blood circulation of adults and stimulates the production of red blood cells in bone marrow. Anemia is a consequence of renal failure to produce erythropoietin. Recombinant erythropoietin produced by genetic engineering techniques involving the expression of a protein product from a host cell transformed with the gene encoding erythropoietin has been found to be effective when used in the treatment of anemia resulting from chronic renal failure. Wild type, or naturally-occurring, erythropoietin is defined herein to include recombinant erythropoietin (Jacobs, K, et al., Nature, 313:806–813 (1985)), or naturally-occurring erythropoietin which has been isolated and purified from blood (Miyake, T., et al., J. Biol. Chem., 252:5558–5564 (1977)) or sheep plasma (Goldwasser, E., et al., Proc. Natl. Acad. Sci. U.S.A., 68:697–698 (1971)), or chemically synthesized erythropoietin which can be produced using techniques well known to those of skill in the art. Human erythropoietin is a 166 amino acid polypeptide that exists naturally as a monomer (Lin, F K., et al., Proc. Natl. Acad. Sci. USA 82:7580–7584 (1985)). The tertiary structure of erythropoietin as an isolated protein and in a complex with its receptor has been reported (Syed R S, et al., Nature [1998] 395:511–6; Cheetham J C, Nat Struct Biol. [1998] 5:861–6). The identification, cloning, and expression of genes encoding erythropoietin are described in U.S. Pat. No. 4,703,008. A description of the purification of recombinant erythropoietin from cell medium that supported the growth of mammalian cells containing recombinant erythropoietin plasmids for example, is included in U.S. Pat. No. 4,667,016. The expression and recovery of biologically active recombinant erythropoietin from a mammalian cell containing the erythropoietin gene on a recombinant plasmid has made available quantities of erythropoietin suitable for therapeutic applications. In addition, knowledge of the gene sequence and the availability of larger quantities of purified protein has led to a better understanding of the mode of action of this protein. Several forms of anemia, including those associated with renal failure, HIV infection, blood loss and chronic disease can be treated with this hematopoietic growth factor. Erythropoietin is typically administered by intravenous or subcutaneous injection three times weekly at a dose of approximately 25–100 U/kg.

Unlike proteins from prokaryotic cells, many cell surface and secretory proteins produced by eukaryotic cells are modified with one or more oligosaccharide groups. This modification, referred to as glycosylation, can dramatically affect the physical properties of proteins and can also be important in protein stability, pharmacokinetics, secretion, and subcellular localization. Proper glycosylation can be essential for biological activity. In fact, some genes from eukaryotic organisms, when expressed in bacteria (e.g., *E. coli*) which lack cellular processes for glycosylating proteins, yield proteins that are recovered with little or no activity by virtue of their lack of glycosylation. Glycosylation occurs at specific locations along the polypeptide backbone and is usually of two types: 0-linked oligosaccharides are attached to serine or threonine residues while N-linked oligosaccharides are attached to asparagine residues when they are part of the sequence Asn-X-Ser/Thr, where X can be any amino acid except proline. The structures of N-linked and 0-linked oligosaccharides and the sugar residues found in each type are different. One type of sugar that is commonly found on both is N-acetylneuraminic acid (hereafter referred to as sialic acid). Sialic acid is usually the terminal residue of both N-linked and 0-linked oligosaccharides and, by virtue of its negative charge, may confer acidic properties to the glycoprotein. Human recombinant erythropoietin (expressed in mammalian cells) contains three N-linked and one 0-linked oligosaccharide chains which together comprise about 40% of the total molecular weight of the glycoprotein. N-linked glycosylation occurs at asparagine residues (Asn) located at positions 24, 38 and 83 while 0-linked glycosylation occurs at a serine residue (Ser) located at position 126 (Lai et al. J. Biol. Chem. 261, 3116 (1986); Broudy et al. Arch. Biochem. Biophys. 265, 329 (1988)). The oligosaccharide chains have been shown to be modified with terminal sialic acid residues. EPO isoforms having a modified sialic acid pattern are disclosed e.g. in EP 0668 351 or EP 0428 267.

Glycosylation does not seem to be essential for activity, because enzymatically deglycosylated erythropoietin has an activity similar to that of the normally glycosylated protein. However, when the glycosylation sites in erythropoietin are mutated to prevent glycosylation, there is a profound inhibition of the normal synthesis and export of the protein (Dube et al., JBC [1988] 263:17516). Specifically, elimination of glycosylation at $Asn_{38}$ causes a 99% synthesis block, and elimination of glycosylation at $Asn_{83}$ causes at least a 99.99% synthesis block, and elimination of glycosylation at $Ser_{126}$ causes a 99.8% synthesis block.

One problem with erythropoietin therapy is that, although quite effective, this form of therapy is very expensive. Another problem encountered in the practice of medicine when using injectable pharmaceuticals is the frequency at which those injections must be made in order to maintain a therapeutic level of the compound in the circulation. For example, erythropoietin has a relatively short plasma half-life (Spivak, J. L., and Hogans, B. B., *Blood*, 73:90 (1989); McMahon, F. G., et al., *Blood,* 76:1718(1990)), therefore, therapeutic plasma levels are rapidly lost, and repeated intravenous administrations must be made.

It would be advantageous to have available derivatives of erythropoietin which have an extended circulating half-life to avoid such problems. In addition one would prefer to synthesize EPO in a host cell other than a mammalian cell. Unfortunately, synthesis in bacteria is problematic because the protein is not produced in a properly folded, native conformation. Synthesis in insect cells or plant cells is also problematic because these cells provide an unfavorable glycosylation pattern. Proteins that are glycosylated according to the insect pattern or the plant patterns are, upon injection into animals, generally taken up by specific receptors and rapidly degraded. For example, macrophages in the liver possess high mannose receptors and asialo-glycoprotein receptors that remove proteins with non-mammalian glycosylation patterns.

SUMMARY OF THE INVENTION

The invention provides novel modified EPO forms, above all fusion proteins but also non-fused EPO modifications, with surprising activities that address the above-said problems.

Fusion proteins and modification of specified fusion proteins are known in the art. For example, fusion proteins may effectively block a proteolytic enzyme from physical contact with the protein backbone itself, and thus prevent degradation. Additional advantages include, under certain circumstances, improved yield in a specific expression system, correct folding of a target protein, and increasing the stability, circulation time, and the biological activity of the therapeutic protein. One such modification is the use of the Fc region of immunoglobulins. Antibodies comprise two functionally independent parts, a variable domain known as "Fab", which binds antigen, and a constant domain, known as "Fc" which provides the link to effector functions such as complement or phagocytic cells.

The Fc portion of an immunoglobulin mediates a long plasma half life when fused to certain proteins that have particularly short half lives, whereas the mere Fab fragment is short-lived. Capon, et al., Nature 337: 525–531 (1989). For example, IL-10, an anti-inflammatory and anti-rejection agent has been fused to the N-terminus of murine Fcγ2a in order to increase the cytokine's short circulating half-life (Zheng, X. et: al., The Journal of Immunology, 154: 559C–5600 (1995)). In addition, the N-terminus of interleukin 2 has also been fused to the Fc portion of IgG1 or IgG3 to overcome the short half life of interleukin 2 and its systemic toxicity (Harvill et al., Immunotechnology, 1: 95–105 (1995)). IL-10 and IL-2, unlike EPO, are small proteins that have very short serum half-lives because they are rapidly cleared by renal filtration.

Therapeutic fusion proteins have also been constructed using the Fc domain to incorporate functions such as Fc receptor binding, protein A binding, complement fixation and placental transfer which all reside in the Fc proteins of immunoglobulins. For example, the Fc region of an IgG1 antibody has been fused to the N-terminal end of CD30-L, a molecule which binds CD30 receptors expressed on Hodgkin's Disease tumor cells, anaplastic lymphoma cells, T-cell leukemia cells and other malignant cell types (U.S. Pat. No. 5,480,981). Furthermore, it has been reported in 1996 that efficient expression and secretion of certain non-mutant target proteins can be achieved by expression of fusion proteins comprising an Fc portion of an immunoglobulin and said target proteins followed by proteolytic cleavage of the target protein (WO 96/08570, U.S. Pat. No. 5,541,087).

The invention presents novel proteins that have erythropoietin-like activity in their ability to stimulate production of red blood cells in an animal, but with additional advantageous properties such as increased activity, the ability to be synthesized without glycosylation and longer serum half-life. These novel proteins include mutated versions of EPO which are not fused to other proteins, fusion proteins of EPO to immunoglobulin regions, forms of EPO with altered glycosylation, forms of EPO that usefully combine mutation, fusion to other moieties, and/or altered glycosylation, forms of EPO that have a truncated amino acid sequence, forms of Fc immunoglobulin portions which are modified/ mutated having herewith a reduced affinity e.g. to Fc receptors, shortened or truncated forms of Fc and Fc-EPO constructs having specific linkers.

The EPO forms as defined above and below such as Fc-EPO fusion proteins of this invention show improved properties such as enhanced biological activity and improved stability.

DETAILED DESCRIPTION

It is an object of the present invention to provide a modified erythropoietin (EPO) form having improved properties, wherein said EPO form can be either a non-fused human or mammalian modified EPO having the pattern of cysteines or disulfide bonds that differs from the disulfide bonding or cysteine pattern of human or mammalian EPO, or a fusion protein comprising a Fc portion of an Ig molecule and an erythropoietin molecule (EPO), wherein said Fc portion is fused covalently via its C-terminus directly or indirectly to said EPO molecule by its N-terminus and wherein the Fc portion as well as the EPO portion may be modified or mutated, selected from the group:

(i) Fc-EPO (ii) Fc-L-EPO (iii) Fc-EPO$_{desial}$ (iv) Fc-EPO$_m$ (v) Fc$_m$-EPO (vi) Fc$_m$-EPO$_m$ (vii) Fc$_m$-L-EPO (viii) Fc-L-EPO$_m$ (ix) Fc-EPO$_{trunc}$ (x) Fc-L-EPO$_{trunc}$ Herein, EPO has the meaning of naturally occurring EPO from mammalian, preferably human origin and includes also recombinant EPO engineered from natural sources. This EPO according to the invention is glycosylated, non-glycosylated, partially glycosylated or otherwise modified in its glycosylation pattern as indicated above, below and in the prior art. For certain uses, the EPO moiety has a correctly folded structure. The invention discloses novel methods for synthesizing forms of EPO that are unglycosylated. Previously, it was known that glycosylated EPO could be treated with N-glycosidase, which removes sugar groups that are attached to asparagine. However, this enzyme does not remove the distinct sugar modification that is found on $Ser_{126}$. As a general alternative method of synthesis, it is possible to express EPO in bacteria, where no glycosylation will occur. However, proteins synthesized by this method generally are obtained as denatured proteins in inclusion bodies, and do not have disulfide bonds. Thus, additional effort is required to reconstitute the protein into a soluble state. Finally, mutation of the glycosylation sites in EPO results in a protein that cannot be synthesized in mammalian cells (Dube et al., JBC [1988] 263:17516). It appears that the mutant protein is degraded before it can be secreted. However, as disclosed herein, when DNA constructs encoding Fc-unglycosylated EPO are placed in mammalian cell lines, the Fc-unglycosylated EPO is efficiently expressed, secreted, and found in a soluble form in the culture supernatant. The Fc-unglycosylated EPO fusion protein can be purified by standard techniques, for example, on a protein A column. For example, the Fc-unglycosylated EPO can be injected into animals as an antigen to raise antibodies that are directed against the novel epitopes revealed by the absence of glycosylation. In addition, the Fc-unglycosylated EPO, containing only mutations at the glycosylation sites, has detectable EPO activity and can be used as a starting point for the isolation of additionally mutated forms that have increased activity.

$EPO_{desial}$ is a glycosylated EPO according to the invention, wherein sialic acid residues that are normally found on a secreted, glycosylated protein are partially or substantially absent. This can be achieved by enzymatically treatment with an enzyme such that the sialic acid residues have been substantially removed. For example, a protein that is treated with the enzyme neuraminidase will have its sialic acids removed. Such a protein is also recognized by the asialoglycoprotein receptor in the liver. A desialylation can also be achieved by using mutated cells which are deficient in enzymes responsible for this step. For example, the known Lec-2 mutant derivative of the CHO cell line is defective in addition of sialic acid residues to N-linked and O-linked sugar chains in secreted proteins ("asialo"). As a result, the exposed galactose residue on such proteins can be recognized by the asialoglycoprotein receptor in the liver, taken up into cells, and is usually degraded. The desialylation in the EPO moiety of the fusion proteins according to the invention does not need to be completely removed.

$EPO_{trunc}$ is an EPO according to this invention which is truncated but not mutated in its amino acid sequence. Truncated forms are protein fragments having essentially the full or only a slightly reduced biological activity of erythropoietin. Preferred truncated forms of EPO according to this invention are shortened at the C-terminus and have at least 65 amino acids calculated from the N-terminal. Preferred truncated EPO forms have 155–116, 108, 104, 98, 93, 88, 85 or 78 amino acids. Especially preferred forms of EPO ends C-terminally with amino acid positions 108, 104, 98, 93, 88, 85 or 78.

The Fc region of an immunoglobulin is the amino acid sequence for the carboxyl-terminal portion of an immunoglobulin heavy chain constant region. The Fc regions are particularly important in determining the biological functions of the immunoglobulin and these biological functions are termed effector functions. As known, the heavy chains of the immunoglobulin subclasses comprise four or five domains: IgM and IgE have five heavy chain domains, and IgA, IgD and IgG have four heavy chain domains. The Fc region of IgA, IgD and IgG is a dimer of the hinge-$CH_2$–$CH_3$ domains, and in IgM and IgE it is a dimer of the hinge-$CH_2$–$CH_3$–$CH_4$ domains (see, W. E. Paul, ed., 1993, Fundamental Immunology, Raven Press, New York, N.Y.).

As used herein, the term "Fc portion of an Ig molecule" means the carboxyl-terminal portion of an immunoglobulin heavy chain constant region, or an analog or portion thereof. That is, e.g., an immunoglobulin Fc region of Ig, preferably IgG, most preferably IgG1, IgG2 and IgG3, may comprise at least a portion of a hinge region, a CH2 domain, and a CH3 domain. In a preferred embodiment the Fc region includes at least a portion of a hinge region and a CH3 domain.

In some circumstances, it is useful to mutate certain amino acids within the Fc moiety of an Fc-EPO fusion protein. For example, if an Fc-EPO fusion protein is to be expressed in a cell type that generates a non-human glycosylation pattern, it is often useful to mutate the glycosylation site within the Fc region and thus entirely eliminate glycosylation at this site. As a result, the resulting protein will not be identified and degraded by scavenging systems that recognize altered glycosylation patterns.

Thus, $Fc_m$ is a Fc portion as defined above which is mutated and/or truncated in its amino acid sequence and/or modified in its glycosylation pattern. It has been shown by this invention that such modified Fc portions lead to Fc-EPO fusion proteins with improved properties. In this context $Fc_m$ includes additionally modified or mutated Fc portions which have a reduced affinity to Fc receptors on cells. The binding affinity of fusion proteins for Fc receptors can be reduced by using heavy chain isotypes as fusion partners that have per se diminished binding affinity for Fc receptors on cells. For example, it is known that, for example, IgG1 and IgG3 bind to FcRγI with high affinity and that the binding sites are located in the CH2 domain. Thus, it is an object of the invention to provide a Fc-EPO fusion protein with enhanced in vivo circulating half-life having a mutation, deletion or insertion at one or more amino acids in the domains responsible for Fc receptor binding. In a preferred embodiment of the invention the Fc-EPO fusion protein comprises a Fc portion of an IgG1, wherein said mutations, deletions, or insertions in the IgG1 constant region are selected from $Leu_{234}$, $Leu_{235}$, $Gly_{236}$, $Gly_{237}$, $Asn_{297}$, and $Pro_{331}$. In an alternative preferred embodiment the mutation, deletion or insertion is introduced in the IgG1 constant region of a Fc portion of a fusion protein according to the invention at one ore more amino acids selected from $Leu_{281}$, $Leu_{282}$, $Gly_{283}$, $Gly_{284}$, $Asn_{344}$ and $Pro_{378}$. Methods for making Fc portions with reduced Fc receptor affinity are, for example, disclosed in PCT/US99/03966.

The invention also discloses methods for generating useful mutant forms of Fc-EPO in which the EPO moiety is altered. Variants of Fc-EPO with increased EPO biological activity can be generated by procedures described in the Examples and known in the art.

Thus, $EPO_m$ is an EPO according to this invention which is mutated but not truncated in its amino acid sequence. The number of mutations is not limited but is restricted to the loss of the biological activity of the molecule. Preferably mutations of 1 to 10 amino acids are used. Surprisingly it could be shown that the Fc fusion proteins according to the invention, wherein EPO is mutated as defined above, have greater specific activity than the comparable Fc-EPO fusion proteins having no mutated EPO moieties. Therefore, it is an preferred object of the invention to provide Fusion proteins as defined above and in the claims, wherein EPO is mutated. Preferred fusion proteins of this invention have an EPO molecule, wherein in the $EPO_m$ portion at least one of the following changes are achieved: $Asn_{24, 38, 83} \rightarrow Xxx$, $Ser_{126} \rightarrow Xxx$, where Xxx is a different amino acid. Preferred changes according to the invention are $Asn_{24, 38, 83} \rightarrow Gln$ and/or $Ser_{126} \rightarrow Ala$. Further preferred mutations are: His 32→Gly and/or Ser 34→Arg and/or Pro 90→Ala. In one embodiment of the invention all above-said mutations are achieved.

These and other variant proteins according to the invention may enhance binding to the EPO receptor, enhanced stability, enhanced adoption of a correct, active conformation, enhanced pharmacokinetic properties, enhanced synthesis, or other advantageous features. Mutations in the EPO moiety of Fc-EPO can be combined to generate proteins that have further enhanced activities.

A specific method for improvement of Fc-EPO disclosed in the Examples uses site-directed mutagenesis techniques. It is important to note that a wide variety of site-directed mutagenesis techniques are available, and can be used as alternatives to achieve similar results. The strategies for choosing among these techniques is well-known to those skilled in the art of molecular biology. Similarly, there is a wide variety of techniques for achieving random and semi-random mutagenesis of a target DNA. These techniques are also well-known to those skilled in the art of molecular biology.

Additional mutant forms of Fc-EPO may be constructed according to this invention. The mutations have the effect of increasing the activity of unglycosylated Fc-EPO. Depending on the mutation, activity is increased by a variety of mechanisms, such as increasing affinity of Fc-EPO for the EPO receptor, increasing the fraction of Fc-EPO that is properly folded, or improving the pharmacokinetic properties of Fc-EPO. Some mutations, when combined, have an additive or multiplicative effect on the activity of unglycosylated Fc-EPO.

The Fc portion and the EPO proteins according to this invention may also be linked by linker molecules, wherein the chemical or amino acid linkers are of varying length. The chemical linkers are well known in the art. Peptide linkers are preferred. Fusion proteins, wherein the Fc portion is linked with the target protein by a linker molecule may have improved properties. The Fc-EPO fusion proteins according to the invention having such linker molecules show an enhanced biological activity. The linker of the invention (L) is a linker molecule as defined above and below which has no protease cleavage site.

The peptide linker often is a series of peptides such as. e.g., glycine and/or serine. Preferably, the peptide linker is a mixed series of glycine and serine peptides about 5–25, preferably 10–20 residues in length.

Preferred amino acid linkers L are used and include the following sequences, wherein such linkers are excluded that possess a cleavage site for proteolytic enzymes:

1. Ala Ala Ala
2. (SEQ ID NO: 19) Ala Ala Ala Ala,
3. (SEQ ID NO: 20) Ala Ala Ala Ala Ala,
4. Ser,
5. Ser Ser,
6. Gly Gly Gly,
7. (SEQ ID NO: 21) Gly Gly Gly Gly,
8. (SEQ ID NO: 22) Gly Gly Gly Gly Gly,
9. (SEQ ID NO: 23) Gly Gly Gly Gly Gly Gly Gly,
10. Gly Pro Gly,
11. (SEQ ID NO: 24) Gly Gly Pro Gly Gly,
12. (SEQ ID NO: 25) Gly Gly Gly Gly Ser, and
13. any combinations of subparts 1–12

Preferred amino acid linkers are (SEQ ID NO: 26) (Gly Gly Gly Gly $Ser)_x$ wherein x is 1–5. Additional suitable linkers are disclosed in Robinson et al., 1998, Proc. Natl. Acad. Sci. USA; 95, 5929.

As used herein, "proteolytic cleavage site" means amino acid sequences which are preferentially cleaved by a proteolytic enzyme or other proteolytic cleavage agents. Proteolytic cleavage sites include amino acids sequences which are recognized by proteolytic enzymes such as trypsin, plasmin or enterokinase K. Many cleavage site/cleavage agent pairs are known. Where the target protein sequence is a precursor molecule to Interferon-alpha or an active variant thereof, the desired protein product may be produced by cleavage with the endogenous proteolytic enzyme, such as elastin or plasmin or urokinase.

As used above and below, the biological activity of erythropoietin and EPO fusion proteins, respectively, is defined as the ability to regulate red blood cell growth and differentiation through interaction with its cognate cellular receptor, or the antigenic property of inducing a specific immunological response as determined using well-known laboratory techniques. For example, a biologically active, or functionally active, fragment of erythropoietin ($EPO_{trunc}$) can induce an immunological response which produces antibodies specific for erythropoietin (anti-erythropoietin antibodies).

To be "functionally" or "biologically active" an erythropoietin-like molecule, such as Fc-EPO, typically shares substantial sequence (amino acid) similarity (e.g., at least about 65%, typically at least about 80% and most typically about 90–95%) with the corresponding sequences of wild type, or naturally-occurring, erythropoietin and possesses one or more of the functions of wild type erythropoietin thereof.

As pointed out above the fusion proteins of the present invention have improved properties. Thus, they show improved biological activity and have an extended serum half-life, wherein said extended serum half-life is greater than 15 hours, preferably greater than 20 hours, most preferably greater than 25 hours.

Another and important aspect of this invention is the finding that in order to get improved EPO forms, preferably Fc-EPO fusion proteins, it is advantageous to introduce altered patterns of cysteine—cysteine disulfide bonds. Thus, it is an object of the invention to provide Fc-EPO fusion proteins or non-fused EPO, wherein at least one, preferably 2–4 cystein residues of the EPO or $EPO_m$ moiety are engineered. Especially, it is an object of the invention to provide Fc-EPO fusion proteins or non-fused EPO, wherein the EPO or $EPO_m$ moiety has a pattern of disulfide bonding which is distinct from human or mammalian EPO. In one embodiment of the invention the EPO moiety includes one or more of the following amino acid variations: position 29 is not Cys, position 33 is not Cys, position 88 is Cys and position 139 is Cys. In a preferred Cys-engineered embodiment of this invention the EPO moiety is derived from human EPO and has at least one of the following mutations: His 32→Gly, Ser 34→to Arg and Pro 90→Ala.

To generate an altered disulfide bond, one cysteine residue is mutated to a structurally compatible amino acid such as alanine or serine, and a second amino acid that is nearby in the three-dimensional structure is mutated to cysteine. Thus, it is a further object of this invention to provide FC-EPO fusion proteins or non-fused EPO, wherein at least one of the cysteine residues of the EPO molecule or $EPO_m$ molecule is engineered by techniques which are well known in the art. One embodiment is a Fc-EPO fusion protein, wherein $Cys_{33}$ is replaced by any other amino acid. In an alternative embodiment a fusion protein is object of the invention, wherein one of the amino acids $Gln_{86}$, $Pro_{87}$, $Trp_{88}$, $Glu_{89}$, $Leu_{91}$ is replaced by Cys. Preferably, $Trp_{88}$ is replaced by Cys. For example, a fusion protein containing an EPO moiety lacking Cys at position 33 and containing Cys at position 88 will form a disulfide bond that is not found in human EPO. This bond results in a fusion protein that has superior properties to an otherwise similar fusion protein containing a disulfide bond between $Cys_{29}$ and $Cys_{33}$. For example, the $Cys_{29}$–$Cys_{88}$ fusion protein has greater activity than the $Cys_{29}$–$Cys_{33}$ fusion protein. In addition, the $Cys_{29}$–$Cys_{88}$ fusion protein shows a pronounced increase in activity, relative to the $Cys_{29}$–$Cys_{33}$ fusion protein, in the presence of other mutations in the EPO moiety of the fusion protein. It is also sometimes useful to incorporate the mutations $His_{32}$ to any other amino acid, preferably Gly or Ser, mutation of $Ser_{34}$ to Arg, and mutation of $Pro_{90}$ to Ala.

Another useful set of mutations includes mutation of $Cys_{29}$ of the EPO of the invention to any other amino acid, and mutation of $Arg_{139}$ to Cys. An EPO form containing both of these mutations will generally contain a disulfide bond between $Cys_{33}$ and $Cys_{139}$. This bond results in a fusion protein that has superior properties to an otherwise similar fusion protein containing a disulfide bond between $Cys_{29}$ and $Cys_{33}$. For example, the $Cys_{33}$–$Cys_{139}$ fusion protein has greater activity than the $Cys_{29}$–$Cys_{33}$ fusion protein. In addition, the $Cys_{33}$–$Cys_{139}$ fusion protein shows a pronounced increase in activity, relative to the $Cys_{29}$–$Cys_{33}$ fusion protein, in the presence of other mutations in the EPO moiety of the fusion protein.

As a further alternative, an entirely new disulfide bond is added to the protein by mutating two amino acids to cysteines.

It is known in the art that erythropoietin synthesized by non-human animals generally contains a different pattern of cysteine residues than human erythropoietin (Wen, D., et al. Erythropoietin structure-function relationships: high degree of sequence homology among mammals Blood 82, 1507–1516 [1993]; Fu, P., et al. The sheep erythropoietin gene: molecular cloning and effect of hemorrhage on plasma erythropoietin and renal/liver messenger RNA in adult sheep Mol. Cell. Endocrinol. 93, 107–116 [1993]; Lin, F. K., et al., Monkey erythropoietin gene: cloning, expression and comparison with the human erythropoietin gene Gene 44, 201–209 [1986]; Suliman, H. B., et al. Cloning of a cDNA encoding bovine erythropoietin and analysis of its transcription in selected tissues Gene 171, 275–280 (1996); McDonald, J. D., Cloning, sequencing, and evolutionary analysis of the mouse erythropoietin gene Mol. Cell. Biol. 6, 842–848 [1986]; Nagao, M., et al. Nucleotide sequence of rat erythropoietin Biochim. Biophys. Acta 1171 (1), 99–102 [1992]). However, the erythropoietin normally produced by most of these animals, such as macaques, pigs, dogs, cats, cows, and sheep, contains five cysteines. Rodents such as mice and rats have four cysteines, but the two of the cysteines are at positions 29 and 139. Based on the three-dimensional structure of human EPO, the cysteines of rodent EPO at positions 29 and 139 are unable to form disulfide bonds with each other or any of the other cysteines. In general, secreted extracellular proteins do not contain unpaired cysteines. In the relatively oxidizing environment of the extracellular space, unpaired cysteines may be oxidized, for example, to cysteic acid. As a result, the activity of the protein may be reduced. Without wishing to be bound by theory, the oxidation of cysteines in the EPO of non-human animals may serve to down-regulate EPO activity, inactivating the EPO protein in conditions of high oxygen when erythropoiesis is not needed.

In any case, the invention provides EPO moieties that are distinct from known animal-derived forms of EPO in that they have an even number of cysteines and all of the cysteines are capable of forming disulfide bonds. These EPO moieties containing novel disulfide bonding patterns may be useful as Fc fusions, as fusions to other proteins such as albumin, or as unfused, isolated moieties.

Another feature of the invention is a form of EPO with cysteines at positions 29, 33, 88, and 139. When this set of cysteines is present in an EPO that contains the usual cysteines at positions 7 and 161, the resulting EPO contains three disulfide bonds instead of two. The resulting molecule is extremely stable, even in the presence of other mutations that destabilize the normal EPO protein. For example, EPO ($Cys_{29}$–$Cys_{88}$, $Cys_{33}$–$Cys_{139}$) is much more stable than normal human EPO. Similarly, fusion proteins such as Fc fusions to EPO ($Cys_{29}$–$Cys_{88}$, $Cys_{33}$–$Cys_{139}$) are more stable than the corresponding fusions to normal human EPO or to normal EPO from non-human animals.

Thus, the invention presents novel forms of EPO and EPO fused to other moieties, preferably an Fc moiety, that have patterns of cysteine residues and disulfide bonds that are different from human and animal EPO. These novel forms of EPO have significant advantages over corresponding natural forms of EPO. For example, forms of EPO with altered disulfide bonding patterns have higher specific activity, increased stability, dramatically increased stability in the presence of other alterations that destabilize EPO, and improved pharmacokinetics. Some of the Examples below illustrate these points. For example, enzymatic deglycosylation of EPO has a destabilizing effect on EPO activity. A form of EPO with an altered pattern of disulfide bonds is more stable upon deglycosylation than the corresponding form of EPO with the normal disulfide bonding pattern. In addition, a form of EPO with an altered pattern of disulfide bonding has a greater specific activity than the corresponding form of EPO with a normal pattern of disulfides.

Thus, it is also an object of the present invention to provide a novel recombinant human or animal preferably mammalian (non-Fc-fused) erythropoietin (EPO) having the pattern of disulfide bonds that differs from the disulfide bonding pattern of human or animal/mammalian EPO. Animal or mammalian EPO according to the invention may derive from mice, macaques, rats, dogs, pigs, cows or sheep.

Furthermore, it is an object of the present invention to provide a fusion protein as defined above and in the claims, wherein the EPO or $EPO_m$ portions within the Fc fusion protein are dimerized.

The term "dimeric" refers to a specific multimeric molecule, wherein two protein subunits are stably associated through covalent or non-covalent interactions. As used herein, the term "multimeric" refers to the stable association of two or more protein subunits by means of covalent interaction, for example, by a disulfide bond or by means of non-covalent interaction.

It should be understood that the Fc fragment itself typically is a dimer of the heavy chain fragments including at least a portion of the hinge region, $CH_2$ domain and $CH_3$ domain. However, many protein ligands are known to bind to their receptors as a dimer. If a protein ligand X dimerizes naturally, the X moiety in a Fc-X molecule will dimerize to a much greater extent, since the dimerization process is concentration dependent. The physical proximity of the two X moieties connected by Fc would make the dimerization an intramolecular process, greatly shifting the equilibrium in favor of the dimer and enhancing its binding to the receptor.

It is another object according to the invention to construct EPO fusion proteins, wherein a whole or intact Ig molecule is used. Such fusion molecules comprise the variable regions of heavy and light chains of an antibody and the epitopes binding to a specific antigen. For example, erythropoietin is fused to the C-terminus of an antibody heavy chain within an antibody whose variable regions are directed against an antigen to which much or all of the human population has been exposed. Such an antibody is termed a "universal antibody" in this disclosure. It is important to note that the use of "universal" antibodies in the construction of antibody fusion proteins can be generalized to fusion molecule with other protein moieties besides erythropoietin. By a "universal" antibody is meant an antibody with a specificity that is found in much, most, or all of a mammalian population, such as the human population.

For example, variable regions directed against tetanus toxoid are encoded in the human genome and the corresponding proteins are generally represented in the serum without having experienced somatic mutation. Thus, according to the invention, erythropoietin is fused to the C-terminus of a heavy chain of an antibody directed against tetanus toxoid. An advantage of such an antibody-erythropoietin fusion is that the antibody variable regions do not bind strongly to a mammalian self-antigen. A second advantage is that anti-idiotype antibodies are less likely to be generated de novo against such an antibody than to an antibody with an uncharacterized variable region.

DNA constructs encoding whole antibody fusion proteins may be constructed as described previously (Gillies et al. [1991] Hybridoma 10:347–356).

The invention also relates to a DNA molecule that encodes any of the fusion proteins disclosed above and depicted in the claims.

As a preferred embodiment a DNA molecule is disclosed that encodes a fusion protein as defined above and in the claims comprising:

(a) a signal/leader sequence (b) a Fc region of an Ig molecule (c) a target protein sequence having the biological activity of EPO.

The signal sequence of the invention as indicated above is a polynucleotide which encodes an amino acid sequence that initiates transport of a protein across the membrane of the endoplasmic reticulum. Signal sequences which will be useful in the invention include antibody light chain signal sequences, e.g., antibody 14.18 [Gillies et. al. (1989) *Jour. of Immunol. Meth.*, 125:19 1], antibody heavy chain signal sequences, e.g., the MOPC141 antibody heavy chain signal sequence [Sakano et al. (1980) *Nature* 286:5774], and any other signal sequences which are known in the art (see for example, Watson, 1984, Nucleic Acids Research 12:5145). Each of these references is incorporated herein by reference. Signal sequences have been well characterized in the art and are known typically to contain 16 to 30 amino acid residues, and may contain greater or fewer amino acid residues. A typical signal peptide consists of three regions: a basic N-terminal region, a central hydrophobic region, and a more polar C-terminal region. The central hydrophobic region contains 4 to 12 hydrophobic residues that anchor the signal peptide across the membrane lipid bilayer during transport of the nascent polypeptide. Following initiation, the signal peptide is usually cleaved within the lumen of the endoplasmic reticulum by cellular enzymes known as signal peptidases.

Potential cleavage sites of the signal peptide generally follow the "(−3, −1) rule". Thus a typical signal peptide has small, neutral amino acid residues in positions −1 and −3 and lacks proline residues in this region. The signal peptidase will cleave such a signal peptide between the −1 and +1 amino acids. Thus, the portion of the DNA encoding the signal sequence may be cleaved from the amino-terminus of the Fc-fusion protein during secretion. This results in the secretion of a Fc-fusion protein consisting of the Fc region and the target protein. A detailed discussion of signal peptide sequences is provided by von Heijne (1986) Nucleic Acids Res., 14:4683. As would be apparent to one of skill in the art, the suitability of a particular signal sequence for use in a secretion cassette may require some routine experimentation. A signal sequence is also referred to as a "signal peptide", "leader sequence" or "leader peptides" and each of these terms having meanings synonymous to signal sequence may be used herein.

The invention also relates to expression vectors comprising said DNA molecules which promote expression of the target protein, that is a Fc-EPO fusion protein. As used herein, "vector" means any nucleic acid comprising a nucleotide sequence competent to be incorporated into a host cell and to be recombined with and integrated into the host cell genome, or to replicate autonomously as an episome. Such vectors include linear nucleic acids, plasmids, phagemids, cosmids, RNA vectors, viral vectors and the like. Non-limiting examples of a viral vector include a retrovirus, an adenovirus and an adeno-associated virus. As used herein, "expression of a target protein" is understood to mean the transcription of the DNA sequence, translation of the mRNA transcript, and secretion of a protein product that is folded into a correct, active conformation.

According to the invention eukaryotic, preferably mammalian, host cells are used that are suitable for expressing a fusion protein as defined in this application. Methods of transfecting such host cells with said vector, expressing, purifying and isolating the fusion proteins of this invention are well known in the art.

Therefore, the method according to this invention comprises:

(i) constructing a DNA encoding a precursor protein that comprises from N-terminus to C-terminus a leader sequence for secretion, the Fc portion and the EPO, $EPO_m$ or $EPO_{trunc}$, (ii) placing said fused DNA in an approbiate expression vector, (iii) expressing said fusion protein in a eukaryotic cell, and (iv) purifying said secreted fusion protein.

Finally, the invention also relates to pharmaceutical compositions comprising at least one of the EPO forms as defined above and below, preferably a Fc-EPO fusion protein, together with pharmaceutically acceptable carriers, diluents, and excipients. These pharmaceutical compositions may optionally contain other drugs or medicaments that are helpful in co-treating EPO deficient diseases.

Such pharmaceutical compositions may be for parenteral administration, or for oral, pulmonary, nasal, transdermal or other forms of administration. In general, comprehended by the invention are pharmaceutical compositions comprising effective amounts of protein or derivative products of the invention together with pharmaceutically acceptable diluents, preservatives, solubilizers, emulsifiers, adjuvants and/or carriers. Such compositions include diluents of various buffer content (e.g., Tris-HCl, acetate, phosphate), pH and ionic strength; additives such as detergents and solubilizing agents (e.g., Tween 80, Polysorbate 80), anti-oxidants (e.g., ascorbic acid, sodium metabisulfite), preservatives (e.g., Thimersol, benzyl alcohol) and bulking substances (e.g., lactose, mannitol). The term "parenteral" as mentioned above and below includes subcutaneous, intravenous, intra-articular and intratracheal injection and infusion techniques. The parenteral administration is preferred.

As used herein, the term "pharmaceutically acceptable carrier or excipient" means an inert, non toxic liquid filler, diluent, solvent or solution, not reacting adversely with the active compounds or with the patient. Suitable liquid carriers are well known in the art such as steril water, saline, aqueous dextrose, sugar solutions, ethanol, glycols and oils, including those of petroleum, animal, vegetable, or synthetic origin. The formulations may also contain adjuvants or vehicles which are typical for parenteral administration.

With respect to said suitable formulations it should be pointed out that the Fusion proteins of the present invention may eventually form pharmaceutically acceptable salts with any non-toxic, organic or inorganic acid showing changed solubility. Inorganic acids are, for example, hydrochloric, sulphuric or phosphoric acid and acid metal salts such as sodium monohydrogen orthophosphate and potassium hydrogen sulfate. Examples for organic acids are the mono, di and tri carboxylic acids such as acetic, glycolic, lactic, pyruvic, malonic, succinic, glutaric, fumaric, malic, tartaric, citric, ascorbic, maleic, benzoic, phenylacetic, cinnamic, salicylic and sulfonic acids. Salts of the carboxy terminal amino acid moiety include the non-toxic carboxylic acid salts formed with any suitable inorganic or organic bases. These salts include, for example, alkali metals such as sodium and potassium, alkaline earth metals such as calcium and magnesium, and organic primary, secondary and tertiary amines such as trialkylamines.

Preferably, the dosage of the pharmaceutical composition according to the invention will be such that between about 10 ng/kg/day and about 10 µg 1 kg/day will yield the desired therapeutic effect. The effective dosages may be determined using diagnostic tools which are known in the prior art. In general, the optimum therapeutically acceptable dosage and dose rate for a given patient within the above-said ranges depends on a variety of factors, such as the activity of the specific active material employed, the age, body weight, general health, sex, diet, time and route of administration, rate of clearance or the object of treatment. One skilled in the art will be able to ascertain effective dosages by administration and observing the desired therapeutic effect. The dosages may also vary over the course of therapy, with a relatively high dosage being used initially, until therapeutic benefit is seen, and lower dosages used to maintain the therapeutic benefits.

SHORT DESCRIPTION OF THE FIGURES

FIG. 1:
Fc-Erythropoietin treated with N-glycosidase SDS gel showing Fc-erythropoietin before and after N-glycosidase F treatment. Lane 1 shows molecular weight size standards, lane 2 is blank, lane 3 shows normally glycosylated Fc-EPO, lane 4 shows normally glycosylated Fc-EPO after incubation in deglycosylation buffer, and lanes 5, 6, and 7 respectively show normally glycosylated Fc-EPO incubated with 20 units of N-glycosidase F (Boehringer-Mannheim) in 0.5 mls for 3 hours, 6 hours, or 18 hours.

Figure 2:
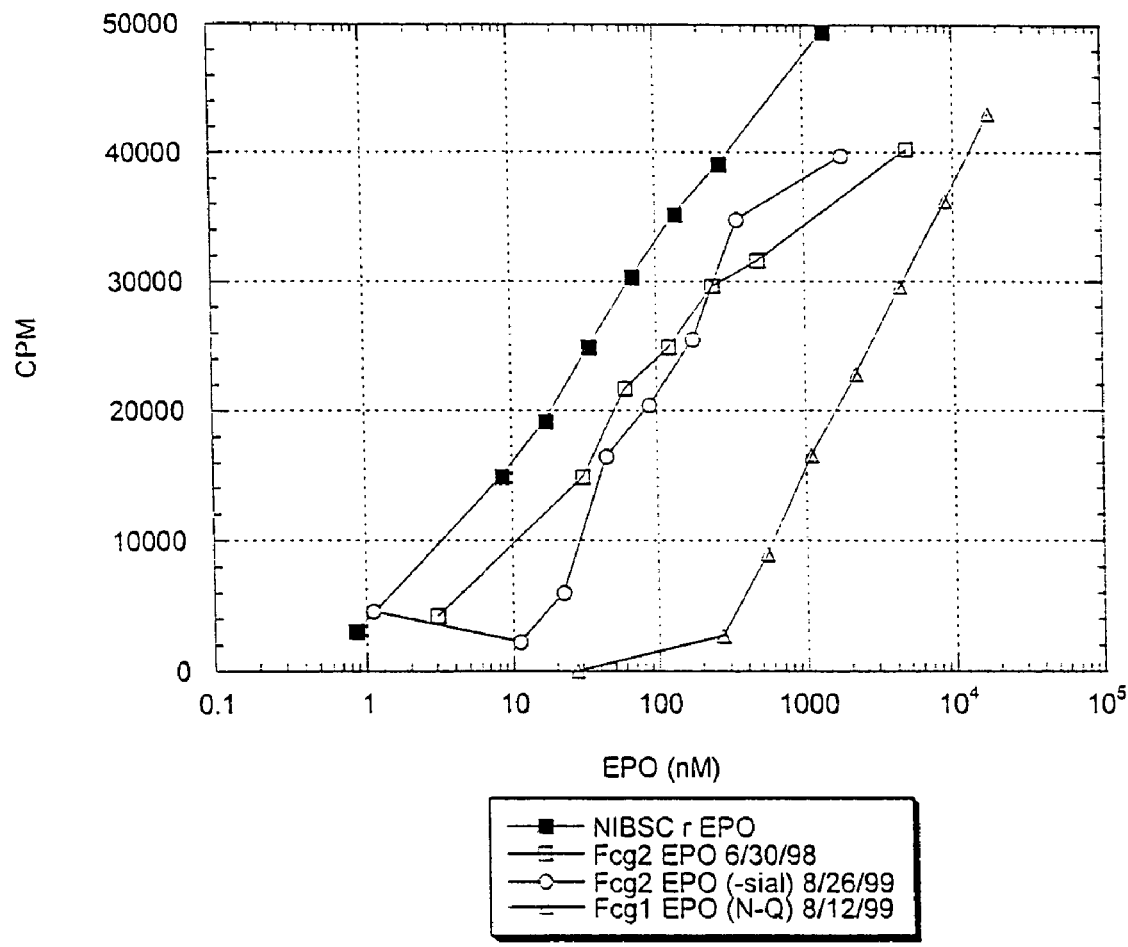

FIG. 2:
This figure depicts a line graph showing the biological activity of the NIBSC EPO (black diamonds), human IgG2 Fc-EPO (white squares), human IgG1 Fc-EPO with mutant glycosylation sites (white circles), and human IgG2 Fc-EPO expressed in CHO-Lec2 cells (white diamonds). The activity of the EPO moiety in various proteins was assayed via EPO-dependent 3H-thymidine incorporation into TF-1 cells. The X-axis indicates the EPO equivalents (ng/ml) present as determined by ELISA, and the Y-axis indicates the dependent 3H-thymidine incorporation in counts per minute.

Figure 3:
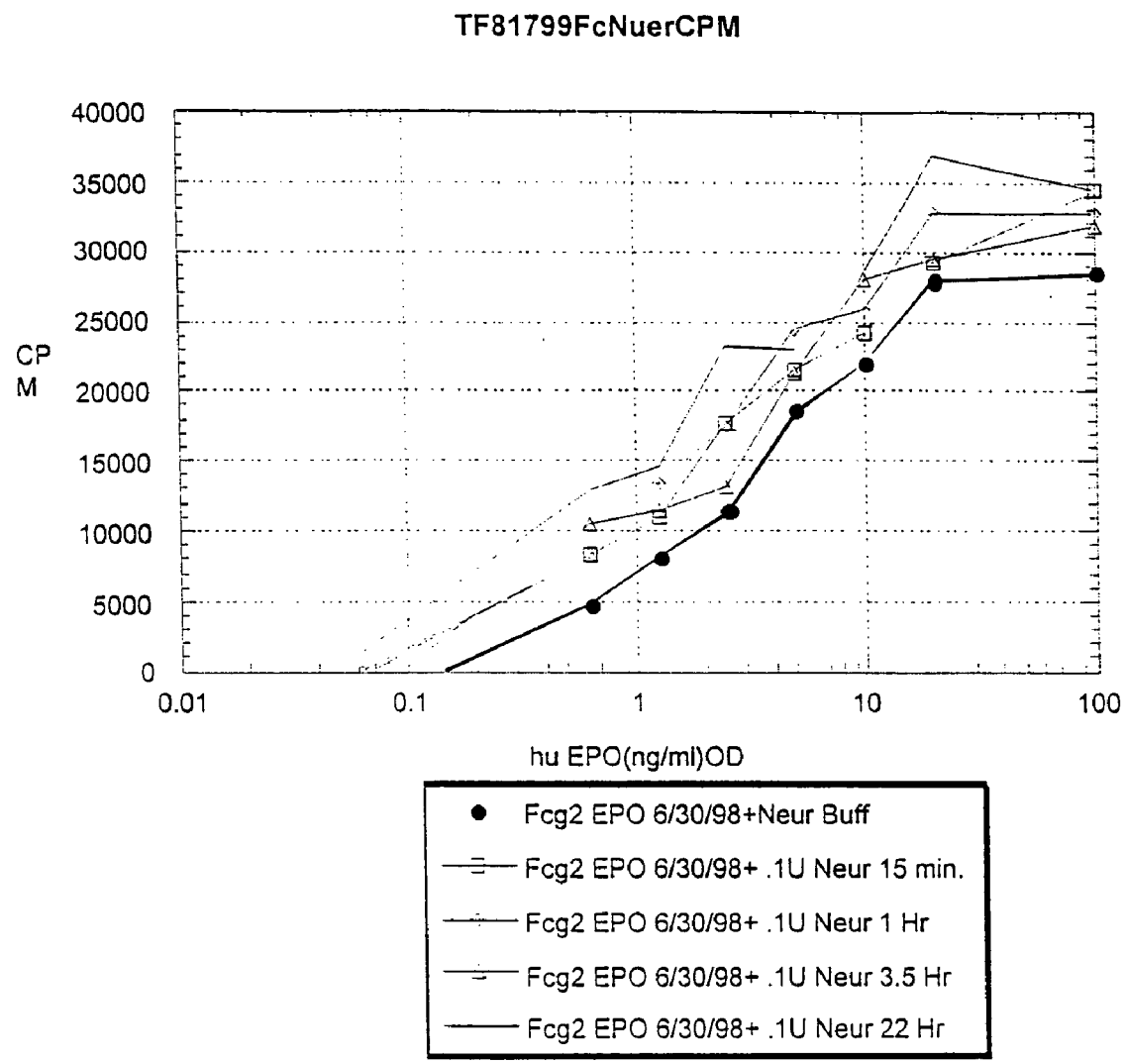

FIG. 3:
This figure depicts a line graph showing the biological activity of human IgG2 Fc-EPO treated with neuraminidase for various times. Fc-EPO was treated with buffer alone (black circles), 0.1 units of neuraminidase for 15 minutes (white squares), for 1 hour (white diamonds), for 3.5 hours (white triangles), or for 22 hours (white circles). The activity of the EPO moiety in various proteins was assayed via the EPO-dependent 3H-thymidine incorporation into TF-1 cells. The X-axis indicates the EPO equivalents (ng/ml) present, and the Y-axis indicates the dependent 3H-thymidine incorporation in counts per minute.

Figure 4:
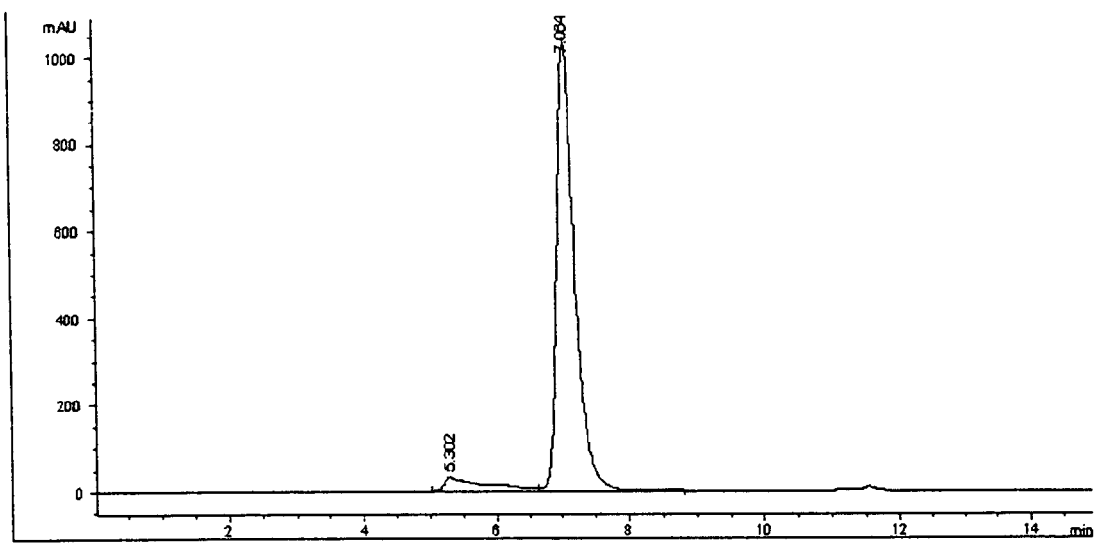

FIG. 4:
FIG. 4 depicts an HPLC profile of purified Fc-EPO in which the EPO moiety had the human EPO sequence except for the following alterations: $His_{32} \rightarrow Gly$, $Cys_{33} \rightarrow Pro$, $Trp_{88} \rightarrow Cys$, and $Pro_{90} \rightarrow Ala$. The peak at 7.064 represents (Fc-EPO)$_2$, and the peak at 5.302 represents aggregated material with a molecular weight of at least 800,000 daltons. The peak at 7.064 represents 93.2% of the detected material, while the peak at 5.302 represents 6.8% of the loaded material.

Figure 5:
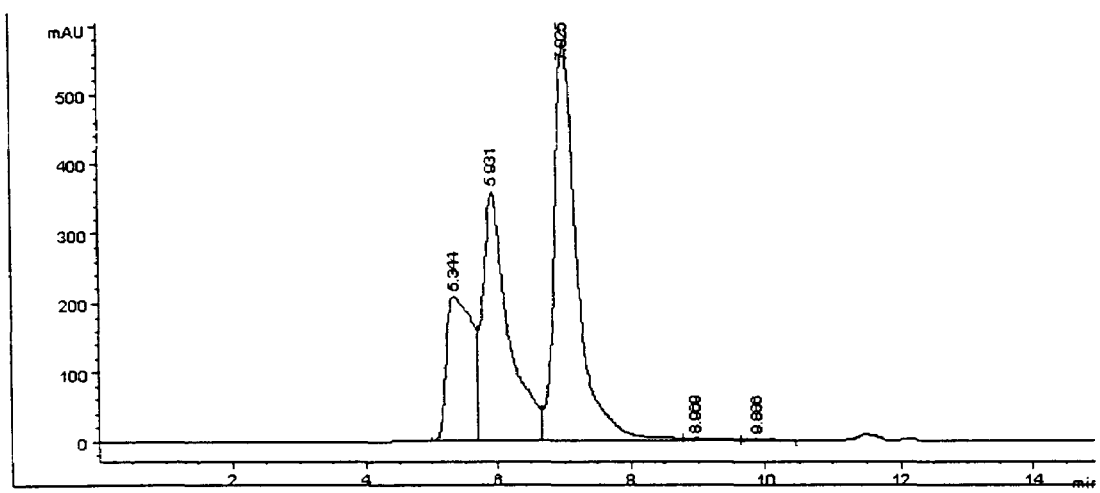

FIG. 5:
This figure depicts an HPLC profile of purified Fc-EPO in which the EPO moiety had the human EPO sequence. The peak at 7.254 represents (Fc-EPO)$_2$, the peak at 6.079 represents an oligomeric aggregate of (Fc-EPO)$_2$, and the peak at 5.330 represents aggregated material with a molecular weight of at least 800,000 daltons. The peak at 7.254 represents 43.4% of the detected material, while the peaks at 6.079 and at 5.330 respectively represent 30.5% and 25.2% of the loaded material.

SEQUENCE INFORMATION

The following DNA and amino acid sequences were used in this invention.

The coding sequence for mature EPO, using modified codons to optimize translation and including bases at the 5' end comprising the SmaI site is given in SEQ ID NO:1

SEQ ID NO:1
(Small characters indicate base differences from the human EPO coding sequence that are predicted to increase expression but not change protein sequence.)

CCCGGGtGCCCCACCACGCCTCATCTGT-
GACAGCCGAGTgCTGGAGAGGTACCTCTTG GAG-
GCCAAGGAGGCCGAGAATATCACGACcG-
GCTGTGCTGAACACTGCAGCTTGAA
TGAGAAcATCACcGTgCCtGACAC-
CAAAGTgAATTTCTATGCCTGGAAGAGGATGGAG
GTtGGcCAGCAGGCCGTAGAAGTgTG-

GCAGGGCCTGGCCCTGCTGTCGGAAGCTGTCC
TGCGGGGCCAGGCCCTGTTGCT-
CAACTCTTCCCAGCCGTGGGAGCCCCTGCAaCTGC
ATGTGGATAAAGCCGTgAGTGGCCTTCG-
CAGCCTCACCACTCTGCTTCGGGCTCTGgG AGC-
CCAGAAGGAAGCCATCTCCCCTCCAGAT-
GCGGCCTCAGCTGCTCCcCTCCGcAC
AATCACTGCTGACACTTTCCG-
CAAACTCTTCCGAGTCTACTCCAATTTC-
CTCCGGGGA AAGCTGAAGCTGTACACAGGGGAG-
GCCTgcCGGACAGGGGACAGATGActcgag SEQ ID NO:2 The mature EPO protein sequence (one-letter code)

APPRLICDSRVLERYLLEAKEAENTTG-
CAEHCSLNENITVPDTKVNFYAWKRMEVGQQ
AVEVWQGLALLSEAVLRGQALLVNSSQP-
WEPLQLHVDKAVSGLRSLTTLLRALGAQKE AISPP-
DAASAAPLRTITADTFRKLFRVYSNFL-
RGKLKLYTGEACRTGDR

Oligonucleotides used to construct a fusion of normally glycosylated EPO to the C-terminus of an Fc region.

SEQ ID NO:3

CCGGGtGCCCCACCACGCCTCATCTGT-GACAGCCGAGTgCTGGAGAGGTA CC

SEQ ID NO:4

TCTTGGAGGCCAAGGAGGCCGAGAATAT-CACGACcGGCTGTGCTGAACA

SEQ ID NO:5 Oligo 3

CTGCAGCTTGAATGAGAAcATCACcGT-gCCtGACACCAAAGTgAATTTCTAT

SEQ ID NO:6 Oligo 4

GCCTGGAAGAGGATGGAGGTtGGcCAG-CAGGCCGTAGAAGTgTGGCAG

SEQ ID NO:7 Oligo 5

GGCCTGGCCCTGCTGTCGGAAGCTGTC-CTGCGGGGCCAGGCCCTGTTGGTC

SEQ ID NO:8 Oligo 6

AACTCTTCCCAGCCGTGGGAGCCCCTG-CAaCTGCATGTGGATAAAGCCG

SEQ ID NO:9 Oligo 7

TgAGTGGCCTTCGCAGCCTCACCACTCT-GCTTCGGGCTCTGgGAGCCCAGAA

SEQ ID NO:10 Oligo 8

GGAAGCCATCTCCCCTCCAGATGCGGC-CTCAGCTGCTCCcCTCCGcAC

SEQ ID NO:11 Oligo 9

AATCACTGCTGACACTTTCCG-CAAACTCTTCCGAGTCTACTCCAATTTCCTCC

SEQ ID NO:12 Oligo 10

GGGGAAAGCTGAAGCTGTACACAGGG-GAGGCCTgcCGGACAGGGGACAGATGActcgag

Mutagenesis of Glycosylation Sites:

SEQ ID NO:13 Oligo 11 (oligo 2')

tc ttggaggcca aggaggccga gcagatcacg acgggctgtg ctgaaca TCTTGGAGGCCAAGGAGGCCGAGCAGAT-CACGACcGGCTGTGCTGAACA SEQ ID NO:14 Oligo 12 (oligo 3')

CTGCAGCTTGAATGAGCAGATCACcGT-gCCtGACACCAAAGTgAATTTCTAT

SEQ ID NO:15 Oligo 13 (oligo 6')

CAGTCTTCCCAGCCGTGGGAGCCCCTG-CAaCTGCATGTGGATAAAGCCG

SEQ ID NO:16 Oligo 14 (oligo 8')

GGAAGCCATCTCCCCTCCAGATGCGGC-CGCAGCTGCTCCcCTCCGcAC

SEQ ID NO:17

Human IgG1 Fc region-mature protein coding sequence

EPKSCDKTHTCPPCPAPELLGGPSVFLF-PPKPKDTLMISRTPEVTCVVVDVSHEDPEVKF NWYVDGVEVHNAKTKPREEQYNSTYRV-VSVLTVLHQDWLNGKEYKCKVSNKALPAPI EKTISKAKGQPREPQVYTLPPSREEMT-KNQVSLTCLVKGFYPSDIAVEWESNGQPENNY KTTP-PVLDSDGSFFLYSKLTVDKSRWQQGNVF-SCSVMHEALHNHYTQKSLSLSPGK

SEQ ID NO:18

Human IgG2 constant region—mature protein coding sequence (CH1, hinge, CH2, and CH3 regions)

ASTKGPSVFP LAPCSRSTSE STAALGCLVK DYFPEP-VTVS WNSGALTSGV HTFPAVLQSSGLYSLSSVVT VPSSNFGTQT YTCNVDHKPS NTKVDKTVER KCCVECPPCP APPVAGPSVFLFPPKPKDTL MISRTPE-VTC VVVDVSHEDP EVQFNWYVDG VEVHNAKTKP REEQFNSTFRVVSVLTVVHQ DWLNGKEYKC KVSNKGLPAP IEKTISKTKG QPREPQVYTL PPSREEMTKNQVSLTCLVKG FYPSDIAVEW ESNGQPENNY KTTPPMLDSD GSFFLYSKLT VDKSR-WQQGN VFSCSVMHEA LHNHYTQKSL SLSPGK

The following examples describe the invention in more detail without limiting it.

EXAMPLE 1

Expression of Human Fc-EPO

A sequence encoding the mature form of erythropoietin was completely synthesized from oligonucleotides by standard techniques. The oligonucleotides shown above and in the Sequence Listing indicate the 'top' strand of DNA encoding EPO protein; 'bottom' strand oligonucleotides were designed to pair with the top strands and to generate 4 to 5 base protruding 5' ends so that the entire EPO coding sequence could be ligated together after phosphorylation of the oligonucleotides. The sequence was designed to have a high G/C content with optimal codon usage for high-level expression.

The protein according to SEQ ID NO:2 does not have the N-terminal lysine residue of the mature protein. The synthesized DNA was engineered to have an XmaI-compatible overhang at the 5' end and an XhoI-compatible overhang at the 3' end. An alternative sequence was constructed with mutations in the four EPO glycosylation sites: $Asn_{24}$→Gln, $Asn_{38}$→Gln, $Asn_{83}$→Gln, and $Ser_{126}$→Ala. The 500 base-pair DNA was cloned and sequence analysis confirmed that it encodes the mature human EPO without additional undesired mutations.

The expression vector pdCs-Fc-EPO was constructed as follows. The XmaI-XhoI restriction fragment containing the human EPO cDNA was ligated to the XmaI-XhoI fragment of the pdCs-Fc vector according to Lo et al. [Protein Engineering (1998) 11:495]. The resultant vector, pdCs-Fc-EPO, was used to transfect mammalian cells for the expression of Fc-EPO. This vector expresses the human immunoglobulin gamma1 chain Fc region. A second set of Fc-EPO vectors were constructed in which the gamma1 chain Fc region was replaced with an Fc region derived from human gamma2.

The Fc protein moiety also usually contains a glycosylation site. This site may be optionally changed to a non-glycosylated sequence by standard approaches.

EXAMPLE 2

Transfection and Expression of Fc-EPO Fusion Proteins

For transient transfection, the plasmids were introduced into BHK cells. Cells were transfected by coprecipitation of plasmid DNA with calcium phosphate [Sambrook et al. (1989) Molecular Cloning—A Laboratory Manual, Cold Spring Harbor, N.Y.] or by lipofection using Lipofectamine Plus (Life Technologies, Gaithersburg, Md.) according to supplier's protocol.

To generate stable cell lines, NS/0 cells were used for both transient transfection and the generation of stable cell lines. To express proteins lacking the normal sialic acid modification, CHO-Lec2 cells (ATCC Number: CRL-1736) This cells exhibit a drastic reduction in the transport of CMP-sialic acid into the Golgi compartment, and are useful for studying the contribution of sialic acid in protein function.

In order to obtain stably transfected clones, plasmid DNA was introduced into cells by electroporation. About $5 \times 10^6$ cells were washed once with PBS and resuspended in 0.5 ml PBS. Ten μg of linearized plasmid DNA were then incubated with the cells in a Gene Pulser Cuvette (0.4 cm electrode gap, BioRad) on ice for 10 min. Electroporation was performed using a Gene Pulser (BioRad, Hercules, Calif.) with settings at 0.25 V and 500 microF. Cells were allowed to recover for 10 min. on ice, after which they were resuspended in growth medium and then plated onto two 96 well plates. Stably transfected clones were selected by growth in the presence of 100 nM methotrexate (MTX), which was introduced two days post-transfection. The cells were fed every 3 days for two to three more times, and MTX-resistant clones appeared in 2 to 3 weeks. Supernatants from clones were assayed by anti-Fc ELISA to identify high producers. High producing clones were isolated and propagated in growth medium containing 100 nM MTX.

BHK cells and NS/0 cells were grown in Dulbecco's modified Eagle's medium supplemented with 10% fetal bovine serum, 2 mM glutamine and penicillin/strepomycin. CHO-Lec2 cells were grown in alpha medium supplemented with 10% fetal bovine serum and penicillin/strepomycin. For routine characterization by gel electrophoresis, Fc fusion proteins in the conditioned media were captured on Protein A Sepharose (Repligen, Cambridge, Mass.) and then eluted by boiling in the protein sample buffer with or without 2-mercaptoethanol. After electrophoresis on an SDS gel, the protein bands were visualized by Coomassie staining. Fc-EPO had an apparent MW of about 64 kD on SDS-PAGE.

For purification, the fusion proteins bound on Protein A Sepharose were eluted in a sodium phosphate buffer (100 mM $NaH_2PO_4$, pH 3, and 150 mM NaCl). The eluate was then immediately neutralized with 0.1 volume of 2 M Tris-hydrochoride, pH 8.

EXAMPLE 3

Synthesis of Desialylated and Deglycosylated EPO and Fc-EPO Protein by Enzyme Treatment Sialic acid residues were removed from EPO and Fc-EPO by treatment with neuraminidase. Fc-erythropoietin protein at 500 micrograms/ml was treated with 0.1 units/ml of enzyme (Roche Biologicals) in a buffer containing 50 mM sodium acetate, 4 mM calcium chloride, 100 micrograms/ml bovine serum albumin at pH 5.5 for various times at 37° C.

Data in FIG. 2 illustrate that human IgG2 Fc-EPO treated with neuraminidase has an increased activity. For example, Fc-EPO that has been treated with neuraminidase for 22 hours has an activity equal to that of about 2 to 5 times as much normally sialylated Fc-EPO control protein.

To completely remove the N-linked sugar moieties, N-glycosidase treatment was used. Fc-erythropoietin protein at 500 micrograms/ml was treated with 0.02 units/ml of enzyme (Roche Biologicals) in a buffer containing 50 mM phosphate pH 7.8 for various times at 37° C. Alternatively, a buffer containing 50 mM phosphate pH 7.8, 20 mM EDTA, 1% Triton X-100, 1% beta-mercaptoethanol, and 0.1% SDS is used.

EXAMPLE 4

Characterization of Fc-EPO and Deglycosylated Fc-EPO

To characterize the deglycosylated forms of Fc-EPO that were generated by enzyme treatment or expression in mutant cell lines, SDS-PAGE and isoelectric focusing experiments were carried out. As determined by SDS-PAGE, the Fc-EPO protein that was deglycosylated by N-glycosidase treatment showed significantly faster mobility (FIG. 1).

The Fc-EPO protein is a dimer with four N-glycosylation sites and one O-glycosylation site in each subunit, for a total of ten glycosylation sites and 36 sialic acid residues. Each one of these sites is incompletely modified, so that Fc-EPO has many forms when analysed by IEF.

When Fc-EPO is treated with neuraminidase, certain IEF bands disappear and others appear, consistent with the removal of sialic acid by this enzyme. Similarly, Fc-EPO that is produced by from CHO-lec2 cells has a smaller number of less acidic forms.

EXAMPLE 5

ELISA Procedures

ELISAs were used to determine the concentrations of protein products in the supernatants of MTX-resistant clones and other test samples. The amounts of human Fc- and murine Fc-containing proteins were determined by the anti-huFc ELISA and the anti-muFc ELISA, respectively.

ELISA plates were coated with AffiniPure Goat anti-Human IgG (H+L) (Jackson Immuno Research Laboratories, West Grove, Pa.) at 5 μg/mL in PBS, and 100 μl/well in 96-well plates (Nunc-Immuno plate Maxisorp). Coated plates were covered and incubated at 4° C. overnight. Plates were then washed 4 times with 0.05% Tween (Tween 20) in PBS, and blocked with 1% BSA/1% goat serum in PBS, 200 μl/well. After incubation with the blocking buffer at 37° C. for 2 hrs, the plates were washed 4 times with 0.05% Tween in PBS and tapped dry on paper towels.

Coated plates were incubated with test samples diluted to the proper concentrations. Sample buffer contains 1% BSA, 1% goat serum and 0.05% Tween in PBS. A standard curve was prepared with a chimeric antibody (with a human Fc), the concentration of which was known. To prepare a standard curve, serial dilutions are made in the sample buffer to give a standard curve ranging from 125 ng/mL to 3.9 ng/mL. The diluted samples and standards were added to the plate, 100 µl/well and the plate was incubated at 37° C. for 2 hr. After incubation, the plate was washed 8 times with 0.05% Tween in PBS. To each well was then added 100 µl of the secondary antibody, the horseradish peroxidase-conjugated anti-human IgG (Jackson Immuno Research), diluted according to manufacturers instruction in the sample buffer. After incubation at 37° C. for 2 hr, the plate was washed 8 times with 0.05% Tween in PBS. Substrate solution have been added to the plate at 100 µl/well. The substrate solution was prepared by dissolving 30 mg of OPD (o-phenylenediamine dihydrochloride, 1 tablet) into 15 mL of 0.025 M Citric acid/0.05 M $Na_2HPO_4$ buffer, pH 5, which contained 0.03% of freshly added $H_2O_2$. The color was allowed to develop for 30 min. at room temperature in the dark. The developing time is subject to change, depending on lot to lot variability of the coated plates, the secondary antibody, etc. Watch the color development in the standard curve to determine when to stop the reaction. The reaction was stopped by adding 4N $H_2SO_4$, 100 µl/well. The plate was read by a plate reader, which was set at both 490 and 650 nm and programmed to subtract the background OD at 650 nm from the OD at 490 nm.

The procedure for the anti-muFc ELISA is similar, except that ELISA plate was coated with AffiniPure Goat anti-murine IgG (H+ L) (Jackson Immuno Research) at 5 µg/mL in PBS, and 100 µl/well; and the secondary antibody was horseradish peroxidase-conjugated goat anti-muIgG (Southern Biotechnology Assoc., Birmingham, Ala.).

EXAMPLE 6

In Vitro Activity of Human Fc-EPO Fusion Proteins

The methods below were and are used to test the activity of human Fc-EPO proteins produced by transient and stable expression. The amount of each fusion protein in the cell culture supernatant was first determined by ELISA and used to set up a dose-response curve. The activities closely corresponded to what was found with the Fc-EPO fusion proteins and described above.

Specifically, the EPO activity of a human Fc-EPO and asialo-human Fc-EPO molecules were tested in the TF-1 cell proliferation assay, following a standard procedure known to those practiced in the art of molecular immunology (Hammerling et al. [1996] J. Pharmaceutical and Biomedical Analysis 14:1455–1469; Kitamura et al. [1989] J. Cellular Physiol. 140:323–334). The human TF-1 cell line proliferates in response to EPO or other cytokines and growth factors. TF-1 cells in active log-phase growth were washed twice in medium lacking EPO and plated at about $1\times10^4$ cells per well in microtiter wells in the presence of various amounts of commercial EPO or Fc-EPO fusion protein with or without sialic acids. Cells were incubated in the presence of various test proteins for 48 hours, and 0.3 microCuries of $^3$H-thymidine was added ten hours before determining levels of radioactive incorporation. The various EPO and Fc-EPO fusion proteins stimulated incorporation of $^3$H-thymidine into cells in a dose-dependent manner, and were about equally effective in stimulating incorporation of $^3$H-thymidine on a per mole basis.

These results indicated that the in vitro biological activity of Fc-EPO increased upon desialylation by neuraminidase. The results also indicate that Fc-EPO fusion proteins, with or without sialylation, had activity similar to human EPO. Specifically, FIG. 1 indicates that the biological activity of normally sialylated human IgG2 Fc-EPO was about 2 to 5-fold less than that of enzymatically desialylated human IgG2 Fc-EPO, and the activities of these Fc-EPO fusion proteins were similar to the NIBSC EPO on a per mole basis.

EXAMPLE 7

Site-Directed Mutagenesis of Unglycosylated EPO

Mutations that increase the activity of unglycosylated EPO are introduced into the Fc-unglycosylated EPO fusion protein as follows. A DNA sequence encoding unglycosylated EPO is constructed as described in Example 1, except that one pair of oligonucleotides is replaced with a corresponding pair of oligonucleotides encoding a portion of EPO with one or more altered amino acids. For example, to introduce the change Asn147Ala, the oligonucleotide AAT-CACTGCTGACACTTTCCGCAAACTCTTC-CGAGTCTACTCCGCATTCCTCC (SEQ ID NO:27) is used instead of oligo 9 (SEQ ID NO:11), along with a correspondingly altered reverse-complement oligonucleotide.

The following mutations are introduced by this procedure: $Gly_{101}Ala$, $Arg_{143}Ala$, $Ser_{146}Ala$, and $Asn_{147}Ala$. These mutations most likely have the effect of increasing the activity of Fc-EPO by increasing its affinity for the EPO receptor. As another example, $Gln_{65}$ is mutated to an amino acid that has a smaller and/or more hydrophobic side chain. The effect of this mutation is to increase the fraction of Fc-EPO that is active. This effect is pronounced when mutations in the region of amino acids 114 to 130 are also present.

In other versions, cysteine residues are inserted and removed by substitution as described in Example 13. The resulting protein is more stable and more efficiently expressed, especially when combined with the mutations described above.

EXAMPLE 8

Testing Site-Directed Mutants for Activity

To rapidly test the mutant forms of Fc-unglycosylated EPO, the following strategy was used. A plasmid encoding each mutant form is transfected into mammalian cells, such as BHK cells. Tissue culture supernatant was withdrawn and quantitated by ELISA for human Fc, human EPO, and for activity in the TF1 cell proliferation assay. Four dilutions of each supernatant was tested in duplicate. The Fc-unglycosylated EPO concentrations in the dilutions was about 0.01 nM, 0.1 nM, 1 nM, and 10 nM.

EXAMPLE 9

Random Mutagenesis of Fc-EPO

To generate mutant forms of Fc-unglycosylated EPO without pre-selection, one of the following procedures is used. For example, the mature unglycosylated EPO coding sequence is synthesized as described in Example 1, except that 10 separate pools are generated. In the first pool, Oligo 1 and its reverse complement are synthesized with mixtures of oligonucleotide precursors so that each nucleotide has a 3% chance of being mutant. As a result, on average, each oligonucleotide will have 1 to 2 amino acid substitutions.

Similarly, in the second pool, Oligo 2 and its reverse complement are synthesized with mixtures of oligonucleotide precursors so that each nucleotide has a 3% chance of being mutant, and so on.

After ligation and transformation into E. coli, about 20 colonies are picked for each pool. DNA is made from each of the 20 transformants, and then separately introduced into a mammalian cell line such as BHK cells. Supernatant from each set of transiently transfected cells is then tested for EPO activity as described in Example 9.

Particular transfected BHK lines are found to produce EPO with greater specific activity. The corresponding DNA sequences of the mutant coding regions are determined. Based on these mutations and mutations identified in the Examples above, multiply mutant coding sequences are constructed. The corresponding multiply mutant proteins are expressed, and certain forms are found to have specific activities that are even greater than the individually mutant "parental" forms.

EXAMPLE 10

Pharmacokinetic Data

At present, erythropoietin is normally administered to patients three times per week (Physicians' Desk Reference [1996] "EPOgen: EPOetin Alfa", p. 489–496). The serum half-life of intravenously administered erythropoietin is about 4 to 13 hours. After subcutaneous administration of erythropoietin, serum levels peak within 5 to 24 hours. It would be advantageous to have a protein that stimulates red blood cell production but with a longer serum half-life than erythropoietin, so that dosing could be less frequent.

EXAMPLE 11

Pharmacokinetics of Fc-EPO Fusion Proteins

The human EPO protein and certain human Fc-EPO fusion proteins were tested for their pharmacokinetic behavior following intravenous injection into Balb/c mice. Blood was collected from mice by retro-orbital bleeding and stored at 4° C. in Eppendorf micro-centrifuge tubes. ELISA methods were used to measure the amount of human antibody-related proteins, such as the human Fc region, remaining in the blood at various time points. The ELISA measuring human antibody used an antibody against human H and L chains for capture and an anti-human Fc antibody for detection. A Western blot was used to verify that the Fc-erythropoietin fusion protein retained the correct size and was not degraded. As an alternative method to detect intact Fc-erythropoietin fusion protein moieties, a modified ELISA method was used. This fusion protein-specific assay uses the same first capture step, but an anti-human EPO antibody for detection. To detect EPO alone, both the capture antibody and the detection antibody are specific for human EPO. For example, the human EPO detection kit is used. The Fc-EPO fusion had a serum half-life of about 2 to 4 hours in these experiments. In contrast, the serum half-life of certain more elaborately engineered Fc-EPO fusions is tested and found to be much longer. For example, an intact antibody-EPO fusion is tested and has a serum half-life in mice of about 10 to 20 hours or longer.

The serum half-life of intact asialo-EPO was determined to be very short. As determined by Western blotting using antibodies against human IgG as a probe, the erythropoietin moiety of the asialo-Fc-EPO fusion protein is rapidly degraded while the Fc moiety is relatively stable and retained in the serum. These results indicate that only certain Fc-EPO fusion proteins have long serum half-lives, and that the Fc moiety is not universally sufficient to extend the serum half-life of a protein.

EXAMPLE 12

In Vivo Activity of Fc-EPO Fusion Proteins

The in vivo activity of the human Fc-EPO fusion protein was tested and compared with that of intact human EPO. On a per mole basis, the activity of Fc-erythropoietin is similar to that of intact human EPO using an assay that measures stimulation of red blood cell production within a short period after administration.

The activity of human EPO and IgG2 Fc-EPO was assayed in the normocythaemic mouse assay. One week before the beginning of the assay procedure, 8-week old male mice of the strain B6D2F1 were distributed into cages with six animals per cage. Within each cage group, each animal was injected with 0.5 mls of 10, 20 or 40 micrograms/ml of either erythropoietin or Fc-EPO, where the dose of Fc-EPO was measured by calculation of the amount of EPO monomers as determined by ELISA. For each experiment, 8 animals were used for each dose group.

Four days after the injections, blood samples were collected and the number of reticulocytes per 30,000 red blood cells was determined as follows. One microliter of whole blood was added to 1 milliliter of 0.15 micromolar acridine orange. After staining for 3 to 10 minutes, the reticulocyte count was determined microfluorometrically in a flow cytometer, by analysis of the red fluorescence histogram. The following data was obtained:

TABLE 1

Number of reticulocytes per 30,000 red blood cells

| | EPO | | | IgG2 Fc-EPO | | |
|---|---|---|---|---|---|---|
| Dose | 10 | 20 | 40 | 10 | 20 | 40 |
| Average | 1177 | 1422 | 1820 | 1036 | 1322 | 1732 |
| Standard deviation | 119 | 102 | 197 | 75 | 83 | 178 |

In a variation of this assay, mice are dosed with erythropoietin, Fc-Erythropoietin, Ig-Erythropoietin, and various other forms of Fc-EPO containing mutations, truncations, or altered glycosylation patterns. Reticulocytes are measured as described above, except that blood is sampled at 4 days, 5 days, 6 days, and 7 days following the injection of the test protein. Performing the experiment in this manner gives an indication of the functional pharmacokinetics of the test protein. It is found that certain forms of Fc-EPO, such as intact Ig-EPO, show functional activity over a longer period of time than normal EPO.

As an alternative method for measuring EPO activity, the in vivo activity of human EPO and Fc-EPO proteins is tested by the starved rat assay (Goldwasser E. and Gross M. Erythropoietin: assay and study of its mode of action. Methods Enzymol. [1975] 37 Pt B:109–21). Male Sprague-Dawley rates weighing about 215 to 250 grams (about 9 weeks old) are deprived of food on day 1. They are then injected i.v. with 2 mls of test material on days 2 and 3. The rats are divided into groups of five rats each. To generate a standard curve, one group is injected with physiological saline, and four other groups are injected with 1.0, 1.5, 2.0, or 3.0 Units of erythropoietin per rat, where 1.246 Units corresponds to 1 nanogram of glycoprotein (=26.7 femtomoles; check this). On day four, 28 hours after the second injection, the rats are injected i.p. with 1.0 microCuries of $^{59}$Fe$^{3+}$, in physiological saline buffered with citrate. Sixteen to eighteen hours after the $^{59}$Fe$^{3+}$ injection, the rats are anaesthetized and bled by cardiac puncture, using heparinized syringes. One ml of blood is withdrawn for counting the radiolabel, and a microhematocrit tube is also filled with blood. The animal is weighed. The percent of the injected $^{59}$Fe$^{3+}$ incorporated into the total red cell mass is calculated, assuming that the blood constitutes 5% of the weight of the animal. The hematocrits are recorded, and data from rats with hematocrits of less than 50 are discarded. The data are evaluated by subtracting the mean of the saline control group from the mean of each test group to obtain the percent incorporation that is stimulated by EPO or Fc-EPO fusion proteins. As another alternative, the in vivo activity of human EPO and Fc-EPO proteins is tested by the plethoric mouse assay assay assay (Goldwasser E. and Gross M. ibid). In this assay, mice are given a surplus of red blood cells so that erythropoiesis is suppressed. Methods of creating the plethora of red blood cells include exposure to low pressure (about 0.5 atmospheres), exposure to low oxygen at normal pressure, exposure to a low level of carbon monoxide, or exposure to a gradually decreasing O$_2$ partial pressure. The mice may be injected s.c. with 2.5 mg of iron-dextran before exposing them to the hypoxic stress, in order to insure that the mice have enough iron for the increased hemoglobin synthesis. Mice are returned to a normal oxygen environment on day 1 and injected with $^{59}$Fe$^{3+}$ on day 8.

Alternatively, mouse red cells are injected into the mice. For example, 1 ml of packed, washed isologous red blood cells is injected i.p. on days 1 and 3. Test samples include a saline control and standard doses of 0.05, 0.10 and 0.20 Units per mouse. These are injected on days 5 and 6, and $^{59}$Fe$^{3+}$ is injected on day 7, and the mice are bled on day 10. One ml of blood is counted. Some blood is used for a hematocrit. The mice are weighed. The percent of body weight represented by blood is assumed to be 8%. If a hematocrit is below 55, data for that mouse are not used.

Variations on these procedures, as well as other procedures, can also used to determine the in vivo activity of various forms of the EPO protein.

EXAMPLE 13

Construction and Expression of Fc-EPO Variants Containing Altered Patterns of Disulfide Bonding.

Mutations that alter the disulfide bonding pattern of the EPO moiety within Fc-EPO were introduced as follows. The alterations His$_{32}$Gly, Cys$_{33}$Pro, Trp$_{88}$Cys, and Pro$_{90}$Ala were introduced into human Fc-EPO by standard site-directed mutagenesis techniques. This protein was termed Fc-EPO (Cys$_{29}$–Cys$_{88}$). Fc-EPO (Cys$_{29}$–Cys$_{88}$) was expressed in mammalian cells by procedures analogous to those described in the preceding examples. Fc-EPO and Fc-EPO (Cys$_{29}$–Cys$_{88}$) protein were purified using a Staph A protein column as described in Example 2.

Fc-EPO (Cys$_{29}$–Cys$_{88}$) was found to be 1.5- to 2-fold more active than Fc-EPO in cell-based assays that measured proliferation of TF-1 cells. To investigate why Fc-EPO (Cys$_{29}$–Cys$_{88}$) was more active than Fc-EPO, each purified protein was examined by HPLC. FIGS. 4 and 5 show typical results. About ⅓ to ½ of the Fc-EPO protein migrated through the column with an apparent molecular weight of about 100,000 Daltons, which is the predicted molecular weight of dimeric Fc-EPO, but the remaining ½ to ⅔ of the Fc-EPO protein migrated with a much higher molecular weight, indicating that the Fc-EPO was in an aggregated state (for example, as in FIG. 4). SDS-PAGE, performed under denaturing and reducing conditions, indicated that this high-molecular weight material was not due to contamination with other proteins. In contrast, about 95% of the Fc-EPO (Cys$_{29}$–Cys$_{88}$) protein migrated through the HPLC column with an apparent molecular weight of 100,000 Daltons, and only about 5% of the Fc-EPO (Cys$_{29}$–Cys$_{88}$) was in an apparently aggregated state (for example, FIG. 5). Standard HPLC conditions were used.

To further investigate the enhanced stability of Fc-EPO (Cys$_{29}$–Cys$_{88}$), both Fc-EPO and Fc-EPO (Cys$_{29}$–Cys$_{88}$) were treated with N-glycanase, which removes the three N-linked oligosaccharides from erythropoietin. Standard digestion conditions were used in accordance with the manufacturer's instructions. Under these conditions, the N-linked oligosaccharides were completely removed from Fc-EPO and Fc-EPO (Cys$_{29}$–Cys$_{88}$) within 1 hour, as determined by SDS-PAGE—incubation longer than 1 hour had no effect on the migration of the Fc-EPO proteins, but it was found that further incubation under conditions of digestion with N-glycanase did cause Fc-EPO. However, not Fc-EPO (Cys$_{29}$–Cys$_{88}$), to rapidly lose biological activity, as described below.

After incubation of Fc-EPO or Fc-EPO (Cys$_{29}$–Cys$_{88}$) in the presence of N-glycanase for various times, the reaction was terminated by freezing at −20° C. and TF-1 cells were incubated with various dilutions of treated Fc-EPOs. Stimulation of $^3$H-thymidine incorporation was measured and compared with the NIBSC Erythropoietin standard. Results were obtained as shown in the table below.

TABLE II

Effect on biological activity of digestion of Fc-EPO and Fc-EPO (Cys$_{29}$-Cys$_{88}$) with N-glycanase.

| Treatment | Specific Activity (International units per mg of EPO moiety within a fusion protein) | |
| --- | --- | --- |
| | Fc-EPO | Fc-EPO (Cys29-Cys88) |
| None | 55,000 | 82,000 |
| N-glycanase treatment (0 min) | 55,000 | 89,000 |
| N-glycanase treatment (15 min) | 34,000 | 82,000 |
| N-glycanase treatment (60 min) | 3,290 | 67,000 |
| N-glycanase treatment (120 min) | 1,066 | 67,000 |

These results indicated that Fc-EPO (Cys$_{29}$–Cys$_{88}$) was much more stable upon N-glycanase treatment than Fc-EPO. Without wishing to be bound by theory, it may be that the N-glycanase buffer conditions, namely phosphate-buffered saline, are destabilizing to the deglycosylated EPO moiety within Fc-EPO, or that the N-glycanase is contaminated with proteases that inactivate the EPO moiety.

Introduction of the mutations in Fc-EPO (Cys$_{29}$–Cys$_{88}$) allows the formation of a disulfide bond between Cys$_{29}$ and Cys$_{88}$ of EPO. Similarly, introduction of analogous mutations into intact, unfused human EPO causes the formation of a disulfide bond between Cys$_{29}$ and Cys$_{88}$. The disulfide bond is identified by cleavage with a site-specific endoprotease such as trypsin under non-reducing conditions, followed by analysis of resulting peptides using mass spectrometry or HPLC analysis.

For example, the following set of experiments with controls is performed. Human Fc-EPO, human Fc-EPO (Cys$_{29}$–Cys$_{88}$), human EPO, and human EPO (Cys$_{29}$–Cys$_{88}$) are cleaved with trypsin in both reducing and non-reducing conditions. These eight samples are analyzed by mass spectrometry. Trypsinized non-reduced human Fc-EPO (Cys$_{29}$–Cys$_{88}$) and human EPO (Cys$_{29}$–Cys$_{88}$) each give a peak with a high molecular weight, corresponding to EAENITTGCAEGPSLNENITVPDTK (SEQ ID NO:28)+ GQALLVNSSQPCEALQLHVDK (SEQ ID NO:29) with two N-linked glycosylations. Because of its large size and heterogeneity due to the presence of two N-glycosylations, this peak is easily distinguished from the other peaks. This peak is not found in reduced samples or in samples derived from non-mutant human EPO or non-mutant human Fc-EPO. As a further diagnostic test, samples are incubated with N-glycanase before treatment with trypsin.

In the samples treated with N-glycanase, the peak corresponding to EAENITTGCAEGPSLNENITVPDTK (SEQ ID NO:28, corresponding to pos. 21–45, SEQ ID NO:2)+ GQALLVNSSQPCEALQLHVDK (SEQ ID NO:29, corresponding to pos. 77–97, SEQ ID NO:2) is shifted to the size predicted by the molecular weights of the amino acids alone.

The Fc-EPO ($Cys_{29}$–$Cys_{88}$) is tested further and found to be advantageous in other ways. For example, Fc-EPO ($Cys_{29}$–$Cys_{88}$) has superior pharmacokinetic properties when tested in mice, humans, or other mammals. Lyophilized forms of Fc-EPO ($Cys_{29}$–$Cys_{88}$) and EPO ($Cys_{29}$–$Cys_{88}$) are more stable than the corresponding Fc-EPO and EPO proteins. In long-term stability studies, such as studies of remaining biological activity after extended incubation at elevated temperatures, Fc-EPO ($Cys_{29}$–$Cys_{88}$) and EPO ($Cys_{29}$–$Cys_{88}$) are more stable than the corresponding Fc-EPO and EPO proteins. Fc-EPO ($Cys_{29}$–$Cys_{88}$) and EPO ($Cys_{29}$–$Cys_{88}$) are more resistant to proteases than the corresponding Fc-EPO and EPO proteins.

In addition, it is sometimes useful to introduce mutations into the EPO moiety that are advantageous in certain aspects but that also decrease the stability of the EPO moiety. In such cases, it is useful to also introduce one or more mutations that cause the formation of a disulfide bond between $Cys_{29}$ and $Cys_{88}$. The effect of the additional disulfide bond is to enhance the stability of the mutated EPO. For example, mutation of $Gly_{101}$→Ala, $Arg_{143}$→Ala, $Ser_{146}$→Ala, and $Asn_{147}$→Ala increases the signaling activity of EPO. Mutations of this type have advantages with regard to certain properties of EPO, but destabilize the protein for purposes of pharmaceutical development.

The advantageous properties of a mutation or mutations that cause the formation of a disulfide bond between $Cys_{29}$ and $Cys_{88}$ in EPO are also observed in intact EPO without an attached Fc moiety, and also in other forms of EPO such as fusion proteins of EPO to other moieties, forms of EPO that have reduced, increased, or qualitatively altered glycosylation levels, and so on.

In a similar set of experiments, an expression plasmid encoding human Fc-EPO protein containing the mutations $Arg_{139}$→Cys and $Cys_{29}$ to another amino acid such as Ala, Val, Leu, or Ile is constructed analogously to the construction of Fc-EPO ($Cys_{29}$–$Cys_{88}$). Analysis by protease treatment and mass-spectrometry indicates that this protein contains a disulfide bond between $Cys_{33}$ and $Cys_{139}$ and is therefore termed Fc-EPO ($Cys_{33}$–$Cys_{139}$). An analogous expression plasmid encoding human EPO containing the mutations $Arg_{139}$→Cys and $Cys_{29}$ to another amino acid such as Ala, Val, Leu, or Ile is also constructed. Fc-EPO ($Cys_{33}$–$Cys_{139}$) has a number of advantageous properties. For example, Fc-EPO ($Cys_{33}$–$Cys_{139}$) is primarily in the normal, dimeric form and is less aggregated than human Fc-EPO. For example, when purified Fc-EPO ($Cys_{33}$–$Cys_{139}$) is analyzed by HPLC, most of the material migrates with an apparent molecular weight of about 100 kD. Another advantageous property is that Fc-EPO ($Cys_{33}$–$Cys_{139}$) is more active than human Fc-EPO. Without wishing to be bound by theory, it is most likely that the 100 kD form of both Fc-EPO ($Cys_{33}$–$Cys_{139}$) and human Fc-EPO is the active form, and the forms with a high apparent molecular weight, as determined by HPLC, have little or no activity. Even though the Fc-EPO ($Cys_{33}$–$Cys_{139}$) and Fc-EPO ($Cys_{29}$–$Cys_{88}$) have increases in activity of 25% to 100%, this improved activity is economically significant because these proteins are expensive to make and large quantities are used to treat the large population of patients who are anemic.

Fc-EPO ($Cys_{33}$–$Cys_{139}$) also shows improved pharmacokinetics compared to human Fc-EPO. Fc-EPO ($Cys_{33}$–$Cys_{139}$) also shows improved long-term stability in solution and in a lyophilized form as compared to human Fc-EPO.

Fc-EPO ($Cys_{33}$–$Cys_{139}$) also has the advantageous property that, in the presence of additional alterations or mutations that destabilize human Fc-EPO, the protein has significantly enhanced stability.

The advantageous properties of Fc-EPO ($Cys_{33}$–$Cys_{139}$) are also observed with EPO ($Cys_{33}$–$Cys_{139}$) without the Fc moiety. For example, EPO ($Cys_{33}$–$Cys_{139}$) has enhanced stability, improved activity, superior pharmacokinetics, improved long-term stability, and significantly enhanced stability in the presence of additional destabilizing alterations.

Other useful forms of human Fc-EPO and human EPO include multiply mutant proteins that have disulfide bonds between $Cys_{29}$ and $Cys_{88}$ as well as between $Cys_{33}$ and $Cys_{139}$. For example, EPO ($Cys_{29}$–$Cys_{88}$+$Cys_{33}$–$Cys_{139}$) has enhanced stability, improved activity, superior pharmacokinetics, improved long-term stability, and significantly enhanced stability in the presence of additional destabilizing mutations.

Human Fc-EPO and human EPO are engineered to have advantageous properties by the introduction of other disulfide bonds. The design of such disulfide bonds can be guided by the known structure of human EPO, which has been determined using X-ray crystallography and NMR. For example, $Ala_{22}$ and $Phe_{142}$ of human EPO or human Fc-EPO are each replaced by cysteine, and a disulfide bond forms between these new cysteines. To compensate for the empty volume within the hydrophobic core of the EPO moiety that results from the replacement of $Phe_{142}$ with the smaller cysteine, another nearby amino acid side chain within the hydrophobic core is optimally replaced with a large side chain. For example, $Val_{74}$ is replaced with Phe, Leu, Tyr, Ile, or Met. The resulting protein with an additional disulfide has enhanced stability, improved activity, superior pharmacokinetics, improved long-term stability, and significantly enhanced stability in the presence of additional destabilizing mutations.

The invention claimed is:

1. A fusion protein comprising an Fc portion of an Ig molecule and an erythropoietin (EPO) portion, wherein (i) the Fc portion is fused covalently via its C-terminus directly or indirectly to the EPO portion, (ii) the EPO portion comprises a Cys at a position corresponding to $Trp_{88}$ of human erythropoietin and an amino acid other than Cys at a position corresponding to position 33 of human erythropoietin such that the EPO portion comprises a $Cys_{29}$–$Cys_{88}$ disulfide bond, and (iii) the EPO portion retains erythropoietin activity.

2. The fusion protein of claim 1, wherein the EPO portion is derived from human erythropoietin.

3. The fusion protein of claim 1, wherein the Fc portion is mutated or truncated in its amino acid sequence.

4. The fusion protein of claim 1, wherein the Fc portion is modified in its glycosylation pattern.

5. The fusion protein of claim 1, wherein the Fc portion is derived from an IgG chain and comprises a mutation of the glycosylation site within the Fc portion of the IgG chain.

6. The fusion protein of claim 5, wherein the mutation is of an asparagine at an amino acid position corresponding to position 297 of IgG1.

7. The fusion protein of claim 1 further comprising a linker between the Fc portion and the EPO portion.

8. The fusion protein of claim 7, wherein the linker has no protease cleavage site.

9. The fusion protein of claim 1 having improved biological activity compared to naturally-occurring human erythropoietin.

10. The fusion protein of claim 1 having an extended serum half-life compared to naturally-occurring human erythropoietin.

11. The fusion protein of claim 10, wherein said extended serum half-life is greater than 20 hours.

12. The fusion protein of claim 1, comprising a whole Ig molecule.

13. The fusion protein of claim 1, wherein the Fc portion and the EPO portion are of mammalian origin.

14. The fusion protein of claim 13, wherein the Fc portion is derived from human IgG.

15. A pharmaceutical composition comprising the fusion protein of claim 1 and a pharmaceutically acceptable carrier, diluent or excipient.

16. The pharmaceutical composition of claim 15 containing at least one additional pharmaceutically effective drug and/or adjuvants.

17. A fusion protein comprising an Fc portion of an Ig molecule and an erythropoietin (EPO) portion, wherein (i) the Fc portion is fused covalently via its C-terminus directly or indirectly to the EPO portion, (ii) the EPO portion comprises a Cys at a position corresponding to $Trp_{88}$ of human erythropoietin and an amino acid other than Cys at a position corresponding to position 33 of human erythropoietin such that the EPO portion comprises a $Cys_{29}$–$Cys_{88}$ disulfide bond, (iii) the EPO portion retains erythropoietin activity and is derived from human erythropoietin; and (iv) the EPO portion comprises at least one of the following mutations: $His_{32} \rightarrow Gly$, $Ser_{34} \rightarrow Arg$, and $Pro_{90} \rightarrow Ala$.

18. A fusion protein comprising an Fc portion of an Ig molecule and an erythropoietin (EPO) portion, wherein (i) the Fc portion is fused covalently via its C-terminus directly or indirectly to the EPO portion, (ii) the EPO portion comprises a Cys at a position corresponding to $Trp_{88}$ of human erythropoietin and an amino acid other than Cys at a position corresponding to position 33 of human erythropoietin such that the EPO portion comprises a $Cys_{29}$–$Cys_{88}$ disulfide bond, (iii) the EPO portion retains erythropoietin activity and is derived from human erythropoietin; and (iv) the EPO portion comprises the following substitutions: $His_{32} \rightarrow Gly$, $Cys_{33} \rightarrow Pro$, $Trp_{88} \rightarrow Cys$, and $Pro_{90} \rightarrow Ala$.

* * * * *